US008642839B2

(12) United States Patent
Azhakanandam

(10) Patent No.: US 8,642,839 B2
(45) Date of Patent: Feb. 4, 2014

(54) METHOD FOR THE TRANSIENT EXPRESSION OF NUCLEIC ACIDS IN PLANTS

(75) Inventor: Kasimalai Azhakanandam, Durham, NC (US)

(73) Assignee: Syngenta Participations AG, Basel (CH)

( * ) Notice: Subject to any disclaimer, the term of this patent is extended or adjusted under 35 U.S.C. 154(b) by 495 days.

(21) Appl. No.: 12/813,681

(22) Filed: Jun. 11, 2010

(65) Prior Publication Data

US 2010/0319089 A1 Dec. 16, 2010

Related U.S. Application Data

(60) Provisional application No. 61/186,025, filed on Jun. 11, 2009.

(51) Int. Cl.

| | |
|---|---|
| ***A01H 5/10*** | (2006.01) |
| ***C07K 14/415*** | (2006.01) |
| ***G01N 33/564*** | (2006.01) |

(52) U.S. Cl.
USPC ........ 800/294; 800/320.1; 800/287; 435/469; 435/7.92; 435/6.12

(58) Field of Classification Search
None
See application file for complete search history.

(56) References Cited

U.S. PATENT DOCUMENTS

| | | | |
|---|---|---|---|
| 5,187,073 | A | 2/1993 | Goldman et al. |
| 5,569,597 | A | 10/1996 | Grimsley et al. |
| 6,162,965 | A | 12/2000 | Hansen |
| 6,635,806 | B1 | 10/2003 | Kriz et al. |
| 6,660,911 | B2 | 12/2003 | Fincher et al. |
| 6,740,526 | B1 | 5/2004 | Curtis |
| 6,781,044 | B2 | 8/2004 | Rodriguez et al. |
| 2004/0148656 | A1 | 7/2004 | Negrouk et al. |
| 2008/0057563 | A1 | 3/2008 | Marillonnet et al. |

FOREIGN PATENT DOCUMENTS

| | | |
|---|---|---|
| CN | 101096682 | 1/2008 |
| WO | WO 99/14348 | 3/1999 |
| WO | WO 99/20776 | 4/1999 |
| WO | WO 00/63398 | 10/2000 |
| WO | WO 01/07601 | 2/2001 |
| WO | WO 01/12828 | 2/2001 |
| WO | WO 02/44323 | 6/2002 |
| WO | WO 03/079765 | 10/2003 |
| WO | WO 2004/047522 | 6/2004 |
| WO | WO 2005/024034 | 3/2005 |
| WO | WO 2005/036953 | 4/2005 |
| WO | WO 2005/076766 | 8/2005 |
| WO | WO 2006/003018 | 1/2006 |
| WO | WO 2006/042979 | 4/2006 |
| WO | WO 2008/036424 | 3/2008 |

OTHER PUBLICATIONS

Ahmadabadi et al. (Transgenic Res (2007) 16:437-448, 12 pages total.*
International Maize and Wheat Improvement Center (Maize growth stages), http://maizedoctor.cimmyt.org/en/getting-started/9?task=view. 1 page total.*
Saha et al. (Planta (2006) 223: 1329-1343), 15 pages total.*
Harn et al. (Plant Molecular Biology 37: 639-649, 1998.), 11 pages total.*
Marillonnet et al. (PNAS, May 4, 2004 vol. 101 No. 18 6852-6857).*
Dybvig et al. (Journal of Bacteriology, Aug. 2000, p. 4343-4347 vol. 182, No. 15).*
Fischer et al., Biotechnol Appl Biochem, 1999, 30, pp. 113-116.
Vaquero et al., Proc Natl Acad Sci, 1999, 96, pp. 11128-11133.
Bansal et al., Proc Natl Acad Sci, 1992, 89, pp. 3654-3658.
Voinnet et al., The Plant Journal, 2003, 33, pp. 949-956.
Christou, Trends in Plant Science, 1996, 12, pp. 423-431.
Fischer et al., Biotechnol Appl Biochem, 1999, 30, pp. 101-108.
Sawers et al., Plant Methods, 2006, 2, 15, 10 pages.
Vasil et al., Plant Physiol, 1989, 91, pp. 1575-1579.
Janssen et al., Plant Molecular Biology, 1989, 14, pp. 61-72.
Hamilton et al., Plant Molecular Biology, 1992, 18, pp. 211-218.
Grimsley, Physiologia Plantarum, 1990, 79, pp. 147-153.
Grimsley, Nature, 1987, 325, pp. 177-179.
Shen et al., The Plant Journal, 1994, 5, 2, pp. 227-236.
Martin et al., Phytopathology, 1999, 89, 8, pp. 695-700.
Grimsley, Biotechnology, Feb. 1988, 6, pp. 185-189.
Azhakanandam et al., Plant Mol Biol, 2007, 63, pp. 393-404.
Simmons et al., Biotechnology and Bioengineering, 2009, 102, 3, pp. 965-970.
Chumakov et al., Russian Journal of Genetics, 2006, 42, 8, pp. 893-897.
Supartana et al., Journal of Bioscience and Bioengineering, 2006, 102, 3, pp. 162-170.
Wagner et al., Methods, 2004, 32, 3, pp. 227-234.
Hanson et al., PNAS, 1996, 93, 25, pp. 14978-14983.
Chowrira et al., Molecular Biotechnology, 1996, 5, 2, pp. 85-96.
Donath et al., Plant Molecular Biology, 1995, 28, 4, pp. 667-676.
Risacher et al., Methods in Molecular Biology, 2008, 478, pp. 115-124.
Plesha et al., Abstracts of Papers, 232nd ACS National Mtg, San Francisco, CA Sep. 10-14, 2006, BIOT-246, Publisher: ACS, Washington, D.C.

(Continued)

*Primary Examiner* — David T Fox
*Assistant Examiner* — Jared Shapiro
(74) *Attorney, Agent, or Firm* — Yoshimi D. Barron

(57) ABSTRACT

Compositions and methods for transiently expressing proteins in a plant are provided. The compositions comprise plants, seeds, plant tissues, and plant parts expressing a protein, wherein the protein is expressed transiently and the transient expression of the protein can be used as a predictive model of how said protein will be expressed in stable transgenic plants in regards to qualitative and quantitative data. The predictive model may be used but is not limited to: promoter evaluation, evaluation of expression cassette construction for best performance (e.g. addition of enhancers or gene silencing suppressors), evaluation of best ways to express heterologous genes (e.g. point mutations, targeting), fast evaluation of endogenous gene knockout, evaluation of protein expression levels, cellular targeting, tissue targeting, transcriptional enhancers, translational enhancer protein toxicity and metabolic profiling. Further provided are methods of use.

20 Claims, No Drawings

(56) References Cited

OTHER PUBLICATIONS

Sanshi et al., In planta phenotypic transformation method of important crops including mulberry, 2006, 75, 3, pp. 183-185.
Song et al., Plant Biotechnology, 2003, 20, 3, pp. 235-239.
Ramani et al., Biochemical and Biophysical Research Communications, 1997, 233, 3, pp. 663-667.
Heath et al., Molecular Plant-Microbe Interactions, 1997, 10, 2, pp. 221-227.
Gallo-Meagher et al., Plant Cell Reports, 1993, 12, 12, pp. 666-670.
Ritchie et al., Transgenic Research, 1993, 2, 5, pp. 252-265.
Maas et al., Physiologia Plantarum, 1992, 85, 2, pp. 367-373.
Dekeyser et al., Plant Cell, 1990, 2, 7, pp. 591-602.
Choi et al., Plant Pathology Journal, 2008, 24, 3, pp. 296-304.
International Search Report and Written Opinion dated Aug. 11, 2010 for PCT/US10/38271.

* cited by examiner

METHOD FOR THE TRANSIENT EXPRESSION OF NUCLEIC ACIDS IN PLANTS

CROSS REFERENCE TO RELATED APPLICATIONS

The following application claims priority to U.S. Provisional Application No. 61/186,025; filed Jun. 11, 2009

FIELD OF THE INVENTION

This invention relates generally to transgenic plants. More specifically, it relates to methods and compositions of expressing transgenes in plants.

BACKGROUND OF THE INVENTION

Advances in molecular biology have enhanced the ability of scientists to manipulate the genome of animals and plants. Genes controlling various aspects of plant and animal molecular processes may be identified and isolated from the genomes of those respective organisms. For example, genes conferring antibiotic, herbicide, and insect or drought resistance have been isolated from various organisms. Even more important is the ability to take a gene isolated from one organism and introduce said gene into another organism (heterologous transformation). This integration may be accomplished even where the recipient organism is from a different phylum, genus or species from that which the gene was derived.

Generally, plant transformation relies on two approaches for delivery and expression of foreign genes in plants: stable genetic transformation and transient expression. A number of genetic engineering techniques have been employed to stably introduce desired traits into plant genomes. The introduction of these desired traits have been accomplished by means including *Agrobacterium* infection (Nester et al., 1984), polyethylene glycol (PEG)-mediated DNA uptake (Lorz et al., 1985), electroporation of protoplasts (Fromm et al., 1986) and microprojectile bombardment (Klein et al., 1987). Many plant species may now be transformed stably on a routine basis by using the aforementioned methods or variants thereof (for review see: Christou et al., 1996, *Trends Plant Sci.* 1, 423-431). Plant transient expression can be accomplished through agro-infiltration, particle bombardment or viral infection (for review see: Fischer et al., 1999, *Biotechnol. Appl. Biochem.,* 30, 113-116).

Transient expression of nucleic acids has great potential as a means to predict how any gene, promoter, expression cassette, or other elements might perform in a stable transgenic plant. The development of a transient expression in planta assay to permit rapid evaluation of heterologous gene expression in plants is highly desirable. The conventional establishment and characterization of a stable transgenic plant line involves a long process often taking more than two years. It would be ideal to have a rapid transient assay method to quickly evaluate how an expression cassette and or its associated elements (i.e. promoter, gene, enhancers) will perform in stable plant lines. For instance, it would be ideal to have a transient method where one could quickly correlate by using transient data the best expression method (i.e. cellular targeting, enhancer combinations, promoter selection, etc) to be employed in stable plant lines. This method could also be utilized to quickly identify expression problems such as protein cleavage, tissue toxicity, unfavorable phenotypes as well as other problems that could be identified prior to investing time and resources to express gene candidates in stable plant lines. Transient expression can be achieved by agro-infiltrating plant tissue with a standard expression cassette under control of a constitutive promoter such as the 35S promoter to drive expression of the gene of interest (Vaquero et al., 1999, *Proc. Natl. Acad. Sci. US,* 96, 11128-11133). One disadvantage of transiently expressing genes of interest using the agro-infiltration method is that the method results in very low protein expression levels. Low protein expression makes it difficult to correlate how a gene or expression cassette might perform stably in planta. It has been found that the inclusion of post-transcriptional gene silencing suppressors in agro-infiltration, such as p19 or HcPro, results in a 50 fold increase in transient expressed protein (Voinnet et al., 2003, *Plant J.,* 33, 549-556). Though the transient protein expression levels are higher, agro-infiltrated transient expression employing post-transcriptional gene silencing suppressors can in some cases be inconsistent in regards to protein expression and not at all predictive of how a given gene or expression cassette might perform in stable plants. Viral vectors may also be used to transiently express proteins of interest. Viral vectors overcome the problem of producing high transient expression levels (for review see: Porta & Lomonossoff, 1996, *Mol. Biotechnol.,* 5, 209-221; Yusibov et al., 1999, *Curr. Top. Microbiol. Immunol.,* 240 81-94). However, the use of viral vectors to transiently express a protein in plants is limited by a narrow host range in terms of their best performance as well as limitations to gene size. There is also the issue that no transient assay method has been identified to work consistently across a variety of plant species. Monocots are an especially difficult group of plants to consistently express genes of interest transiently in a manner that transient data may be used as a predictive indicator of how a gene or expression cassette may perform in stable plant lines. Of particular interest, would be a transient expression in planta assay method that could work in cereal crops (e.g. maize or wheat), sugarcane, sugar beet, soybean, rice as well as other commercially important crops.

SUMMARY OF THE INVENTION

Compositions and methods for transiently expressing proteins in a plant are provided. The compositions comprise plants, seeds, plant tissues, and plant parts expressing a protein, wherein the protein is expressed transiently and the transient expression of the protein can be used as a predictive model of how said protein will be expressed in stable transgenic plants in regards to qualitative and quantitative data. The predictive model may be used but is not limited to: promoter evaluation, evaluation of expression cassette construction for best performance (e.g. addition of enhancers or gene silencing suppressors), evaluation of best ways to express heterologous genes (e.g. point mutations, targeting), fast evaluation of endogenous gene knockout, evaluation of protein expression levels, cellular targeting, tissue targeting, transcriptional enhancers, translational enhancer protein toxicity and metabolic profiling. Further provided are methods of use.

Downstream uses of the transient assay method comprising the methods described herein include agronomical, pharmaceutical, and industrial uses, for example, human food, animal feed, biofuel, industrial alcohol, fermentation feedstocks, and the like.

These and other features, objects and advantages of the present invention will become better understood from the description that follows. The description of preferred embodiments is not intended to limit the invention to cover all modifications, equivalents and alternatives. Reference should therefore be made to the claims recited herein for interpreting the scope of the invention.

Definitions

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention. As used herein the singular forms "a", "and", and "the" include plural reference unless the context clearly dictates otherwise. Thus, for example, reference to "a vector" is a reference to one or more vectors and includes equivalents thereof known to those skilled in the art.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent.

As used herein, the word "or" means any one member of a particular list and also includes any combination of members on that list.

"Antisense inhibition" refers to the production of antisense RNA transcripts capable of suppressing the expression of protein from an endogenous gene or a transgene.

"Cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

"Chimeric" is used to indicate that a DNA sequence, such as a vector or a gene, is comprised of two or more DNA sequences of distinct origin that are fused together by recombinant DNA techniques resulting in a DNA sequence, which does not occur naturally.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation, or splicing, of the RNA within the cell to create the mature mRNA that can be translated into a protein.

"Constitutive promoter" refers to a promoter that is able to express the gene that it controls in all or nearly all of the plant tissues during all or nearly all developmental-stages of the plant, thereby generating "constitutive expression" of the gene.

"Co-suppression" and "sense suppression" refer to the production of sense RNA transcripts capable of suppressing the expression of identical or substantially identical transgene or endogenous genes.

"Contiguous" is used herein to mean nucleic acid sequences that are immediately preceding or following one another.

"Expression" refers to the transcription and stable accumulation of mRNA.

Expression may also refer to the production of protein.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components.

The "expression pattern" of a promoter (with or without an enhancer) is the pattern of expression that shows where in the plant and in what developmental stage the promoter initiates transcription. Expression patterns of a set of promoters are said to be complementary when the expression pattern of one promoter shows little overlap with the expression pattern of the other promoter.

"Gene" refers to a nucleic acid fragment that expresses mRNA, functional RNA, or specific protein, including regulatory sequences. The term "Native gene" refers to a gene as found in nature. The term "chimeric gene" refers to any gene that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature. A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but one that is introduced into the organism by gene transfer.

An "isolated" nucleic acid sequence is substantially separated or purified away from other nucleic acid sequences with which the nucleic acid is normally associated in the cell of the organism in which the nucleic acid naturally occurs i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids. The term "substantially purified", as used herein, refers to a molecule separated from other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

A "synthetic nucleic acid sequence" can be designed and chemically synthesized for enhanced expression in particular host cells and for the purposes of cloning into appropriate constructs. Host cells often display a preferred pattern of codon usage (Murray et al., 1989). Synthetic DNAs designed to enhance expression in a particular host should therefore reflect the pattern of codon usage in the host cell. Computer programs are available for these purposes including but not limited to the Vector NTI Advanced Software Package Release 10.0, Invitrogen, Carlsbad Calif.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes. (English, et al., 1996, Plant Cell 8:179-1881). Gene silencing includes virus-induced gene silencing (Ruiz et al., 1998, Plant Cell 10:937-946).

"Genetically stable" and "heritable" refer to chromosomally-integrated genetic elements that are stably maintained in the plant and stably inherited by progeny through successive generations.

"Heterologous DNA Sequence" is a DNA sequence not naturally associated with a host cell into which it is introduced, including non-naturally occurring multiple copies of a naturally occurring DNA sequence.

"Inducible promoter" refers to those regulated promoters that can be turned on in one or more cell types by an external stimulus, such as a chemical, light, hormone, stress, or a pathogen.

"Insecticidal" is defined as a toxic biological activity capable of controlling insects, preferably by killing them.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency. (Turner et al., 1995, Molecular Biotechnology, 3:225).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989, Plant Cell, 1:671-680).

The term "nucleic acid" refers to a polynucleotide of high molecular weight which can be single-stranded or double-stranded, composed of monomers (nucleotides) containing a sugar, phosphate and a base which is either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Operably-linked" and "Operatively-linked" refer to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Overexpression" refers to the level of expression in transgenic organisms that exceeds levels of expression in normal or untransformed organisms.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

"Preferred expression", "Preferential transcription" or "preferred transcription" interchangeably refers to the expression of gene products that are preferably expressed at a higher level in one or a few plant tissues (spatial limitation) and/or to one or a few plant developmental stages (temporal limitation) while in other tissues/developmental stages there is a relatively low level of expression.

"Primary transformant" and "TO generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

The terms "protein," "peptide" and "polypeptide" are used interchangeably herein.

"Promoter" or "transcription regulating nucleotide sequence" refers to a nucleotide sequence, which controls the expression of a coding sequence by providing the recognition for RNA polymerase and other factors required for proper transcription. "Promoter regulatory sequences" can comprise proximal and more distal upstream elements and/or downstream elements. Promoter regulatory sequences influence the transcription, RNA processing or stability, or translation of the associated coding sequence. Regulatory sequences include enhancers, untranslated leader sequences, introns, exons, and polyadenylation signal sequences. They include natural and synthetic sequences as well as sequences that can be a combination of synthetic and natural sequences. An "enhancer" is a nucleotide sequence that can stimulate promoter activity and can be an innate element of the promoter or a heterologous element inserted to enhance the level or tissue specificity of a promoter. The primary sequence can be present on either strand of a double-stranded DNA molecule, and is capable of functioning even when placed either upstream or downstream from the promoter. The meaning of the term "promoter" includes "promoter regulatory sequences."

"Reference sequence" as used herein is defined as a sequence that is used as a basis for sequence comparison. A reference sequence may be a subset or the entirety of a specified sequence; for example, as a fragment of a full-length cDNA or gene sequence, or the full-length cDNA or gene sequence.

"Regulated promoter" refers to promoters that direct gene expression not constitutively, but in a temporally- and/or spatially-regulated manner, and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translational enhancer sequences, introns, and polyadenylation signal sequences. They include natural and synthetic sequences as well as sequences which may be a combination of synthetic and natural sequences.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived by posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA. A "functional RNA" refers to an antisense RNA, ribozyme, or other RNA that is not translated, but participates in a reaction or process as an RNA.

"Intron" refers to an intervening section of DNA that occurs almost exclusively within a eukaryotic gene, but which is not translated to amino acid sequences in the gene product. The introns are removed from the pre-mature mRNA through a process called splicing, which joins the exons to form an mRNA. For purposes of the presently disclosed subject matter, the definition of the term "intron" includes modifications to the nucleotide sequence of an intron derived from a target gene.

"Exon" refers to a section of DNA that carries the coding sequence for a protein or part of it. Exons are separated by intervening, non-coding sequences (introns). For purposes of the presently disclosed subject matter, the definition of the term "exon" includes modifications to the nucleotide sequence of an exon derived from a target gene.

A "selectable marker gene" refers to a gene whose expression in a plant cell gives the cell a selective advantage. The selective advantage possessed by the cells transformed with the selectable marker gene may be due to their ability to grow in presence of a negative selective agent, such as an antibiotic or a herbicide, compared to the ability to grow of non-transformed cells. The selective advantage possessed by the transformed cells may also be due to their enhanced capacity, relative to non-transformed cells, to utilize an added compound as a nutrient, growth factor or energy source. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

"Specific expression" is the expression of gene products that is limited to one or a few plant tissues (spatial limitation) and/or to one or a few plant developmental stages (temporal limitation).

Substantially identical: the phrase "substantially identical," in the context of two nucleic acid or protein sequences, refers to two or more sequences or subsequences that have at least 60%, preferably 80%, more preferably 90, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In an especially preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Those of skill in the art understand that to avoid a high similarity to a reference sequence due to inclusion of gaps in the polynucleotide sequence a gap penalty is typically introduced and is subtracted from the number of matches.

Optimal alignment of sequences for comparison can be conducted, e.g., by the local homology algorithm of Smith & Waterman, 1981, Adv. Appl. Math. 2: 482, by the homology alignment algorithm of Needleman & Wunsch, 1970, J. Mol. Biol. 48: 443, by the search for similarity method of Pearson & Lipman, 1988, Proc. Nat'l. Acad. Sci. 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., 1990, J. Mol. Biol. 215: 403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive value threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative scoring residue alignments, or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, 1989, Proc. Natl. Acad. Sci. 89: 10915).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

For purposes of the present invention, comparison of nucleotide sequences for determination of percent sequence identity to the promoter sequences disclosed herein is preferably made using the BLASTN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Another indication that two nucleic acid sequences are substantially identical is that the two molecules hybridize to each other under stringent hybridization conditions. The phrase "hybridizing specifically to" refers to the binding, duplexing, or hybridizing of a molecule only to a particular nucleotide sequence under stringent hybridization conditions when that sequence is present in a complex mixture (e.g., total cellular) of DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes* part I chapter 2, "Overview of principles of hybridization and the strategy of nucleic acid probe assays", Elsevier, New York. Generally, high stringency hybridization and wash conditions are selected to be about 5° C. lower than the thermal melting point ($T_m$) for the specific sequence at a defined ionic strength and pH. Typically, under high stringency conditions a probe will hybridize to its target subsequence, but to no other sequences.

The $T_m$ is the temperature (under defined ionic strength and pH) at which 50% of the target sequence hybridizes to a perfectly matched probe. Very high stringency conditions are selected to be equal to the $T_m$ for a particular probe. An example of high stringency hybridization conditions for hybridization of complementary nucleic acids which have more than 100 complementary residues on a filter in a Southern or northern blot is 50% formamide with 1 mg of heparin at 42° C., with the hybridization being carried out overnight. An example of very high stringency wash conditions is 0.1 5M NaCl at 72° C. for about 15 minutes. An example of high stringency wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, for example, when a copy of a nucleic acid is created using the maximum codon degeneracy permitted by the genetic code.

Low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium. citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 0% formamide, 1 M NaCl, 1% SDS at 37° C., and a wash in 0.1×SSC at 60 to 65° C.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl Anal. Biochem. 138:267-284 (1984); TM 81.5° C.+16.6 (log M) +0.41 (% GC) −0.61 (% form) −500/L; where M is the molarity of monovalent cations, % GC is the percentage of guanosine and cytosine nucleotides in the DNA, % form is the percentage of formamide in the hybridization solution, and L is the length of the hybrid in base pairs. The TM is the temperature (under defined ionic strength and pH) at which 50% of a complementary target sequence hybridizes to a perfectly matched probe. T is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, high stringency conditions are selected to be about 19° C. lower than the thermal melting point ($T_m$) for the specific sequence and its complement at a defined ionic strength and pH. However, very high stringency conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual ($2^{nd}$ ed., Cold Spring Harbor Laboratory Press, Plainview, N.Y.).

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Tissue-specific promoter" refers to regulated promoters that are not expressed in all plant cells but only in one or more cell types in specific organs (such as leaves, roots or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Transactivating gene" refers to a gene encoding a transactivating protein. It can encode a transcription factor. It can be a natural gene, for example, a plant transcriptional activator, or a chimeric gene, for example, when plant regulatory sequences are operably-linked to the open reading frame of a transcription factor from another organism. "Transactivating genes" may be chromosomally integrated or transiently expressed. "Trans-activation" refers to switching on of gene by the expression of another (regulatory) gene in trans.

A "transcriptional cassette" will comprise in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source.

The "transcription initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

The term "transformation" refers to the transfer of a nucleic acid fragment into the genome of a host cell, resulting in genetically stable inheritance. "Transiently transformed" refers to cells in which transgenes and foreign DNA have been introduced (for example, by such methods as *Agrobacterium*-mediated transformation or biolistic bombardment), but not selected for stable maintenance. "Transient transformation" in the context of a polynucleotide is intended to mean that a polynucleotide is introduced into the plant and does not integrate into the genome of the plant.

"Stably transformed" refers to cells that have been selected and regenerated on a selection media following transformation.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

"Transient expression" refers to expression in cells in which a virus or a transgene is introduced by viral infection or by such methods as *Agrobacterium*-mediated transformation, electroporation, or biolistic bombardment, but not selected for its stable maintenance.

As used herein, "genetic component" or "gene components" refers to any nucleic acid sequence or genetic element which may also be a component or part of an expression construct. Examples of genetic components include, but are not limited to promoter regions, 5' untranslated leaders, introns, genes, 3' untranslated regions, translational or transcriptional enhancers and other regulatory sequences or sequences which affect transcription or translation of one or more nucleic acid sequences. A genetic component may be nucleotide sequences located upstream (5' non-coding sequences), within, or downstream (3' non-coding sequences) of a coding sequence, and which influence the transcription, RNA processing or stability, or translation of the associated coding sequence. They include natural and synthetic sequences as well as sequences, which may be a combination of synthetic and natural sequences.

The term "translational enhancer sequence" refers to that DNA sequence portion of a gene between the promoter and coding sequence that is transcribed into RNA and is present in the fully processed mRNA upstream (5') of the translation start codon. The translational enhancer sequence may affect processing of the primary transcript to mRNA, mRNA stability or translation efficiency.

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

"Visible marker" refers to a gene whose expression does not confer an advantage to a transformed cell but can be made detectable or visible. Examples of visible markers include but are not limited to β-glucuronidase (GUS), luciferase (LUC) and green fluorescent protein (GFP).

"Wild-type" refers to the normal gene, virus, or organism found in nature without any known mutation.

The term "plant" refers to any plant, particularly to agronomically useful plants (e.g. seed plants), and "plant cell" is a structural and physiological unit of the plant, which comprises a cell wall but may also refer to a protoplast. The plant cell may be in form of an isolated single cell or a cultured cell, or as a part of higher organized units such as for example, a plant tissue, or a plant organ differentiated into a structure that is present at any stage of a plant's development. The promoters and compositions described herein may be utilized in any plant. Examples of plants that may be utilized in contained embodiments herein include, but are not limited to, maize (corn), wheat, rice, barley, soybean, cotton, sorghum, beans in general, rape/canola, alfalfa, flax, sunflower, safflower, millet, rye, sugarcane, sugar beet, cocoa, tea, tropical sugar beet, *Brassica* spp., cotton, coffee, sweet potato, flax, peanut, clover; vegetables such as lettuce, tomato, cucurbits, cassava, potato, carrot, radish, pea, lentils, cabbage, cauliflower, broccoli, Brussel sprouts, peppers, and pineapple; tree fruits such as citrus, apples, pears, peaches, apricots, walnuts, avocado, banana, and coconut; and flowers such as orchids, carnations and roses. Other plants useful in the practice of the invention include perennial grasses, such as switchgrass, prairie grasses, Indiangrass, Big bluestem grass, miscanthus and the like. It is recognized that mixtures of plants can be used.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

The term "young plant leaf tissue" or "young plant leaf material" refers to leaf tissue that may be agro-infiltrated with a *agrobacterium* strain comprising a binary vector comprising an expression cassette using a agro-infiltration device wherein said expression cassette comprises at least one gene and the gene is transcribed transiently in said leaf tissue. The terms "young plant leaf tissue" and "young plant leaf material" are intended to be used to interchangeably refer to plant leaf tissue that is at maximum 25 days old assuming the plant is grown in conventional greenhouse or growth chamber conditions. It is understood that the plant could be grown in suboptimal conditions and young plant tissue that may be used in the methods as described herein from suboptimal grown plants could exceed the maximum of 25 days. The terms "young plant leaf tissue" or "young plant leaf material" may also refer to the first, second, third, fourth or fifth leaf of a plant. For example the first, second or third leaf of a mature maize plant would be considered "young plant leaf tissue" in practice of the embodiments described herein. In addition, for example, maize leaves at the V1-V6 stage of development would be considered "young plant tissue" in practice of the embodiments described herein as well as developmental equivalents of other monocot plants.

As used herein "Abaxial" refers to the underside of a plant leaf. The term "abaxial" is intended to include any portion of the underside of a plant leaf.

As used herein, an "agro-infiltration device" refers to any device that may be used to infiltrate a solution of *agrobacterium* into the underside of a leaf. The term "agro-infiltration device" is intended to encompass needleless syringes as described in the methods herein. The term "agro-infiltration device" may also refer to any device that may be used to infiltrate a solution of *agrobacterium* into the underside of a leaf by applying pressure to said solution and said solution enters the interstitial cellular space of the leaf.

Preferably a transcription regulating nucleotide sequence of the invention comprises at least one promoter sequence localized upstream of the transcription start of the respective gene and is capable of inducing transcription of downstream sequences. The transcription regulating nucleotide sequence may comprise the promoter sequence of said genes but may further comprise other elements such as the 5'-untranslated sequence, enhancer sequences, intron, exon, and/or even comprise intron and exons of the associated genomic gene.

Promoters can comprise several regions that play a role in function of the promoter. Some of these regions are modular, in other words they can be used in isolation to confer promoter activity or they can be assembled with other elements to construct new promoters. The first of these promoter regions lies immediately upstream of the coding sequence and forms the "core promoter region" containing consensus sequences, normally 20-70 base pairs immediately upstream of the coding sequence. The core promoter region typically contains a TATA box and often an initiator element as well as the initiation site. The precise length of the core promoter region is not fixed but is usually well recognizable. Such a region is normally present, with some variation, in most promoters. The core promoter region is often referred to as a minimal promoter region because it is functional on its own to promote a basal level of transcription.

The presence of the core promoter region defines a sequence as being a promoter: if the region is absent, the promoter is non-functional. The core region acts to attract the general transcription machinery to the promoter for transcription initiation. However, the core promoter region is typically not sufficient to provide promoter activity at a desired level. A series of regulatory sequences, often upstream of the core, constitute the remainder of the promoter. The regulatory sequences can determine expression level, the spatial and temporal pattern of expression and, for a subset of promoters, expression under inductive conditions (regulation by external factors such as light, temperature, chemicals and hormones). Regulatory sequences can be short regions of DNA sequence 6-100 base pairs that define the binding sites for trans-acting factors, such as transcription factors. Regulatory sequences can also be enhancers, longer regions of DNA sequence that can act from a distance from the core promoter region, sometimes over several kilobases from the core region. Regulatory sequence activity can be influenced by transacting factors including but not limited to general transcription machinery, transcription factors and chromatin assembly factors.

Herein the term “quantitative data” refers to any data that may be expressed as a quantity. For example, a quantity of enzyme expressed in plant per gram of plant tissue. Another example may be the number of cells transiently transfected with a reporter gene such as GUS, GFP or some other suitable reporter gene. Another example may be the number of gene copies transcribed as determined through PCR. The quantitative data does not have to be exact; herein this data will be referred to as “semi-quantitative”. For example one may determine that one plant produces more of a relevant protein than another plant visually by looking at for example, a Western Blot. Or, one may for example quickly determine the amount of starch produced by transiently expressing a gene involved in the starch synthesis pathway, simply by staining the transiently transfected tissue with iodine. The tissue with the darker staining would semi-quantitatively contain more starch than the lighter stained transfected or control tissue.

Herein the term “qualitative data” refers to any data that may be expressed in regards to quality. For example, the visualization on a Western Blot that a protein from transiently transfected plant tissue is being cleaved compared to full length protein would be considered qualitative data. Qualitative data could also be the presence or non-presence of a particular phenotype. For example, a transiently expressed xylanase in leaf tissue of plant may cause a chlorosis of the leaf tissue.

Herein the terms “predictive model”,-“transient predictive model”, “gene expression predictive model” refers to any correlation between transiently expressed gene, expression cassettes, and/or gene components and the respective performance in stable transgenic plant lines. For example, an expression cassette A wherein an amylase is operably-linked to a chloroplast targeting sequence and an expression cassette B wherein an amylase is operably-linked to a endoplasmic reticulum (ER) targeting sequence and all other genetic components are equal, the effects of gene targeting can be quickly compared transiently in leaf tissue in regards to the enzyme expression levels and a “predictive model” formulated for which targeting would perform best in stable transgenic lines. This may be achieved, for example, by: a) delivering expression cassette A and expression cassette B into separate plants through agro-infiltration of 7 day old leaf tissue; b) transiently expressing expression cassettes A and B in said leaf tissue; c) sample leaf tissue at 24, 48, or 72 hours; d) perform an amylase enzyme assay such as a Ceralpha assay (MEGAZYME, Ireland); e) collect quantitative data; and f) formulate a predictive model based on transient protein expression per gram of leaf tissue. In some embodiments the transient performance may not exactly match the performance of stable transgenics expressing the same gene, expression cassette or genetic component, however a trend may be seen. For example, Expression cassette A in the above example may produce 1 μg/g of leaf tissue of amylase and Expression cassette B in the above example may produce 10 μg/g and if one was to stably transform expression cassette A and B into stable transgenic maize lines the expression levels may be 5 μg/g and 50 μg/g respectfully maintaining the trend that was seen in the transient data. In another embodiment, transient data in leaf tissue may be predictive of how a gene, expression cassette or genetic component performs in other plant parts for example, seed, root or reproductive tissue. A predictive model in this scenario would indicate to one skilled in the art that targeting an amylase to the ER would be a better strategy than to the vacuole if one wants to produce large amounts of amylase in planta. Predictive models using the methods described herein are not limited to protein expression levels but may also be used for any quantitative or qualitative data derived from transiently expressed genes, expression cassettes or genetic components.

“Transient transfection” or “transiently transfected” herein means that the introduction of said heterologous DNA sequence is done without selection of transfected cells for stable incorporation of said heterologous DNA sequence into a plant chromosome. An expression cassette may be introduced into a plant part using an *Agrobacterium* strain capable of introducing foreign DNA into plant cells. Transient expression of a gene and/or expression cassette may be observed 1, 2, 3, 4, 5, 6, 7, 8, 9, 10, 11, 12, 13, 14, 15, 16, 17, 18, 19 or 20 or more days. Preferably, transient expression may be observed over 24 hours. More preferable transient expression may be observed over 48 hours. Most preferably, transient expression may be observed over 72 hours.

DETAILED DESCRIPTION OF THE INVENTION

Methods and compositions for transiently expressing genes, expression cassettes, or gene components are provided. The method comprises agro-infiltration of an binary vector comprising at least one expression cassette into a plant part (e.g., plant leaf), wherein the expression cassette contains at least one promoter operably-linked to a heterologous gene. The resulting plants of the current invention transiently express genes, expression cassettes or gene components in planta at expression levels sufficient in serving as a predictive model for how a respective gene, expression cassette or gene component operably will perform in stable transgenic plant lines. Further provided are methods of use in constructing predictive models for stable transgenic plant lines through comparative analysis of transient quantitative and qualitative data or a combination thereof.

Transgenic plants, seeds, plant tissues and plant parts are provided. It is recognized that the process may be controlled by the use of constitutive, tissue, temporal or chemically regulated promoters. The following embodiments can be carried out in either monocotyledon or dicotyledonous plants.

In the process of the invention, a gene, expression cassette and/or genetic component is expressed transiently in plant parts or more preferably plant leaves. Gene expression, promoter performance, gene activity, protein function and form are a few examples of what can be evaluated in transient expression cassettes and serve as a predictive model of how a certain expression cassette configuration, gene and/or genetic component may perform in stably transgenic plant lines. A method to transiently express genes, expression cassettes, or gene components in planta may be desirable across multiple industries for example but not limited to commercial agriculture, ethanol, animal feed, plastics, chemicals, medical and other industrial applications.

The methods of the invention find use in the integration of current practices for the cultivation of crop plants for the purpose of obtaining a commercially desired stable transgenic plant line optimally expressing a gene of interest. The ability to quickly evaluate gene performance, expression cassette configuration and effects of genetic components on expression performance is encompassed in the current invention. The methods of the invention may reduce the time, resources and space needed to evaluate genes, expression cassettes or gene components compared to the conventional means of generating stable transgenic plant lines and performing the same evaluations in the corresponding stable transgenic plant part or parts. In one embodiment, the invention may reduce evaluation time in the selection of optimal gene expression in stable transgenic plants by 6-12 months as well as quickly allow for the selection of the best expression cassette configuration for gene expression. In another embodiment, the invention may reduce evaluation time in the selection of optimal gene expression in stable transgenic plants by 12-24 months or more. In some embodiments, the invention may reduce evaluation time in the selection of optimal gene expression in stable transgenic plants by 1-12 months or more.

In one embodiment, the methods described herein may be employed in any plant. More preferably the methods described herein may be employed in crop plants. Another aspect of the methods described herein, is that an expression cassette and its relevant gene components can be transiently expressed in any plant part as described. More preferably, an expression cassette may be transiently expressed in photosynthetic plant material. Most preferable, is that the current methods may be employed to transiently express an expression cassette, gene, and/or genetic component in plant leaf tissue. Yet another aspect of the invention is that agro-infiltration of expression cassettes described herein transiently transfected into 1,2,3,4,5,6,7,8,9,10,11,12,13,14,15,16, 17, 18, 19 or 20 or more days old leaf tissue will result in a transient expression of said expression cassette in a manner where qualitative and/or quantitative data can be collected through procedures well known in the art, that can further be predictive of how said expression cassette will perform in stable transgenic lines transformed with said expression cassette or corresponding genetic components. In a preferred embodiment 7 day old maize leaf tissue is agro-infiltrated with the expression cassette and genetic components as described herein.

In a preferred embodiment of the invention the plant part is agro-infiltrated into leaf tissue wherein a solution of Agrobacteria transformed with the expression cassette of interest is infiltrated into the interstitial space of the plant tissue (e.g. leaf tissue). It is also understood that the invention may be performed using biolistics or any other transformation technology known by those skilled in the relevant art or described herein.

In one embodiment of the invention the young plant leaf tissue is from maize and the maize leaf tissue is at a maximum leaf age of about V1 to about V6 or about 2 months old wherein the maize plant was grown in conventional greenhouse and/or growth chamber conditions. In another embodiment the maize young leaf tissue is leaf 1 of a maize plant that is about a maximum of about 20 to about 30 days old. It is understood that maize plants grown in suboptimum conditions could comprise young leaf tissue that may be utilized in embodiments as described herein wherein the maize plant age exceeds 30, 40, 50, 60 or 70 days old.

Preferred maize genotypes that may be used with the invention may be but are not limited to AX5707 and FF6096 for example. Preferred rice genotypes that may be used with the invention may be but are not limited to Nipponbare Rice 198. Preferred sorghum genotypes that may be used with the invention may be but are not limited to brandes, della and dale. Preferred wheat genotypes that may be used with the invention in some embodiments may be but are not limited to A C Nanda, TLAXCALA F2000, CALINGIRI, OMSKAYA 33, Catalido. Preferred oat genotypes that may be used with the invention may be but are not limited to SSC-31-913200 whole oats.

In one embodiment of the invention the young plant leaf tissue is from sugarcane and the sugarcane leaf tissue is at a maximum leaf age of about 7 to 12 days old wherein the sugarcane plant was grown in conventional greenhouse and/or growth chamber conditions. In another embodiment the sugarcane young leaf tissue is leaf 1 of a sugarcane plant that is about a maximum of about 20 to about 30 days old. It is understood that sugarcane plants grown in suboptimum conditions could comprise young leaf tissue that may be utilized in embodiments as described herein wherein the sugarcane plant age exceeds 30, 40, 50, 60 or 70 days old.

In another embodiment of the invention the young plant leaf tissue is from sorghum and the sorghum leaf tissue is at a maximum leaf age of about 20 days old wherein the sorghum plant was grown in conventional greenhouse and/or growth chamber conditions. In another embodiment the sorghum young leaf tissue is leaf 1 of a sugarcane plant that is about a maximum of about 20 to about 30 days old. It is understood that sorghum plants grown in suboptimum conditions could comprise young leaf tissue that may be utilized in embodiments as described herein wherein the sorghum plant age exceeds 30, 40, 50, 60 or 70 days old.

In yet another embodiment of the invention the young plant leaf tissue is from rice and the rice leaf tissue is at a maximum leaf age of about 40 days old wherein the rice plant was grown in conventional greenhouse and/or growth chamber conditions. In another embodiment the rice young leaf tissue is leaf 1 of a rice plant that is about a maximum of about 20 to about 30 days old. It is understood that rice plants grown in suboptimum conditions could comprise young leaf tissue that may be utilized in embodiments as described herein wherein the rice plant age exceeds 30, 40, 50, 60 or 70 days old.

In yet another embodiment of the invention the young plant leaf tissue is from a grass and the grass leaf tissue is at a maximum leaf age of about 30 days old wherein the grass was grown in conventional greenhouse and/or growth chamber conditions. In another embodiment the grass young leaf tissue is leaf 1 of a grass that is about a maximum of about 20 to about 30 days old.

In one embodiment of the invention translational or transcriptional enhancers may be used to increase transient protein expression. In a preferred embodiment an enhancer region from the Figwort Mosaic Virus (eFMV) may be used. In another preferred embodiment the Figwort Mosaic Virus (eFMV) enhancer is used in combination with a 35s cauliflower mosaic virus enhancer for increased expression of a gene in transient and/or stably transformed plants.

One aspect of the invention is that there is no size limitation on the gene that is being transiently expressed in contrast with viral transient transfection methods. Viral transient transfection systems are limited in the size of the gene that can be transfected into a plant cell. In one embodiment of the invention the heterologous gene being introduced through agro-infiltration may be greater than 0.1, 0.5, 0.75, 1.0, 2.0, 3.0, 4.0, 5.0, 6.0, 7.0, 8.0, 9.0 or 10.0 kilobases.

The methods described herein may be useful in evaluating processing enzymes expressed in planta. For example, the relevant processing enzyme may be evaluated quantitatively or qualitatively by transiently expressing the processing enzyme in plant tissue as described in the methods herein. Suitable "processing enzymes" include, but are not limited to, starch degrading or isomerizing enzymes including, for example, α-amylase, endo or exo-1,4, or 1,6-α-D, glucoamylase, glucose isomerase, β-amylases, α-glucosidases, and other exo-amylases; and starch debranching enzymes, such as isoamylase, pullulanase, neo-pullulanase, iso-pullulanase, amylopullulanase and the like, glycosyl transferases such as cyclodextrin glycosyltransferase and the like, cellulases such as exo-1,4-β-cellobiohydrolase, exo-1,3-O-D-glucanase, hemicellulase, β-glucosidase and the like; endoglucanases such as endo-1,3-β-glucanase and endo-1,4-β-glucanase and the like; L-arabinases, such as endo-1,5-α-L-arabinase, α-arabinosidases and the like; galactanases such as endo-1,4-β-D-galactanase, endo-1,3-β-D-galactanase, 1-galactosidase, α-galactosidase and the like; mannanases, such as endo-1,4-β-D-mannanase, β-mannosidase, α-mannosidase and the like; xylanases, such as endo-1,4-1-xylanase, β-D-xylosidase, 1,3-β-D-xylanase, and the like; and pectinases; and non-starch processing enzymes, including protease, glucanase, xylanase, thioredoxin/thioredoxin reductase, esterase, phytase, and lipase. In one aspect of the invention, a processing enzyme may be evaluated and a transient predictive model formulated based on measurements of the processing enzyme and respective substrate's reactive by-product. For example, one skilled in the art may use the methods described herein to transiently express an amylase in plant, bring the amylase in contact with a substrate and measure the amount of maltodextrins released using HPLC or other methods known by those skilled in the art. The substrate may be present in planta or the transiently expressed enzyme may be isolated and brought in contact in situ with its relevant substrate. One may also evaluate combination of enzymes on a substrate (e.g. starch or cellulose) using the methods described herein.

Plant Expression Cassettes

The compositions of the invention may contain nucleic acid sequences for transient or stable transformation and expression in a plant of interest. The nucleic acid sequences may be present in DNA constructs or expression cassettes. An expression cassette under the previous definition may be a nucleic acid molecule capable of directing expression of a particular nucleotide sequence in an appropriate host cell, comprising a promoter operably linked to the nucleotide sequence of interest (e.g., a nucleotide sequence encoding a processing enzyme) which is operably linked to termination signals. Expression cassettes also typically comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The present invention encompasses the transformation of plants with expression cassettes capable of transiently expressing polynucleotides. In representative embodiments, the expression cassette will include in the 5'-3' direction of transcription, a transcriptional and translational initiation region (i.e., a promoter) and a polynucleotide of interest, and genetic components (i.e. translational enhancers). The expression cassette may optionally comprise a transcriptional and translational termination region (i.e. termination region) functional in plants. Expression cassettes of the invention may also comprise a leader sequence and/or a sequence allowing for inducible expression of the polynucleotide of interest. See, Guo et al. (2003) *Plant J.* 34:383-92 and Chen et al. (2003) *Plant J.* 36:731-40 for examples of sequences allowing for inducible expression. The regulatory sequences of the expression construct are operably linked to the polynucleotide of interest.

Any promoter capable of driving expression in the plant of interest may be used in the practice of the invention. In one embodiment, a non-leaf preferred and/or non-leaf specific promoter may be evaluated quantitatively and/or qualitatively and a predictive model formulated to predict how a promoter will perform in its respective preferred and/or specific tissue. For example, a seed specific promoter may be evaluated transiently in leaf tissue using methods described herein. Several tissue-specific regulated genes and/or promoters have been reported in plants. Some reported tissue-specific genes include the genes encoding the seed storage proteins (such as napin, cruciferin, beta-conglycinin, and phaseolin), zein or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4, see, for example, EP 255378 and Kridl et al., Seed Science Research, 1:209 (1991)). Examples of tissue-specific promoters, which have been described include the lectin (Vodkin, Prog. Clin. Biol. Res., 138;87 (1983); Lindstromet al., Der. Genet., 11:160 (1990)), corn alcohol dehydrogenase 1 (Vogel et al., 1989; Dennis et al., Nucleic Acids Res., 12:3983 (1984)), corn light harvesting complex (Simpson, 1986; Bansal et al., Proc. Natl. Acad. Sci. USA, 89:3654 (1992)), corn heat shock protein (Odell et al., 1985; Rochester et al., 1986), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (vanTunen et al., EMBO J., 7;1257(1988)), bean glycine rich protein 1 (Keller et al., Genes Dev., 3:1639 (1989)), truncated CaMV 35s (Odell et al., Nature, 313:810 (1985)), potato patatin (Wenzler et al., Plant Mol. Biol., 13:347 (1989)), root cell (Yamamoto et al., Nucleic Acids Res., 18:7449 (1990)), maize zein (Reina et al., Nucleic Acids Res., 18:6425 (1990); Kriz et al., Mol. Gen. Genet., 207:90 (1987); Wandelt et al., Nucleic Acids Res., 17:2354 (1989); Langridge et al., Cell, 34:1015 (1983); Reina et al., Nucleic Acids Res., 18:7449 (1990)), globulin-1 (Belanger et al., Genetics, 129:863 (1991)), α-tubulin, cab (Sullivan et al., Mol. Gen. Genet., 215:431 (1989)), PEPCase (Hudspeth & Grula, 1989), R gene complex-associated promoters (Chandler et al., Plant Cell, 1:1175 (1989)), and chalcone synthase promoters (Franken et al., EMBO J., 10:2605 (1991)). Particularly useful for seed-specific expression is the pea vicilin promoter (Czako et al., Mol. Gen. Genet., 235:33 (1992). (See also U.S. Pat. No. 5,625,136, herein incorporated by reference.) Other useful promoters for expression in mature leaves are those that are switched on at the onset of senescence, such as the SAG promoter from *Arabidopsis* (Gan et al., Science, 270:1986 (1995). The promoter may be native or analogous or foreign or heterologous to the plant host.

Transient predictive models formulated by the methods described herein can evaluate promoters based upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence. The methods described herein allow for the fast evaluation of promoter selection and positioning.

Some suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. It is understood that some promoters that show preferential targeting of expression in target tissues may also exhibit "leaky" expression in non-preferential targeted tissues. One example may be a promoter whose expression profile shows preferential expression in maize seed, but also exhibits strong expression in mature leaf tissue. Methods for identifying and characterizing promoter regions in plant genomic DNA include, for example, those described in the following references: Jordano, et al., Plant Cell, 1:855-866 (1989); Bustos, et al., Plant Cell, 1:839-854 (1989); Green, et al., EMBO J. 7, 4035-4044 (1988); Meier, et al., Plant Cell, 3, 309-316 (1991); and Zhang, et al., Plant Physiology 110: 1069-1079 (1996). A number of plant promoters have been described with various expression characteristics. Examples of some constitutive promoters which have been described include the rice actin 1 (Wang et al., Mol. Cell. Biol., 12:3399 (1992); U.S. Pat. No. 5,641,876), CaMV .sup.35S (Odell et al., Nature, 313:810 (1985)), CaMV 19S (Lawton et al., 1987), nos (Ebert et al., 1987), Adh (Walker et al., 1987), sucrose synthase (Yang & Russell, 1990), and the ubiquitin promoters.

Promoters active in photosynthetic tissue in order to drive transcription in green tissues such as leaves and stems may be of interest in the present invention. Examples of such promoters include the ribulose-1,5-bisphosphate carboxylase (RbcS) promoters such as the RbcS promoter from eastern larch (*Larix laricina*), the pine cab6 promoter (Yamamoto et al. (1994) Plant Cell Physiol. 35:773-778), the Cab-1 gene promoter from wheat (Fejes et al. (1 990) Plant Mol. Biol. 15:921-932), the CAB-1 promoter from spinach (Lubberstedt et al. (1994) Plant Physiol. 104:997-1006), the cab1R promoter from rice (Luan et al. (1992) Plant Cell 4:971-981), the pyruvate orthophosphate dikinase (PPDK) promoter from maize (Matsuoka et al. (1993) Proc Natl Acad Sci USA 90:9586-9590), the tobacco Lhcb1*2 promoter (Cerdan et al. (1997) Plant Mol. Biol. 33:245-255), the *Arabidopsis thaliana* SUC2 sucrose-H+ symporter promoter (Truernit et al. (1995) Planta 196:564-570), and thylakoid membrane protein promoters from spinach (psaD, psaF, psaE, PC, FNR, atpC, atpD, cab, rbcS). Other promoters that drive transcription in stems, leaves and green tissue are described in U.S. Patent Publication No. 2007/0006346, herein incorporated by reference in its entirety. In some embodiments of the invention, promoters active in photosynthetic tissue may be transiently evaluated and predictive models formulated.

In some other embodiments of the present invention, evaluation of inducible promoters may be desired. Inducible promoters drive transcription in response to external stimuli such as chemical agents or environmental stimuli. For example, inducible promoters can confer transcription in response to hormones such as gibberellic acid or ethylene, or in response to light or drought. Several inducible promoters have been reported. Many are described in a review by Gatz, in Current Opinion in Biotechnology, 7:168 (1996) and Gatz, C., Annu. Rev. Plant Physiol. Plant Mol. Biol., 48:89 (1997). Examples include tetracycline repressor system, Lac repressor system, copper-inducible systems, salicylate-inducible systems (such as the PR 1 a system), glucocorticoid-inducible (Aoyama T. et al., N-H Plant Journal, 11:605 (1997)) and ecdysone-inducible systems. Other inducible promoters include ABA- and turgor-inducible promoters, the promoter of the auxin-binding protein gene (Schwob et al., Plant J., 4:423 (1993)), the UDP glucose flavonoid glycosyl-transferase gene promoter (Ralston et al., Genetics, 119:185 (1988)), the MPI proteinase inhibitor promoter (Cordero et al., Plant J., 6:141 (1994)), and the glyceraldehyde-3-phosphate dehydrogenase gene promoter (Kohler et al., Plant Mol. Biol., 29;1293 (1995); Quigley et al., J. Mol. Evol., 29:412 (1989); Martinez et al., J. Mol. Biol., 208:551 (1989)). Also included are the benzene sulphonamide-inducible (U.S. Pat. No. 5364,780) and alcohol-inducible (WO 97/06269 and WO 97/06268) systems and glutathione S-transferase promoters. Other studies have focused on genes inducibly regulated in response to environmental stress or stimuli such as increased salinity, drought, pathogen and wounding. (Graham et al., J. Biol. Chem., 260: 6555 (1985); Graham et al., J. Biol. Chem., 260:6561 (1985), Smith et al., Planta, 168:94 (1986)). Accumulation of metallocarboxypeptidase-inhibitor protein has been reported in leaves of wounded potato plants (Graham et al., Biochem. Biophys. Res. Comm., 101:1164 (1981)). Other plant genes have been reported to be induced by methyl jasmonate, elicitors, heat-shock, anaerobic stress, or herbicide safeners. Regulated expression of a chimeric transacting viral replication protein can be further regulated by other genetic strategies, such as, for example, Cre-mediated gene activation (Odell et al. Mol. Gen. Genet., 113:369 (1990)). Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of tissue- and developmental-specific or inducible promoters. An alternate genetic strategy is the use of a tRNA suppressor gene. For example, the regulated expression of a tRNA suppressor gene can conditionally control expression of a trans-acting replication protein coding sequence containing an appropriate termination codon (Ulmasov et al. Plant Mol. Biol., 35:417 (1997)). Again, either the chimeric tRNA suppressor gene, the chimeric transacting replication gene, or both can be under the control of tissue- and developmental-specific or inducible promoters. Preferably, in the case of a multicellular organism, the promoter can also be specific to a particular tissue, organ or stage of development. Examples of such promoters include, but are not limited to, the *Zea mays* ADP-gpp and the *Zea mays* γ-zein promoter and the *Zea mays* globulin promoter. One embodiment of the invention may be a fast way to evaluate inducible promoter performance on the expression of a gene of interest in stable line transgenics by formulating predictive models from quantitative and/or qualitative data derived from transient expression using the methods described herein.

Transient expression of a gene in a plant part may be desired only in a certain time period during the development of the plant. Developmental timing is frequently correlated with tissue specific gene expression. For example, expression of zein storage proteins is initiated in the endosperm about 15 days after pollination.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used. One embodiment of the invention may be a fast way to evaluate the effects of terminator sequences on the expression of a gene of interest in stable line transgenics by formulating predictive models from quantitative and/or qualitative data derived from transient expression using the methods described herein.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183-1200 (1987)). In the same experimental system, the intron from the maize bronze 1 gene had a similar effect in enhancing expression. Intron sequences have been routinely incorporated into plant transformation vectors, typically within the non-translated leader.

A number of non-translated leader sequences derived from viruses are also known to enhance expression. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); human immunoglobulin heavy-chain binding protein (BiP) leader, (Macejak, D. G., and Samow, P., Nature 353: 90-94 (1991)); untranslated leader from the coat protein mRNA of alfalfa mosaic virus (AMV RNA 4), (Jobling, S. A., and Gehrke, L., Nature 325:622-625 (1987)); tobacco mosaic virus leader (TMV), (Gallie, D. R. et al., Molecular Biology of RNA, pages 237-256 (1989)); and Maize Chlorotic Mottle Virus leader (MCMV) (Lommel, S. A. et al., Virology 81:382-385 (1991)). See also, Della-Cioppa et al., Plant Physiology 84:965-968 (1987). One embodiment of the invention may be a fast way to evaluate the effects of enhancer or genetic component sequences on the expression of a gene of interest in stable line transgenics by formulating predictive models from quantitative and/or qualitative data derived from transient expression using the methods described herein.

The methods described herein may be used to formulate predictive models of the effects of gene targeting and protein expression. Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (19-88)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different from that of the promoter from which the targeting signal derives.

In order to ensure the localization in the plastids it is conceivable to use one of the following transit peptides: the plastidic Ferredoxin: NADP+ oxidoreductase (FNR) of spinach which is disclosed in Jansen et al. (Current Genetics 13 (1988), 517-522). In particular, the sequence ranging from the nucleotides −171 to 165 of the cDNA sequence disclosed therein can be used, which comprises the 5' non-translated region as well as the sequence encoding the transit peptide. Another example is the transit peptide of the waxy protein of maize including the first 34 amino acid residues of the mature waxy protein (Klosgen et al., Mol. Gen. Genet. 217 (1989), 155-161). It is also possible to use this transit peptide without the first 34 amino acids of the mature protein. Furthermore, the signal peptides of the ribulose bisphosphate carboxylase small subunit (Wolter et al., Proc. Natl. Acad. Sci. USA 85 (1988), 846-850; Nawrath et al., Proc. Natl. Acad. Sci. USA 91 (1994), 12760-12764), of the NADP malate dehydrogenase (Galiardo et al., Planta 197 (1995), 324-332), of the glutathione reductase (Creissen et al., Plant J. 8 (1995), 167-175) or of the R1 protein Lorberth et al. (Nature Biotechnology 16, (1998), 473-477) can be used.

In one aspect of the invention, suppressors of gene silencing may be included within the expression cassette to increase gene expression. It is known in the art that the inclusion of such gene silencing suppressors can increase transient gene expression in dicots (see for example, Voinnet et al., 2003, *Plant J.,* 33, 549-556).

There is no preconceived limitation to the types of proteins that can be used in the invention described herein.

In one aspect, the methods are practiced with nucleic acid sequences encoding desired proteins, wherein the nucleic acid sequences are designed to provide codons preferred by the plant being used for transient transformation. The characteristics of codon usage for several plants are available and are described in Wada et al., "Codon Usage Tabulated From the GenBank Genetic Sequence Data, "*Nucleic Acids Research* 19: 1981-1986 (1991).

In one aspect it is not necessary for the expression cassette to contain a selectable marker and/or it is not required that the DNA construct be devoid of tumor inducing genes.

In some embodiments, selectable markers may be used in the present invention to allow for the selection of transiently transformed plants and plant tissue. One may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can select for by chemical means, i.e., through the use of a selective agent (e.g., a herbicide, antibiotic, or the like), or whether it is simply a trait that one can identify through observation or testing, i.e., by screening (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transiently transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel et al., The Plant Cell, 2:785 (1990)) molecule is well characterized in terms of molecular biology, expression and protein structure. However, any one of a variety of extensins and/or glycine-rich wall proteins (Keller et al., EMBO Journal, 8:1309 (1989)) could be modified by the addition of an antigenic site to create a screenable marker.

a. Selectable Markers

Possible selectable markers for use in connection with the present invention include, but are not limited to, a neo or nptll gene (Potrykus et al., Mol. Gen. Genet., 199:183 (1985)) which codes for kanamycin resistance and can be selected for using kanamycin, G418, and the like; a bar gene which confers resistance to the herbicide phosphinothricin; a gene which encodes an altered EPSP synthase protein (Hinchee et al., Biotech., 6:915 (1988)) thus conferring glyphosate resistance; a nitrilase gene such as bxn from *Klebsiella ozaenae* which confers resistance to bromoxynil (Stalker et al., Science, 242:419 (1988)); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., J. Biol. Chem., 263:12500 (1988)); a dalapon dehalogenase gene that confers resistance to the herbicide dalapon; a phosphomannose isomerase (PMI) gene; a mutated anthranilate synthase gene that confers resistance to 5-methyl tryptophan; the hph gene which confers resistance to the antibiotic hygromycin; or the mannose-6-phosphate isomerase gene (also referred to herein as the phosphomannose isomerase gene), which provides the ability to metabolize mannose (U.S. Pat. Nos. 5,767,378 and 5,994,629). One skilled in the art is capable of selecting a suitable selectable marker gene for use in the present invention. Where a mutant EPSP synthase gene is employed, additional benefit may be realized through the incorporation of a suitable chloroplast transit peptide, CTP (European Patent Application 0,218,571, 1987).

An illustrative embodiment of a selectable marker gene capable of being used in systems to select transformants are the genes that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., Mol. Gen. Genet., 205:42 (1986); Twell et al., Plant Physiol., 91:1270 (1989)) causing rapid accumulation of ammonia and cell death. The success in using this selective system in conjunction with monocots was particularly surprising because of the major difficulties which have been reported in transformation of cereals (Potrykus, Trends Biotech., 7:269 (1989)).

Where one desires to employ a bialaphos resistance gene in the practice of the invention, a particularly useful gene for this purpose is the bar or pat genes obtainable from species of *Streptomyces* (e.g., ATCC No. 21,705). The cloning of the bar gene has been described (Murakami et al., Mol. Gen. Genet., 205:42 (1986); Thompson et al., EMBO Journal, 6:2519 (1987)) as has the use of the bar gene in the context of plants other than monocots (De Block et al., EMBO Journal, 6:2513 (1987); De Block et al., Plant Physiol., 91:694 (1989)).

b. Screenable Markers

Screenable markers that may be employed include, but are not limited to, a glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., in Chromosome Structure and Function, pp. 263-282 (1988)); a β-lactamase gene (Sutcliffe, PNAS USA, 75:3737 (1978)), which encodes an enzyme for which various chromogenic substrates are known (e.g., PADAC, a chromogenic cephalosporin); a xylE gene (Zukowsky et al., PNAS USA, 80:1101 (1983)) which encodes a catechol dioxygenase that can convert chromogenic catechols; an α-amylase gene (Ikuta et al., Biotech., 8:241 (1990)); a tyrosinase gene (Katz et al., J. Gen. Microbiol., 129:2703 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., Science, 234:856 (1986)), which allows for bioluminescence detection; or an aequorin gene (Prasher et al., Biochem. Biophys. Res. Comm., 126:1259 (1985)), which may be employed in calcium-sensitive bioluminescence detection, or a green fluorescent protein gene (Niedz et al., Plant Cell Reports, 14: 403 (1995)).

Genes from the maize R gene complex are contemplated to be particularly useful as screenable markers. The R gene complex in maize encodes a protein that acts to regulate the production of anthocyanin pigments in most seed and plant tissue. A gene from the R gene complex is suitable for maize transformation, because the expression of this gene in transformed cells does not harm the cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together. A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

The polynucleotides used to transform the plant may include, but is not limited to, DNA from plant genes and non-plant genes such as those from bacteria, yeasts, animals or viruses. The introduced DNA can include modified genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of the untransformed plant.

In one embodiment of the invention, a transient predictive model may be formulated to evaluate the effects of gene inhibition. The terms "inhibit," "inhibition," "down-regulation" and "inhibiting" as used herein refers to any decrease in the expression or function of a target gene product, including any relative decrement in expression or function up to and including complete abrogation of expression or function of the target gene product.

Inhibition of expression or function of a target gene product (i.e., a gene product of interest) can be in the context of a comparison between any two plants, for example, expression or function of a target gene product in a genetically altered plant versus the expression or function of that target gene product in a corresponding wild-type plant. Alternatively, inhibition of expression or function of the target gene product can be in the context of a comparison between plant cells, organelles, organs, tissues, or plant parts within the same plant or between plants, and includes comparisons between developmental or temporal stages within the same plant or between plants.

Methods for inhibiting or eliminating the expression of a gene in a plant are well known in the art, and any such method may be used in the methods of the present invention. Antisense constructions, complementary to at least a portion of the messenger RNA (mRNA) for the target sequence can be utilized. Antisense nucleotides are constructed to hybridize with the corresponding mRNA. Modifications of the antisense sequences may be made as long as the sequences hybridize to and interfere with expression of the corresponding mRNA. In this manner, antisense constructs having at least about 70%, at least about 80%, at least about 85% or higher sequence identity to the corresponding sense sequences may be used. Furthermore, portions of the antisense nucleotides may be used to disrupt the expression of the target gene. Generally, sequences of at least about 10 nucleotides, at least about 20 nucleotides, at least about 30 nucleotides, at least about 40 nucleotides, at least about 50 nucleotides, at least about 100 nucleotides, at least about 200 nucleotides, at least about 300, at least about 400, at least about 450, at least about 500, at least about 550, or greater may be used. Antisense methods are known in the art, See, for example, Sheehy et al. (1988) *Proc. Natl. Acad. Sci. USA* 85:8805-8809; and U.S. Pat. Nos. 5,107,065; 5,453,566; and 5,759,829); herein incorporated by reference.

Cosuppression may also be used to suppress the expression of the target gene.

In this manner, a heterologous gene sequence is expressed in a plant of interest in the sense orientation to suppress the expression of the endogenous gene in the plant. Methods for cosuppression are known in the art. See, for example, Taylor (1997) *Plant Cell* 9:1245; Jorgensen (1990) *Trends Biotech.* 8(12):340-344; Jorgensen et al. (1996) *Plant Mol. Biol.* 31:957-973; Johansen and Carrington (2001) *Plant Physiol.* 126:930-938; Broin et al. (2002) *Plant Cell* 14:1417-1432; Stoutjesdijk et al (2002) *Plant Physiol.* 129:1723-1731; Yu et al. (2003) *Phytochemistry* 63:753-763; Flavell (1994) *Proc. Natl. Acad. Sci. USA* 91:3490-3496; Finnegan et al. (1994) *Bio/Technology* 12:883-888; Neuhuber et al. (1994) *Mol. Gen. Genet.* 244:230-241; and U.S. Pat. Nos. 5,034,323, 5,283,184, and 5,942,657; all of which are herein incorporated by reference.

Cosuppression involves transforming plants with a DNA construct comprising a promoter that drives expression in a plant operably linked to at least a portion of a polynucleotide that corresponds to the transcript of the gene of interest or the target gene. The nucleotide sequence is constructed or chosen to have substantial sequence identity to the sequence of the transcript of the endogenous gene, typically greater than about 60% sequence identity, more typically greater than about 80% sequence identity, more typically greater than about 90% sequence identity, and in some instances greater than about 95% sequence identity.

RNA interference (RNAi) can also be used to down-regulate genes. See, generally, Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *Proc. Natl. Acad. Sci. USA* 95:15502-15507. In RNAi, long double-stranded RNAs (dsRNAs), typically >200 nucleotides, can be used to silence the expression of a target gene in a plant. Upon introduction, the long dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme. These siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA. Cleavage of cognate RNA takes place near the middle of the region bound by the siRNA strand.

In this manner, double-stranded RNA (dsRNA) interference may be used. For dsRNA interference, a sense and an antisense RNA molecule that is fully or partially complementary to the sense RNA molecule are expressed in the same cell, resulting in inhibition of the expression of the corresponding endogenous messenger RNA.

The sense and antisense molecules can be expressed from a single or separate expression cassette. Alternatively, multiple plant lines transformed with the dsRNA interference expression cassette or expression cassettes are then screened to identify plant lines that show the greatest inhibition of gene expression. Methods for using dsRNA interference to inhibit the expression of endogenous plant genes are described in Waterhouse et al. (1998) *Proc. Natl. Acad. Sci. USA* 95:13959-13964, Liu et al. (2002) *Plant Physiol.* 129:1732-1743, and WO 99/49029, WO 99/53050, WO 99/61631, and WO 00/49035; each of which is herein incorporated by reference.

In some embodiments of the invention, inhibition of the expression of a gene may be obtained by hairpin RNA (hpRNA) interference or intron-containing hairpin RNA (ihpRNA) interference. A short hairpin RNA (shpRNA) is a sequence of RNA that makes a tight hairpin turn that can be used to silence gene expression. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk et al. (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

Interfering hairpin RNA (ihpRNA) may also be used in the methods of the invention. ihpRNA have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, thus increasing the efficiency of interference. See, for example, Smith et al. (2000) *Nature* 407:319-320. Methods for using ihpRNA interference to inhibit the expression of endogenous plant genes are described, for example, in Smith et al. (2000) *Nature* 407:319-320; Wesley et al. (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference. See also WO 02/00904 where the hpRNA is designed such that the loop region determines the specificity of the RNA interference.

In some embodiments of the invention, RNA interference by transient expression of a gene encoding a micro RNA (miRNA) may be used. miRNAs are regulatory agents consisting of about 22 ribonucleotides. miRNA are highly efficient at inhibiting the expression of endogenous genes. See, for example Javier et al. (2003) *Nature* 425: 257-263, herein incorporated by reference. For miRNA interference, the expression cassette is designed to express an RNA molecule that is modeled on an endogenous miRNA gene. The miRNA gene encodes an RNA that forms a hairpin structure containing about a 22-nucleotide sequence that is complementary to the target transcript. For example, a 22-nucleotide sequence is selected from a target transcript sequence and contains 22 nucleotides of said target sequence in sense orientation and 22 nucleotides of a corresponding antisense sequence that is complementary to the sense sequence.

Other methods for down-regulating the activity of a target protein include virus-induced gene silencing (Burton et al. (2000) *Plant Cell* 12:691-705; and Baulcombe (1999) *Curr. Op. Plant Bio.* 2:109-113); ribozymes (Steinecke et al. (1992) *EMBO J.* 11:1525; and Perriman et al. (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes et al. (1999) *Trends Plant Sci.* 4:90-96; Dharmapuri and Sonti (1999) *FEMS Microbiol. Lett.* 179:53-59; Meissner et al. (2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-96; Fitzmaurice et al. (1999) *Genetics* 153:1919-1928; Bensen et al. (1995) *Plant Cell* 7:75-84; Mena et al. (1996) *Science* 274:1537-1540; and U.S. Pat. No. 5,962,764); each of which is herein incorporated by reference.

Furthermore, nucleic acid molecules encoding antibodies specifically recognizing proteins, or homologs thereof, according to the invention in a plant cell, i.e. specific fragments or epitopes of such a protein, can be used for inhibiting the activity of this protein. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Kohler and Milstein (Nature 256 (1975), 495) and Galfre (Meth. Enzymol. 73 (1981) 3), which comprise the fusion of mouse myeloma cells to spleen cells derived from immunized mammals. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. Expression of antibodies or antibody-like molecules in plants can be achieved by methods well known in the art, for example, full-size antibodies (During, Plant. Mol. Biol. 15 (1990), 281-293; Hiatt, Nature 342 (1989), 469-470; Voss, Mol. Breeding 1 (1995), 39-50), Fab-fragments (De Neve, Transgenic Res. 2 (1993), 227-237), scFvs (Owen, Bio/Technology 10 (1992), 790-794; Zimmermann, Mol. Breeding 4 (1998), 369-379; Tavladoraki, Nature 366 (1993), 469-472) and dAbs (Benvenuto, Plant Mol. Biol. 17 (1991), 865-874) have been successfully expressed in tobacco, potato (Schouten, FEBS Lett. 415 (1997), 235-241) or *Arabidopsis*, reaching expression levels as high as 6.8% of the total protein (Fiedler, Immunotechnology 3 (1997), 205-216).

In addition, nucleic acid molecules encoding a mutant form of a protein (e.g., an enzyme) according to the invention can be used to interfere with the activity of the wild-type protein. Such a mutant form preferably has lost its activity and may be derived from the corresponding wild-type protein by way of amino acid deletion(s), substitution(s), and/or additions in the amino acid sequence of the protein. Mutant forms of such proteins may show, in addition to the loss of activity, an increased substrate affinity and/or an elevated stability in the cell, for instance, due to the incorporation of amino acids that stabilize proteins in the cellular environment. These mutant forms may be naturally occurring or, as preferred, genetically engineered mutants.

Plant Transformation

Once an expression cassette, gene and/or gene component of interest has been cloned into an expression system, it is transformed into a plant cell. The expression cassette, gene and or gene component can be expressed transiently or stably in plant. The term “introducing” in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant.

a. Transient Plant Transformation

The methods herein refer to methods to transiently express a expression cassette, gene and/or genetic component of interest in planta in order to formulate predictive models for how said expression cassette gene and/or genetic component of interest will perform in stable transgenic plants. The early application of *Agrobacterium* infiltration (Agro-infiltration) for transient expression was based on poplar and *Phaseolus* (Kapila et al., 1997), and then later extended to tobacco (Vaquero et al., 1999). Transient expression of genes in plants has been known in the art as described earlier see Fischer et al., 1999, *Biotechnol. Appl. Biochem.,* 30, 113-116 for a review. However, past transient assay methods have been limited in their ability to form predictive models of how a relevant gene, expression cassette and/or genetic component of interest will perform in stable transgenic lines. Also, there are limitations including but not limited to: the number of days a protein will be transiently expressed, the amount of protein capable of being expressed, consistency in analysis as well as length of the gene to be transiently expressed. The methods disclosed herein may overcome these limitations. Further, the invention provides a substantially improved process for producing proteins in planta, using commercially available plants without the need to have plant growth facilities. The method can be used to produce at least about 0.1-1.0 mg, at least about 5 mg or at least about 10 mg of protein for analysis. In one embodiment, 1-7 day old leaf tissue is agro-infiltrated with an binary vector comprising an expression cassette comprising a promoter, an intron, and a gene of interest. In some embodiments the expression cassette may comprise translational and/or transcriptional enhancers. In another embodiment the plant leaf tissue is a maize plant leaf tissue that is 1-7 days old upon agro-infiltration. In some embodiments agro-infiltration can be carried out on 1-20 day old plant tissue.

In one embodiment, cells of *Agrobacterium* bearing an expression cassette with a heterologous gene or genes of interest are used to deliver the heterologous gene or genes to a plant tissue for transient expression in the cells and/or extracellular spaces of the plant tissue. Generally, a suitable expression construct comprises: at least one T-DNA border sequence, a regulatory sequence (e.g. promoter), and a gene of interest operably linked to the regulatory control sequence. In one aspect, an expression construct is part of a vector comprising one or more origins of replication, at least one origin of replication suitable for replicating the vector comprising the expression cassette in *Agrobacterium.*

Cultures of *Agrobacterium* cells comprising the expression cassettes described herein are infiltrated into plant tissue. In preferred embodiments, the expression cassettes are infiltrated in 1-7 day old intact plant leaf tissue. Preferably, infiltration occurs in the presence of a vacuum. After incubating the plant tissue under suitable conditions that allow the expression cassette to express the protein in a plurality of plant cells, the protein or protein-substrate by-products may be isolated from the cells. The method requires contacting the plant tissue with *Agrobacterium* comprising a binary vector comprising an expression cassette to be transiently expressed in plant cells, infiltrating the plant tissue with said *Agrobacterium* comprising an expression cassette to be transiently expressed in plant cells to obtain yield of from about 500 μg to about 500 mg of a relevant protein. If more protein is needed to formulate predictive models, one or more additional rounds of agro-infiltration and purification may be performed or more preferably, more intact plant tissue may be used.

The *Agrobacterium* used may be wild type (e.g. virulent) or disarmed. Multiple *Agrobacterium* strains, each expressing a different gene can be used to produce the individual proteins or a heteromultimeri proteins (e.g., antibody) or to reproduce a pathway, such as a metabolic pathway, a chemical synthesis pathway or a signaling pathway. Alternatively, or additionally, a single *Agrobacterium* strain may comprise a plurality of sequences comprising different heterologous genes to evaluate interactions. In one embodiment, at least one *Agrobacterium* strain comprises *Agrobacterium tumefaciens.*

Transformation of a plant with *Agrobacterium* and its use in generation of stable plant transgenics has been well documented. The interaction of an *Agrobacterium* cell comprising a T-DNA border sequence with a plant cell results in the transfer of a single strand copy of *Agrobacterium* T-DNA complexed with proteins to the plant nucleus. For stable transformation, the T-DNA is integrated into the nuclear DNA. Although the process is apparently quite efficient, the non-integrated copies of T-DNA are able to be transiently transcribed resulting in the short-term expression of the T-DNA genes and any other genes that are co-transformed. Since the transient expression is not dependent on integration of DNA or regeneration of plants, it is possible to use the more virulent strains of *Agrobacterium* without the need to use disarmed vectors (i.e. vectors no longer containing tumor inducing genes), although the latter may be used as well.

Suitable strains of *Agrobacterium* include wild type strains (e.g. *Agrobacterium tumefaciens*) or strains in which one or more genes is mutated to increase transformation efficiency, e.g., such as *Agrobacterium* strains wherein the vir gene expression and/or induction thereof is altered due to the presence of mutant or chimeric virA or virG genes (e.g. Chen and Winans, 1991, *J. Bacteriol.* 173: 1139-1144; and Scheeren-Groot et al., 1994, 1 *Bacteriol.* 176: 6418-6246). In another embodiment, the *Agrobacterium* strain can comprise an extra virG gene copy, such as the super virG gene derived from pTiBo542, preferably linked to a multiple-copy plasmid as described in U.S. Pat. No. 6,483,013, for example.

It is well understood in the art that *Agrobacterium* can be transformed with a given binary vector of interest using for example electroporation or chemical induction. See for example, Mersereau M., Pazour G. J., Das A. 1990. Efficient transformation of *Agrobacterium tumefaciens* by electroporation. Gene 90: 149-151 or R. Nishiguchi et al. (1987) Mol. Gen. Genetics 206 1-8.

Other suitable strains of *Agrobacterium* include, but are not limited to: *A. tumefaciens* C58C1 (Van Larebeke et. al., *Nature* 252: 169-170 (1974)), A136 (Watson et. al., *J. Bacteriol* 123: 255-264 (1975)), LBA401 (Klapwijk et al., *J Bacteriol* 141: 128-136 (1980)), LBA4404 (Hoekema et. al., *Nature* 303: 179-180 (1983)), EHA101 (Hood et. al., *J. Bacteriol.* 168: 1291-1301 (1986)), EHA105 (Hood et. al., *Trans. Res.* 2: 208-18 (1993)), AGL1 (Lazo et. al., *Bio/Technology* 2: 963-967 (1991)), and A281 (Hood et. al., supra (1986)).

In one embodiment of the invention, *Agrobacterium* cultures (i.e., comprising an expression cassette according to the invention) are grown for approximately two days in YEB medium or any variation thereof (e.g. yeast extract 6 g/L, peptone 5 g/L, magnesium sulfate 2 mM, and sucrose 5 g/L) supplemented with appropriate antibiotics to select for resistance determinants found on the vectors and the host. To grow cells for transient expression, the starter *Agrobacterium* cultures may be diluted 1:50 into fresh YEB medium. Antibiotics, 50 mM potassium phosphate buffer (pH 5.8) and 20 μM acetosyringone may be added. After 18-24 hours incubation at 28° C., cells reach an absorbance (also referred to as Optical Density or O.D.) at 600 nm of 2.5-3.5. The cells are preferably diluted to an absorbance at 600 nm of 2.5, if necessary, using YEB medium.

In a preferred embodiment of the invention, *Agrobacterium* cultures (i.e., comprising an expression cassette according to the invention) are grown for approximately 24-48 hours in LB medium or any variation thereof and supplemented with appropriate antibiotics to select for resistance determinants found on the vectors and the host. To grow cells for transient expression, the starter *Agrobacterium* cultures may be diluted 1:50 into fresh LB medium. Antibiotics, 10 μM IVIES (pH 5.6) and 100 μM acetosyringone may be added. *Agrobacteria* are grown on a shaker overnight at 250 RPM. After 18-24 hours incubation at 28° C., cells reach an absorbance (also referred to as Optical Density or O.D.) at 600nm of 2.5-3.5. The cells are preferably diluted to an absorbance at 600 nm of 2.5, if necessary, using LB medium. Following incubation, the *Agrobacteria* are pelleted by centrifugation at 4000 g for 10 minutes. The pellets may then be resuspended in infection medium (Murashige and Skoog salts with vitamins, 2% sucrose, 500 μM MES (pH 5.6), 10 μM $MgSO_4$, and 100 μM acetosyringone) to O.D. 600 nm equal to 0.5 and subsequently held at 28° C. for 2-3 hours.

One embodiment of the invention is that following growth and preparation of *Agrobacterium* cultures comprising a binary vector comprising an expression cassette according to the invention, infiltration of individual intact leaves can be carried out. Agro-infiltration is preferably carried out on 1-9 day old recipient plants. More preferably agro-infiltration is carried out on 3-7 day old plants or most preferable 7 day old plants using a 5 ml syringe by pressing the tip of the syringe (without a needle) against the underside surface of the leaf. *Agrobacterium* culture is then infiltrated into the extracellular space of the localized plant cells where the expression cassette may eventually enter into the plant cell and be translated into a protein. Infiltrated plants may be maintained at around 25° C. with a photoperiod of 16 hour light and 8 hour dark cycle. Leaf tissue may be analyzed between 1-10 days after agro-infiltration, more preferably 3-7 days and most preferably at 7 days after agro-infiltration. In a preferred embodiment monocot leaf tissue is agro-infiltrated as described herein and in a more preferred embodiment maize leaf tissue may be agro-infiltrated as described herein.

The invention further encompasses methods of transiently expressing a nucleotide sequence of interest in a plant part comprising the steps of: a) agro-infiltration of a binary vector comprising an expression cassette comprising at least one nucleotide sequence into a plant part; and b) transiently express the at least one nucleotide sequence in the plant part. In embodiments of the invention, the method comprises agro-infiltration of an expression cassette comprising at least one nucleotide sequence into a plant part in planta. As understood by those skilled in the art, agro-infiltration generally comprises infiltration of an *Agrobacterium* culture comprising a binary vector comprising the expression cassette.

Expression cassettes and plant parts are described in more detail elsewhere herein. In embodiments of the invention, the plant part is leaf tissue.

Further, the at least one nucleotide sequence of interest can encode a protein or functional RNA (each as described in more detail elsewhere herein).

In representative embodiments, the plant is a monocotyledenous plant, optionally a cereal plant. Cereal plants are as described herein and include without limitation: maize, wheat, sorghum, barley, millet, oat, rice and/or rye. In embodiments of the invention, the cereal plant is a maize plant or a sorghum plant. In embodiments of the invention, the cereal plant is not a rice plant.

In exemplary embodiments of the invention, the method can be advantageously carried out in relatively young plants. To illustrate, the plant can be from about 1 to about 2, 3, 4, 5, 6, 7, 8 or 9 days old or any subset thereof, e.g., from about 3 to about 4, 5, 6, 7, 8 or 9 days old, or from about 5 to about 6, 7, 8 or 9 days old. In embodiments of the invention, the plant is about 7 days old.

As other exemplary embodiments, a cereal plant can be at about the 1 leaf, 2 leaf, 3 leaf, 4 leaf, 5 leaf, 6 leaf or 7 leaf stage, or any subset thereof, e.g., about the 1 leaf to about the 2 leaf, 3 leaf, 4 leaf, 5 leaf, 6 leaf or 7 leaf stage; about the 2 leaf to about the 3 leaf, 4 leaf, 5 leaf, 6 leaf or 7 leaf stage; about the 3 leaf to about the 4 leaf, 5 leaf, 6 leaf or 7 leaf stage. In embodiments of the invention, the cereal plant is at about the 2 leaf or about the 3 leaf stage. In embodiments, the cereal plant is at about the 2 leaf stage. In embodiments, the cereal plant is at about the 3 leaf stage.

The developmental stages of maize are well-defined, and those skilled in the art are able to ascertain the same. For example, maize developmental stages have been divided into vegetative (V) and reproductive (R) stages. The V stages can be subdivided into VE (emergence) followed by V1, V2, V3, V4, V5, V6, etc. through V(n), where (n) represents the last leaf stage before tasseling (VT) (Special Report No. 48, How a corn plant develops, Iowa State University of Science and Technology Cooperative Extension Service, Ames, Iowa (2005)). The leaf stages are defined according to the uppermost leaf whose leaf collar is visible; the first part of the collar that is visible is the back, which appears as a discolored line between the leaf blade and leaf sheath (Id.). The first leaf generally has a characteristic oval-shape and can be used as a reference point for counting upward to the top visible leaf collar (Id.). If lower leaf loss has occurred (generally beginning around V6), the lower stalk can be split lengthwise and the first node above the first elongated stalk internode is generally the fifth leaf node, which can be used as a reference point (Id.). This nomenclature has been developed for maize, but can be generalized to other cereal plants as well, e.g., for a cereal plant at the 2 leaf stage, uppermost leaf is the second leaf, whose leaf collar is visible, as described in more detail above with respect to V2.

Accordingly, with particular respect to maize plants, the maize plant can be at about the V1, V2, V3, V4, V5, V6 or V7 stage, or any subset thereof, e.g., about the V1 to about the V2, V3, V4, V5, V6 or V7 stage; about the V2 to about the V3, V4, V5, V6 or V7 stage; about the V3 to about the V4, V5, V6 or V7 stage. In embodiments of the invention, the maize plant is at about the V2 or about the V3 stage. In embodiments, the maize plant is at about the V2 stage. In embodiments, the maize plant is at about the V3 stage.

The listing of plant stages, plant age and other ranges described herein are intended to be inclusive. For example, the term "V1 to V3 stage" (and similar terms) includes the V1, V2 and V3 stages.

The agro-infiltration can optionally be carried out using a syringe. In representative embodiments, the syringe is a needleless syringe. In the case of a syringe without a needle, the tip of the syringe can be placed against the undersurface of the plant part (e.g., a leaf, optionally the abaxial surface of the leaf). In one representative embodiment, the syringe is a 5 milliliter syringe. The *Agrobacterium* culture can then be infiltrated into the plant part, where the expression cassette may eventually enter the plant cell(s) and be expressed. Methods of maintaining and harvesting tissue from infiltrated plants are known in the art and are described herein. In embodiments of the invention, the method does not comprise rubbing the leaf (e.g., as described by Grimsley et al., *Nature* 325:177-179 (1987)).

In representative embodiments, the invention may provide the advantage of permitting larger volumes of liquid to be infiltrated into the plant part. This aspect is particularly desirable for infiltration of bacterial cultures such as *Agrobacterium* cultures. In embodiments of the invention, the method comprises agro-infiltration of about 0.1, 0.25 or 0.5 to about 1, 2 or even 3 milliliters or more of a liquid *Agrobacterium* culture comprising the expression cassette. For example, from about 0.25 or 0.5 to about 1 or 2 milliliters of an *Agrobacterium* culture comprising a binary vector comprising the expression cassette can be agro-infiltrated into the plant part. In contrast, in prior art methods utilizing binary vectors delivering a virus or virus vector, the *Agrobacterium* culture was injected (i.e., using a needle connected to a syringe) into maize leaves using only small volumes (e.g., 2 to 20 microliters; see, e.g., Grimsley et al., Nature 325:177-179 (1987); Grimsley et al., *BioTechnology* 6:185-189 (1988); Martin et al., *Virology* 89:695-700 (1999)).

By facilitating the delivery of larger volumes, the invention can advantageously be used to deliver bacterial vectors (e.g., *Agrobacteria*) comprising a nucleotide sequence of interest to a plant part in planta. For example, in embodiments of the invention, the method permits agro-infiltration with a binary vector, wherein the binary vector does not comprise a virus or virus vector.

By avoiding the need to utilize a viral system, the invention may provide other advantages as well. Viral vectors, such as Maize Streak Virus (MSV), are known to have limitations on the size of the nucleic acid they can deliver (Shene et al., *Plant J.* 5:227-236 (1994)). In contrast, the present invention can be used to deliver an expression cassette that is greater than about 1, 1.5, 2, 3, 4 or 5 kilobases or even 10 kilobases and/or less than about 7, 8, 9, 10, 12, 15 or 20 kilobases (including any combination of the foregoing as long as the lower limit is less than the upper limit). In embodiments of the invention, the method can be practiced with expression cassettes that are in the range of about 3 to about 10 kilobases in size.

According to representative embodiments, agro-infiltration of the leaves of a cereal plant (e.g., maize) with a syringe (e.g., a needleless syringe) at a single site can result in infiltration of at least about 5%, 10%, 15%, 20%, 25%, 35%, 50% or more of the leaf tissue, typically restricted to one side of the mid-rib. Optionally, at least about 50, 100, 150, 200, 250 or 500 microliters are infiltrated to a single site. In embodiments of the invention, depending on the size of the leaf, the entire leaf can be infiltrated by moving the syringe to as few as 2, 3, 4, 5 or 6 sites. Thus, in representative embodiments, an entire leaf can be agro-infiltrated using a syringe (e.g., a needleless syringe) according to the present invention in less than about 30, 20, 15 or even 10 seconds. Depending on the size of the leaf, typically about 0.25 or 0.5 to about 1 or 2 milliliters of *Agrobacterium* culture is used to infiltrate the entire leaf.

In some embodiments needleless syringes may be used to carry out agro-infiltration on the underside of young plant leaf tissue. For example any one of the following needleless syringes or commercial equivalents may be used to practice the embodiments of the invention as described herein: 1 ml Tuberculine slip tip (Becton Dickinson Medical, France), 5 ml Luer-slip plastic syringe (National Scientific), 5 ml, 10 ml or 60 ml Luer-lok tip plastic syringe (Becton Dickinson Medical, France), The methods herein can be used to pre-screen expression vectors most suitable for protein expression in a growing plant. In one aspect, the method is used to rapidly screen for variants of genetic components or regulatory sequences which provide for optimal protein expression. Alternatively, or additionally, variant sequences are screened to identify sequences encoding proteins with increased stability (e.g. thermostability) or other desired commercial properties.

b. Stable Plant Transformation

The invention allows for a fast method to formulate predictive models by transiently expressing an expression cassette, gene and/or gene components in planta, and then collecting quantitative and/or qualitative data that is predictive of how said expression cassette, gene and/or gene components would perform in stable transgenic plant lines. Numerous transformation vectors available for plant transformation are known to those of ordinary skill in the plant transformation arts, and the genes pertinent to this invention can be used in conjunction with any such vectors. The selection of a vector will depend upon the preferred transformation technique and the target species for transformation. For certain target species, different antibiotic or herbicide selection markers may be preferred. Selection markers used routinely in transformation include the nptll gene, which confers resistance to kanamycin and related antibiotics (Messing & Vierra. Gene 19: 259-268 (1982); Bevan et al., Nature 304:184-187 (1983)), the bar gene, which confers resistance to the herbicide phosphinothricin (White et al., Nucl. Acids Res 18: 1062 (1990), Spencer et al. Theor. Appl. Genet 79: 625-631 (1990)), the hph gene, which confers resistance to the antibiotic hygromycin (Blochinger & Diggelmann, Mol Cell Biol 4: 2929-2931), and the dhfr gene, which confers resistance to methotrexate (Bourouis et al., EMBO J. 2(7): 1099-1104 (1983)), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629).

Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19 (Bevan, Nucl. Acids Res. (1984)). For the construction of vectors useful in *Agrobacterium* transformation, see, for example, US Patent Application Publication No. 2006/0260011, herein incorporated by reference.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. For the construction of such vectors, see, for example, US Application No. 20060260011, herein incorporated by reference.

For expression of a nucleotide sequence in plant plastids, plastid transformation vector pPH143 (WO 97/32011, example 36) may be used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Transformation techniques for dicotyledons are well known in the art and include *Agrobacterium*-based techniques and techniques that do not require *Agrobacterium*. Non-*Agrobacterium*-mediated techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium*-mediated transformation typically involves the transfer of the binary vector carrying the foreign DNA of interest (e.g. pCIB200 or pCIB2001) to an appropriate *Agrobacterium* strain which may depend on the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877 (1988)).

Transformation of the target plant species by recombinant Agrobacteria usually involves co-cultivation of the Agrobacteria with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation). Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, WO 93/07278 and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (Biotechnology 10: 667-674 (1992)) using particle bombardment into cells of type C long-term regenerable callus, and also by Vasil et al. (Biotechnology 11:1553-1558 (1993)) and Weeks et al. (Plant Physiol. 102: 1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, both of which are incorporated herein by reference. See also, Negrotto et al., Plant Cell Reports 19: 798-803 (2000), incorporated herein by reference.

For example, rice (*Oryza sativa*) can be used for generating transgenic plants. Various rice cultivars can be used (Hiei et al., 1994, Plant Journal 6:271-282; Dong et al., 1996, Molecular Breeding 2:267-276; Hiei et al., 1997, Plant Molecular Biology, 35:205-218). Also, the various media constituents described below may be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; Phytagel, 3 g/liter). Either mature embryos at the initial stages of culture or established culture lines are inoculated and co-cultivated with the *Agrobacterium tumefaciens* strain LBA4404 (*Agrobacterium*) containing the desired vector construction. Agrobacteria is cultured from glycerol stocks on solid YPC medium (100 mg/L spectinomycin and any other appropriate antibiotic) for about two days at 28° C. The Agrobacteria are re-suspended in liquid MS-CIM medium. The *Agrobacterium* culture is diluted to an OD600 of 0.2-0.3 and acetosyringone is added to a final concentration of 200 uM. Acetosyringone is added before mixing the solution with the rice cultures to induce Agrobacteria for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of Agrobacteria. For constructs utilizing the PMI selectable marker gene (Reed et al., In Vitro Cell. Dev. Biol.-Plant 37:127-132), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (To generation) grown to maturity, and the $T_1$ seed is harvested.

The plants obtained via transformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

For the transformation of plastids, seeds of Nicotiana tabacum c.v. "Xanthienc" are germinated seven per plate in a 1" circular array on T agar medium and bombarded 12-14 days after sowing with 1 um tungsten particles (M10, Biorad, Hercules, Calif.) coated with DNA from plasmids pPH143 and pPH145 essentially as described (Svab, Z. and Maliga, P. (1993) PNAS 90, 913-917). Bombarded seedlings are incubated on T medium for two days after which leaves are excised and placed abaxial side up in bright light (350-500 μmol photons/$m^2$/s) on plates of RMOP medium (Svab, Z., Hajdukiewicz, P. and Maliga, P. (1990) PNAS 87, 8526-8530) containing 500 ug/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) Molecular Cloning: A Laboratory Manual, Cold Spring Harbor Laboratory, Cold Spring Harbor). BamHI/EcoRI-digested total cellular DNA (Mettler, I. J. (1987) Plant Mol Biol Reporter 5, 346349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps 7/12plastid targeting sequence. Homoplasmic shoots are rooted aseptically on spectinomycin-containing MS/IBA medium (McBride, K. E. et al. (1994) PNAS 91, 7301-7305) and transferred to the greenhouse.

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

Use of the advantageous genetic properties of the transgenic plants and seeds according to the invention can further be made in plant breeding. Depending on the desired properties, different breeding measures are taken. The relevant techniques are well known in the art and include but are not limited to hybridization, inbreeding, backcross breeding, multi-line breeding, variety blend, interspecific hybridization, aneuploid techniques, etc. Thus, the transgenic seeds and plants according to the invention can be used for the breeding of improved plant lines that, for example, increase the effectiveness of conventional methods such as herbicide or pesticide treatment or allow one to dispense with said methods due to their modified genetic properties.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated as being incorporated by reference herein.

EXAMPLES

Standard recombinant DNA and molecular cloning techniques used here are well known in the art and are described by J. Sambrook, E. F. Fritsch and T. Maniatis, Molecular Cloning: A Laboratory manual, Cold Spring Harbor laboratory, Cold Spring Harbor, N.Y. (1989) and by T. J. Silhavy, M. L. Berman, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

The present invention will now be described by way of several working examples. These examples are for purposes of illustration and are not meant to limit the invention in any way.

Example 1

Construction of Binary Vectors

A total of 29 binary constructs were constructed to test various parameters of the transient assay method and its capabilities of creating a predictive correlation between transient expression of an expression cassette(s) and/or expression elements(s)and how the same expression cassette(s) and/or expression element(s) will perform in stable transgenic plant lines. See Table 1 for a summary of the expression cassette components as well as a experimental summary for each binary construct.

TABLE 1

Summary of Binary Vector Expression Cassettes

| Construct ID | Transcriptional enhancers | Promoter | Translational enhancers | CDS | Objectives |
|---|---|---|---|---|---|
| 18505 | | ZmPEPC | | Gus | To test leaf specific |
| 18506 | FMV + 35S | ZmPEPC | | Gus | *Zea mays* PEPC |
| 18507 | | ZmPEPC | TMV | Gus | promoter with & |
| 18545 | FMV + 35S | ZmPEPC | TMV | Gus | without enhancers |
| 18216 (neg. cont) | | | | No GUS | |
| 18508 | | ZmUbi361 | | Gus | To test *Zea mays* |
| 18509 | FMV + 35S | ZmUbi361 | | Gus | Ubiquitin-361 |
| 18633 | | ZmUbi361 | TMV | Gus | promoter with & |
| 17282 | FMV + 35S | ZmUbi361 | TMV | Gus | without enhancers |
| 18503 | | CMP | | Gus | To test CMP viral |
| 18504 | FMV + 35S | CMP | TMV | Gus | promoter with & without enhancers |
| 17313 | FMV + 35S | ZmTrpA | | Gus | To test stem |
| 17319 | FMV + 35S | ZmTrpA | TMV | Gus | preferred promoter |
| 18746 | | ZmUbi1-10 | | Gus | To test *Zea mays* |
| 18550 | | ZmUbi1-10 | | Gus | Ubiquitin 1 promoter |
| 18874 | FMV + 35S | ZmUbi1-04 | TMV | Gus | with & without Kozak sequence |
| 17084 (ER) | | ZmPEPC | | EG | To test Protein |
| 17085 (chl) | | ZmPEPC | | EG | (endoglucanase) |
| 17086 (apo) | | ZmPEPC | | EG | integrity and function |
| 15944 (ER) | | ZmPEPC | | CBHI-ER | To test Protein |
| 15942 (VSD) | | ZmPEPC | | CBHI-VSD | (cellulase) integrity and function |
| 17305 (cob) | | OsMADs13 | | RNAi-R1 | To test transient |
| 17308 (leaf) | | PepC | | RNAi-R1 | down regulation of a |
| 18286 (stem) | | TrpA | | RNAi-R1 | R1 gene |
| 18221 | FMV + 35S | ZmUbi361 | TMV | Xylanase | To test the predictive |
| 18216 | FMV + 35S | ZmUbi361 | TMV | CBHI | capabilities of the |
| 17632 | FMV + 35S | ZmUbi361 | TMV | EG | transient assay in regards to negative phenotypes |

TABLE 1-continued

| Summary of Binary Vector Expression Cassettes | | | | | |
|---|---|---|---|---|---|
| Construct ID | Transcriptional enhancers | Promoter | Translational enhancers | CDS | Objectives |
| 15060 | | PepC & MTL | | Cry1Ab | To test Efficacy of plants transiently expressing a Cry1Ab gene |

Table 1 outlines binary expression constructs used for both the generation of stable transgenic plants as well as for transient expression in intact young plant leaf tissues. The DNA sequences encoding proteins were codon optimized for the appropriate host. For example, expression constructs designed for tobacco and maize transient and stable transgenic plant expression were codon optimized for dicots while expression constructs designed for sugarcane or maize transient and stable transgenic plant expression were codon optimized for monocots. Codon optimization tables are available through commercial software applications such as Vector NTI 11.0 (Invitrogen, USA).

Standard cloning techniques such as PCR, restriction enzyme digestion, gel electrophoresis and subsequence fragment purification, DNA ligation, bacterial cell transformation and selection, and the like were used to generate the vectors described in Table 1 (see Sambrook 1985 for standard methods). Some of the components of the expression vectors described in Table 1 were synthesized by a commercial DNA synthesis lab (GeneArt, Germany).

The binary vector 18505 contains an expression cassette with the following components operatively linked together in this order: the Maize phosphoenolpyruvate carboxykinase (PEPC) promoter (SEQ ID NO: 1); the beta glucuronidase (GUS) gene (SEQ ID NO: 14); and the maize PEPC termination sequence (SEQ ID NO: 21). 18506 is the same as 18505 except that two transcriptional enhancers, enhancer region from the Figwort mosaic virus (FMV) (SEQ ID NO: 11) and the cauliflower mosaic virus 35s (e35S) enhancer region (SEQ ID NO: 12) are included upstream of the promoter. 18507 is the same as 18505 except that a tobacco mosaic tobamovirus omega (TMV) translational enhancer (SEQ ID NO: 13) is included upstream of the GUS gene. 18545 is the same as 18505 except that the two transcriptional enhancers, FMV and e35S are included upstream of the promoter and the translational enhancer, TMV is included upstream of the GUS gene.

The binary vector 18508 contains an expression cassette with the following components operatively linked together in this order: the Maize ubiquitin 361 (ZmUbi361) promoter (SEQ ID NO: 2); the GUS gene and the ZmUbi361 termination sequence (SEQ ID NO: 22). 18509 is the same as 18508 except that two transcriptional enhancers, FMV and e35S are included upstream of the promoter. 18633 is the same as 18505 except TMV is included upstream of the GUS gene. 17282 is the same as 18633 except that the two transcriptional enhancers, FMV and e35 are included upstream of the promoter.

The binary vector 18503 contains an expression cassette with the following components operatively linked together in this order: the Cestrum yellow leaf curl virus (CMP) promoter (SEQ ID NO: 3); the GUS gene; and the nopaline synthetase (NOS) termination sequence (SEQ ID NO: 23). 18504 is the same as 18503 except that two transcriptional enhancers, FMV and e35S are included upstream of the promoter and the translational enhancer, TMV is included upstream of the GUS gene.

The binary vector 17313 contains an expression cassette with the following components operatively linked together in this order: the maize tryptophan synthase alpha subunit (ZmTrpA) promoter (SEQ ID NO: 4); the GUS and the ZmTrpA termination sequence (SEQ ID NO: 24). 17319 is the same as 17313 except that the two transcriptional enhancers, FMV and e35 are included upstream of the promoter and the translational enhancer, TMV is included upstream of the GUS gene.

The binary vector 18550 contains an expression cassette with the following components operatively linked together in this order: the Maize ZmUbi1-10 promoter (SEQ ID NO: 5); the GUS gene and the NOS termination sequence. 18746 is the same as 18550 except that the Maize Kozak sequence (TAAACC) that ordinarily precedes the ATG codon of the GUS gene, has been eliminated. 18874 is the same as 18550 except that the Maize prZmUbi1-4 (SEQ ID NO: 6) promoter is used in place of the Maize prZmUbi1-10 promoter and the two transcriptional enhancers, FMV and e35S are included upstream of the promoter and the translational enhancer, TMV is included upstream of the GUS gene.

The binary vector 17084 contains an expression cassette with the following components operatively linked together in this order: the ZmPEPC promoter ; a endoglucanase (EG) coding sequence (SEQ ID NO: 15) with a Gamma Zein, 19 amino acid signal peptide at the 5' end and an ER retention sequence (SEKDEL) at the 3' end; and the PepC termination sequence (SEQ ID NO: 25). 17085 is the same as 17084 except that the EG gene is comprises a seed protein storage vacuole targeting sequence. 17086 is the same as 17084 except that the EG gene is targeted to the apoplast. 15944 is the same as 17084 except that a cellobiohydrolase I gene comprising a ER retention sequence (SEQ ID NO: 16) is used in place of the EG. 15942 is the same as 17084 except that the except that a cellobiohydrolase I gene comprising a vacuole targeting sequence (SEQ ID NO: 17) is used in place of the EG gene.

The binary vector 17305 contains an expression cassette with the following components operatively linked together in this order: the Rice MADs box gene promoter region (OsMADs13) (SEQ ID NO: 7); a glucan water dikinase (R1) RNAi cassette (SEQ ID NO: 18); and the OsMADS13 termination sequence (SEQ ID NO: 26). The binary vector 17308 contains an expression cassette with the following components operatively linked together in this order: the Maize PepC promoter ; a R1 RNAi cassette; and the NOS termination sequence. The binary vector 18286 contains an expression cassette with the following components operatively linked together in this order: the Maize TrpA promoter ; the R1 RNAi cassette; and a maize TrpA termination sequence.

The binary vector 18221 contains an expression cassette with the following components operatively linked together in this order: two transcriptional enhancers, FMV and e35S; the ZmUbi361-01 promoter; the translational enhancer, TMV; a xylanase gene (SEQ ID NO: 19); and the ZmUbi361 termination sequence. 18216 is the same as 18221 except that the EG gene is used in place of the xylanse gene. 17632 is the same as 18221 except that the CBHI vacuole targeted gene is used in place of the xylanase gene.

The binary vector 15060 contains an expression cassette with the following components operatively linked together in this order: the Maize PepC promoter; a *Bacillus thurengiensis* Cry1Ab gene (SEQ ID NO: 20); and a NOS termination sequence.

Example 2

In-Planta Transient Assay Method

Expression cassettes were cloned into a binary vector as described in Example 1. The constructs were transferred into *Agrobacterium tumefaciens* strain LBA4404 containing helper plasmid (pSBI) using a freeze-thaw method [An et al., Binary vector. In: Gelvin S B, Schilproot R A (eds), Plant molecular biology manual. Kluwar Academic Publishers, Dordrecht, pp A3 1-19 (1988)]. Preparation of *Agrobacterium* cultures was carried out as described by Azhakanandam et al., Plant Mol. Biol. 63: 393-404 (2007). In brief, the genetically modified agrobacteria were grown overnight in 50 mL of YP medium containing 100 μM acetosyringone and 10 μM MES (pH 5.6), and subsequently were pelleted by centrifugation at 4000 ×g for 10 min. The pellets were resuspended in the infection medium [Murashige and Skoog salts with vitamins, 2% sucrose, 500 μM MES (pH 5.6), 10 μM MgSO4, and 100 μM acetosyringone] to OD600=0.5 and subsequently held at 28 degrees C. for 2-3 hours.

The In-planta transient expression system was established using maize seedlings. Seeds were germinated under greenhouse conditions in 2.5" pots filled with Fafard germination mix. Seedlings were kept under a 14/10 day/night cycle with a day light intensity of 2000 μ-mol-m-2.s-1 maintained with supplemental lighting. The temperature was maintained steady between 23° C.-26° C. Agroinfiltration was tested on seedlings at the V1 to V3 stage, and which had 2-6 visible leaves (Ritchie S. W., Hanway J. J. Benson G. O. (edts): How a Corn Plant Develops: Iowa State Univ Special Report No. 48, July 2005). From this work it was determined that the V-2 stage with 3 visible leaves worked best for agroinfiltration. The agroinfiltration experiment performed mostly using primary and secondary leaves of V2 stage. To make infiltration easier, the seedlings were watered 1-2 hours prior to agroinfiltration to keep the leaf turgid and stomata open. Infiltration of individual leaves was carried out on maize seedlings using a 5 mL syringe body (BD 5 ml Syringe with Luer-Lok™ Tip, BD, Franklin Lakes, N.J. 07427, USA), by pressing the tip of the syringe against the abaxial surface of the leaf. The first and second visible leaves of V2 stage were infiltrated with: 1 ml *agrobacterium* suspension/28 seconds/leaf. Sorghum and rice seedlings were also infiltrated in the same way as for the corn except that the rice seedlings were 45 days old. Infiltrated plants were transferred and maintained under growth chamber conditions set at 25° C. with a 16/8 day/night cycle with a light intensity of 1900 μ-mol-m-2.s-1. Plant tissue was harvested after 3-7 days post infiltration for subsequent analysis.

To ensure that enzyme activity measured was due to plant expression of the enzymes, the expression constructs also incorporated an intron in the polynucleotide sequence coding for the enzyme. The presence of the intron ensures that expression of the enzyme is due to plant expression (able to process out the intron and therefore express a fully processed enzyme) versus *agrobacterium* expression (unable to process the intron and thus not able to express a functional enzyme/protein).

Example 3

Stable Plant Transformation

In order to compare transient expression to stable transgenic plants, each binary construct as described in Example 1 was stably transformed into maize. Maize transformation was carried out as reported (Negrotto et al., 2000; Li et al., 2003; Ishida, 1996). The transgenic events were sent to greenhouse for various analyses, such as DNA, RNA and Protein expression, and for collect seeds from primary transformants.

Example 4

Transient Analysis of Expression Cassette Performance and Subsequent Correlation to Stable Transgenic Lines Tables 2-4 summarizes the data for both transient and stable transformants comprising expression cassettes containing various promoters along with combinations of both transcriptional and translational enhancers. All samples were analyzed for GUS staining by both GUS histochemical assay and GUS quantitative ELISA. GUS histochemical assays was used to localize where GUS protein is present in plant tissue.

Leaves were harvested from transgenic plants containing GUS gene and also infiltrated, plants with GUS gene and stained with GUS buffer as described by Azhakanandam et al (2000). GUS quantitative ELISAs were carried out by carrying out an extraction step using harvested leaf samples in BB/PVP/Tw extraction buffer (0.1M borate, pH 7.5 containing 0.5% Tween-20 and 0.2% polyvinyl pyrrolidone). Approximately 50 mg of leaf tissue was extracted with 0.5 ml extraction buffer. Supernatants were assayed. Total soluble protein quantity was determined by the BCA method (Pierce BCA Protein assay kit, Cat#23223 and 23224) using ovalbumin as a standard. High-binding 96-well plates (Nunc Maxisorp) were coated at 4° C. overnight with 2 μg/ml rabbit anti-GUS IgG (Sigma G5545) in 25 mM borate, 75 mM NaCl, pH 8.5 (100 μl/well). Plates were washed three times with 10 mM Tris, pH 8.0 containing 0.05% Tween-20 and 0.2% NaN3. Samples or standards (GUS Type VII-A, Sigma G7646) were added to the plate (100 μl/well), incubated for 1 hr at room temperature with shaking, and washed five times. 100 μl/well of 2 μg/ml HRP-labeled rabbit anti-GUS IgG (Invitrogen A5790 conjugated to HRP) was then added to the plate, incubated for 1 hr at room temperature with shaking, and washed as before. The HRP-conjugated antibody was detected by adding 100 μl/well tetramethylbenzidine (TMB, Sigma T0440) and developing for 30 min at room temperature. The reaction was stopped by the addition of 100 μl/well of 0.1N HCl. The absorbance was measured at 450 nm with 620 as a reference using a microplate reader (Tecan Sunrise, Research Triangle Park, N.C.). The GUS standard curve uses a 4-parameter curve fit. The curve is plotted linear vs. log with a range from 0 to 320 ng/ml.

PEPC Promoter Evaluation

Constructs 18505, 18506, 18507 and 18545 were used experimentally to determine whether or not a correlation can be made between performance (relative to GUS expression) of the associated expression cassettes in transiently transformed maize leaf tissue when compared to stably transformed maize leaf tissue (See Table 2). For transient assays, 4 plants per construct were used. For each plant, two leaves were agro-infiltrated as described in Example 2. Tissues were collected from the infiltrated leaves and assayed using a quantitative ELISA as described previously for measuring the GUS protein.

TABLE 2

Summary of GUS Staining Data for Both Transient Maize Leaf Tissue and Stable Transgenic Maize Leaf Tissue Comprising the PEPC promoter and Various Combinations of Expression elements

| Construct ID (Promoter, Enhancers) | In-planta corn transient system Average (GUS ng/mg TSP) | Corn transgenic plants (T0) Average (GUS ng/mg TSP) |
|---|---|---|
| 18505 (PEPC) | 8.43 | 7366.25 |
| 18506 (PEPC + FMV + e35s) | 30.89 | 15345.08 |
| 18507 (PEPC + TMV) | 8.8 | 2861.18 |
| 18545 (PEPC + FMV + e35s + TMV) | 20.48 | 6116.78 |
| Null event | NA | 0 |
| Medium infiltrated | 0 | N/A |
| Uninfiltrated | 0 | N/A |

According to the data in Table 2 the transient system is predictive of protein expression on a Low/Medium/High basis for stable transgenic plants. Construct 18506 containing the PEPC promoter in combination with the FMV and e35s transcriptional enhancers performed best in both transients and stable transgenic maize samples. Surprisingly it was shown in both transient and stable transformants that TMV suppressed the expression of GUS. Alternatively the combination of FMV and e35s (not in combination with TMV) significantly increased expression of GUS in both transients and stable transgenics.

ZmUbi361 Promoter Evaluation

Constructs 18508, 18509, 18633 and 17282 were used experimentally to determine whether or not a correlation can be made between performance (relative to GUS expression) of the associated expression cassettes in transiently transformed maize leaf tissue when compared to stably transformed maize leaf tissue (See Table 3). For transient assays, 4 plants per construct were used. For each plant, two leaves were agro-infiltrated as described in Example 2. Tissues were collected from the infiltrated leaves and assayed using a quantitative ELISA as described previously for measuring the GUS protein.

TABLE 3

Summary of GUS Staining Data for Both Transient Maize Leaf Tissue and Stable Transgenic Maize Leaf Tissue Comprising the ZmUbi361 promoter and Various Combinations of Expression elements

| Constructs ID (Promoter, Enhancer) | In-planta corn transient system Average (GUS ng/mg TSP) | Corn transgenic plants (T0) Average (GUS ng/mg TSP) |
|---|---|---|
| 18508 (Ubi361) | 2.93 | 816.74 |
| 18509 (Ubi361, FMV & e35s) | 96.8 | 105899.64 |
| 18633 (Ubi361, TMV) | 6.99 | 1698.78 |
| 17282 (Ubi361, FMV, e35s & TMV) | 11.56 | 31305.12 |
| 18216 (negative control) | 0 | 0 |
| Null event | 0 | 0 |

As seen in Table 3 transient data correlates with data generated in stable corn transgenic plants. As seen with the PEPC promoter, the optimal combination relative to GUS expression was the Ubi361 promoter in combination with both the FMV and e35ss transcription enhancer in both transient and stable transgenic test groups. The second highest GUS expression was the combination comprising the Ubi361 promoter, the FMV and e35s transcriptional enhancers, and the TMV translational enhancer in both transient and stable test groups. Surprisingly, TMV again seemed to suppress GUS expression as seen in the PEPC experiment (Table 2).

CMP Promoter Evaluation

Constructs 18503 and 18504 were used experimentally to determine whether or not a correlation can be made between performance (relative to GUS expression) of the associated expression cassettes in transiently transformed maize leaf tissue when compared to stably transformed maize leaf tissue (See Table 4). For transient assays, 4 plants per construct were used. For each plant, two leaves were agro-infiltrated as described in Example 2. Tissues were collected from the infiltrated leaves and assayed using a quantitative ELISA as described previously for measuring the GUS protein.

TABLE 4

Summary of GUS Staining Data for Both Transient Maize Leaf Tissue and Stable Transgenic Maize Leaf Tissue Comprising the CMP promoter and Various Combinations of Expression elements

| Constructs ID (Promoter, Enhancer) | In-planta corn transient system Average (GUS ng/mg TSP) | Corn transgenic plants (T0) Average (GUS ng/mg TSP) |
|---|---|---|
| 18503 (CMP) | 8.13 | 523.06 |
| 18504 (CMP, FMV e35s & TMV) | 6.7 | 217.4 |
| 18216 (negative control) | 0 | NA |
| Null event | NA | 0 |
| Medium infiltrated | 0 | N/A |
| Uninfiltrated | 0 | N/A |

As seen in Table 4, transient data was again predictive of the best expression cassette (18504) relative to GUS expression for stable transgenic maize plants.

Overall, as seen in Tables 2-4 the transient assay method successfully predicted (relative to GUS expression levels) that all three promoters in combination with both the FMV and e35s transcriptional enhancers would perform best in stable transgenic maize lines. This same predictive capability of the in-planta transient assay method may also be seen in transient analysis of the TRPA stem preferred promoter as seen in Table 5. The transient analysis can be carried out over the course of about a week compared to the analysis of TO maize plants which would take possibly months to grow up plants and analyze. The transient method was also able to quickly identify (as validated in stable transgenics) that the TMV translational enhancer can in many cases suppress gene (GUS) expression which is surprising due to TMV enhancer region's supposed function. At least in the test samples as described in Tables 2-4 above the presence of TMV suppressed GUS expression. Again, this observation can be predicted by use of the in-planta transient methods as taught herein. Another observation predictive of what occurred in stable transgenic plants is the fact that the combination of both a FMV and e35s transcriptional enhancers allows for a significant increase in GUS expression. As demonstrated in Tables 2-4 above, the in-planta transient method can quantitatively and quickly predict the best promoter/enhancer combination to carry forward in stable transgenic maize lines. The in-planta transient method would make significant savings in time, resources, greenhouse space and expenditures in the evaluation of best expression cassettes for expression of any given gene of interest.

TABLE 5

Summary of GUS Staining Data for Both Transient Maize Leaf Tissue and Stable Transgenic Maize Leaf Tissue Comprising the TrpA promoter

| Constructs ID | In-planta corn transient sysytem Average (GUS ng/mg TSP) | Corn transgenic plants (T0) Average (GUS ng/mg TSP) |
|---|---|---|
| 17313 | 3.3 | 73.6 |
| 17319 | 4.44 | 1612.8 |
| 18216 (negative control) | 0 | 0 |
| Null event | NA | 0 |
| Medium infiltrated | 0 | N/A |
| Uninfiltrated | 0 | N/A |

Example 5

Transient Analysis of Qualitative Protein Expression Associated with Cellular Targeting and Subsequent Correlation to Stable Transgenic Lines Western Blot analysis was carried out on both transient and stable transgenic plants expressing a endoglucanase gene. As seen in Table 6 the endoglucanase was targeted to the ER, the chloroplast and the apoplast. Approximately 200 mg fresh leaf tissue of each plant ID was ground to a fine powder using a Kleco grinder, then extracted in 1 mL of 100 mM Na acetate, 0.02% Tween, 0.02% Na azide pH 4.75, and Complete protease inhibitor cocktail tablets (Roche). Samples were placed on bench top rotators for 30-60 minutes and then centrifuged at 3000 rpm for 10 min. The amount of total protein extracted was measured by Pierce BCA protocol as outlined in product literature. Following endoglucanase extraction, Western blot analysis was carried out using the standard protocol. EG protein was detected by Western blot by anti EG antibody probe.

TABLE 6

Western Blot Analysis of Transient and Stable Transgenic Maize Plants Expressing a Heterologous Endoglucanse Gene Targeted to Various Subcellular Organelles

| Constructs ID | Subcellular targeting | Plant ID | Protein size* | |
|---|---|---|---|---|
| | | | Transient system | Stable transgenic plant |
| 17084 | ER | 1 | greater than expected | greater than expected |
| | | 2 | greater than expected | greater than expected |
| | | 3 | greater than expected | greater than expected |
| | | 4 | greater than expected | greater than expected |
| | | 5 | greater than expected | greater than expected |
| | | 6 | greater than expected | NA |
| 17085 | Chloroplast | 1 | expected | Expected |
| | | 2 | expected | Expected |
| | | 3 | expected | Expected |
| | | 4 | expected | Expected |
| | | 5 | expected | Expected |
| | | 6 | expected | NA |
| 17086 | Apoplasts | 1 | greater than expected | greater than expected |
| | | 2 | greater than expected | greater than expected |
| | | 3 | greater than expected | greater than expected |
| Media infiltrated control | | 1 | None | |
| Un-infiltrated control | | 1 | | |

As seen in Table 6, the transient assay method was able to predict that targeting a Endoglucanase in either the ER or Apoplast would result in a Endoglucanase having a protein greater in size than expected according to Western Blot analysis in both transient and stable transgenic maize lines. This may be due to, for example glycosylation of the protein. Alternatively, the transient assay successfully predicted that targeting a endoglucanase to the chloroplast would result in an expected protein size as indicated by Western Blot Analysis in stable transgenic maize lines. Overall, the in-planta assay method was able to predict the best means to express a protein in plant based on qualitative data (i.e. Western Blot Analysis). It is also envisioned that protein cleavage could be predicted in the same manner using the in-planta transient methods described herein.

Additionally, as shown in Table 7, endoglucanase activity can be measured in transient transformants. For enzyme activity assay, approximately 200 mg fresh leaf tissue of a transgenic plant was ground to a fine powder using a Kleco grinder, then extracted in 1 mL of 100 mM Na acetate, 0.02% Tween, 0.02% Na azide pH 4.75, and Complete protease inhibitor cocktail tablets (Roche). Samples were placed on bench top rotators for 30-60 minutes and then centrifuged at 3000 rpm for 10 min. The amount of total protein extracted was measured by Pierce BCA protocol as outlined in product literature. EG activity assay was carried out using carboxymethyl-cellulose substrate (Megazyme). All samples were assayed in triplicate. Following extraction, 20 uL of sample was incubated with 245 ug CMC-4M substrate for 120 minutes at 40 deg. Zero time point samples were immediately processed. After incubation, glucose release was measured using the GOPOD assay kit (Megazyme). Enzyme activity was detected as the hydrolysis of the cellulose substrate to glucose. The GOPOD assay was performed by combining 20 uL of sample reaction, or glucose standards of known concentrations, with 200 uL GlucoseOx Reagent (Megazyme) in a 96-well assay plate (Costar 3370) and incubated for 20 minutes at 37 degrees C. Absorbance at wavelength of 510 nm was measured using SpectraMax 384 Plus plate reader. Absorbance values of sample reactions were converted to glucose concentration using the equation from a glucose standard curve generated by plotting the absorbance value versus the known glucose standard concentration. Enzyme activity is recorded as umol glucose/minute/g tissue.

TABLE 7

Endoglucanase Enzyme Activity Measurements from Transient Leaf Tissue

| Construct ID | Plant ID | Avg umol/min/mg TSP | STDev |
|---|---|---|---|
| 18216 (Ubi-EG) | 1 | 0.28 | 0.01 |
| | 2 | 0.35 | 0.03 |
| | 3 | 0.37 | 0.08 |
| | 4 | 0.3 | 0.03 |
| 17282 (vector control) | 6 | 0.07 | 0.01 |
| LBA4404 (agro control) | 7 | 0.12 | 0.05 |

Example 6

Rapid Transient Analysis of the Down-regulation of a Maize R1 Gene

Binary constructs 17305, 17308, and 18286 comprise expression cassettes comprising an RNAi for the maize endogenous starch degradation gene glucan water dikinase (R1). As shown in Table 8, transient transformed leaf tissue may be used to predict whether or not a particular RNAi can in fact-down-regulate a particular endogenous gene, in this case maize R1. R1 mRNA levels were analyzed for transiently transformed maize young leaf tissue by qRT-PCR. To perform this analysis, RNA was extracted from the leaf samples followed by DNA digestion. TaqMan assays were selected based on the target of interest which consists of a forward and reverse primer and a FAM-labeled probe that were specific to the target sequence. A species specific, TET-labeled reference target is also employed for each sample for relative expression calculation. One-step RT-PCR reactions are set up in triplicate (3 for endogenous reference gene, 3 for target gene) in 384 well PCR plates. A wild type control and no-RT negative control are included on each plate to test for non-specific amplification and DNA contamination, respectively. Results are captured on a real-time thermocycler, threshold values are set by the analyzer for each reporter and the resulting data is reported. Relative expression (2^-deltaCt where deltaCt=target−reference) is calculated for each sample. As seen in Table 8, all RNAi constructs were successful in down regulation of the R1 when compared to wild type (uninfiltrated) tissue. The in-planta method was surprisingly able to rapidly verify that each RNAi cassette is functional in regards to down-regulation of the R1 gene. Construct 17305 contains a OSMADs13 promoter which is a maize cob specific promoter as described in U.S. Patent Application 2007/0006344A1. It is surprising that the transient in planta assay was able to conclude that the RNAi behind a OsMADs13 promoter down-regulates the R1 gene in leaf. This indicates that the in planta assay may be able to evaluate not only promoters that are active in the leaf but also promoters that are non-leaf promoters such as for example seed specific promoters, cob specific promoters or root specific promoters.

TABLE 8

Transient Evaluation of the Down-regulation of a Maize R1 Gene

| Construct ID-plant ID | R1 gene-mRNA transcripts level |
|---|---|
| 17305-1 | 313.24 |
| 17305-2 | 312.82 |
| 17305-3 | 277.89 |
| 17305-4 | 266.42 |
| 17305-5 | 405.33 |
| 17305-6 | 311.46 |
| 17308-1 | 272.63 |
| 17308-2 | 203.89 |
| 17308-3 | 290.11 |
| 17308-4 | 271.68 |
| 17308-5 | 256.96 |
| 17308-6 | 268.37 |
| 18286-1 | 464.96 |
| 18286-2 | 381.51 |
| 18286-3 | 258.22 |
| 18286-4 | 203.87 |
| 18286-5 | 256.57 |
| 18286-6 | 260.63 |
| Wild Type (uninfiltrated) | 540.74 |

Example 7

Use of the In-Planta Transient Method to Predict Negative Plant Phenotypes and/or Toxicity Associated with the Expression of a Heterologous Gene Construct 18221 comprises a xylanase constitutively expressed by Ubi361. As shown in Table 9, observation of transient maize tissue transformed with binary construct 18221 resulted in obvious cell death. Specifically, large circles of dead leaf tissues appeared on the transformed intact leaf a few days after transient infiltration of the xylanase cassette. This indicates that the gene may have a toxic effect to the plant cell. When this same gene is expressed in maize seed it is known (data not shown) that the seed will have a shriveled phenotype with low germination rates. This data indicates that the in-planta transient assay may be a useful tool in the pre-evaluation of gene candidates in regards to toxicity and/or negative phenotype problems in stable transgenics

TABLE 9

Prediction of a negative phenotype associated with the expression of a heterologous gene

| Construct ID | Plant ID | Phenotype (cell death) |
|---|---|---|
| 18221 (corn transient) | 1 | ++++ |
| | 2 | +++ |
| | 3 | ++++ |
| Xyn-6002-apo for corn seed | Event 1* | ++++ |
| 17282 (negative control) | 1 | − |
| | 2 | − |
| Uninfiltrated corn | 1 | − |

"++++": Indicates a phenotype was observed
"−": Indicates no phenotype was observed Example 8

Use of the In-Planta Transient Method to Predict Protein Efficacy

Construct 15060 comprises an expression cassette containing a Cry1Ab gene which is known to be effective in controlling various Lepidopteron pests when expressed in transgenic crops as described in U.S. Pat. No. 6,075,185. Insect Bioassays using European corn borer (ECB) were carried out using plant extract containing Cry1Ab from lyophilized plant tissue transiently transformed with the Cry1Ab gene. As shown in Table 10, transiently expressed Cry1Ab efficacy can be confirmed at 93.75% ECB mortality following 7 days of assay compared to control (empty vectors) which showed little or no mortality.

TABLE 10

In-Planta transient evaluation of a Cry1Ab gene

| Plate # 1 Construct | # of Wells | Insect | Read 7 days Live Larvae | Dead Larvae | Mortality (%) |
|---|---|---|---|---|---|
| 15060 (Cry1AB) | 8 | ECB | 1 | 15 | 93.75% |
| LBA4404 | 4 | ECB | 7 | 1 | 12.50% |
| AX5707 | 4 | ECB | 8 | 0 | 0.00% |
| 0.2% Bactoagar | 8 | ECB | 16 | 0 | 0.00% |

Example 8

Use of the In-Planta Transient Method to Predict Metabolic Profiles

Transient expression of enzymes in maize leaves was performed using the binary vector pEB47 comprising a monocot optimized polynucleotide sequence encoding a sucrose isomerase (SEQ ID NO: 27). The binary vector pEB47 contains an expression cassette with the following components operatively linked together in this order: an FMV enhancer; a 35S enhancer; a maize ubiquitin promoter; a maize gamma-zein ER targeting sequence which directs the sucrose isomerase polypeptide to the ER; a sporamin vacuolar targeting sequence which directs the sucrose isomerase polypeptide from the ER to the vacuole; a maize optimized polynucleotide sequence encoding a sucrose isomerase; a NOS terminator.

Maize leaves were harvested and analyzed for the presence of isomaltulose and trehalulose (products of sucrose isomerase activity within the maize leaf). The amino acid sequence for a sucrose isomerase expressed by *Erwinia carotovora* has been listed in GeneBank under the accession number YP049947. Sucrose isomerase enzyme activity was assayed by combining the enzyme with the substrate, sucrose, and measuring the production of isomaltulose and trehalulose. The total soluble protein extract from the recombinant *E. coli* was assayed for sucrose isomerase activity by incubating 10 microliters of supernatant *E. coli* lysate, as described above, with 90 microliters of 292 mM sucrose 50 mM sodium phosphate buffer (pH 6.0) at 30 degrees C. for 20 hours. The reaction product was screened for the presence of isomaltulose and trehalulose by thin layer chromatography (TLC) and high pressure liquid chromatography (HPLC). TLC was performed by spotting 3 microliters of the supernatants of the growth media onto AL SIL G silica gel plates (Whatman) and developed twice in a solvent consisting of 3 parts ethylacetate: 3 parts acetic acid: 1 part distilled water. After drying, the plates were sprayed with a dye mixture consisting of 4 milliliters aniline, 4 g diphenylamine, 200 milliliters acetone, and 30 milliliters 80% phosphoric acid. Isomaltulose and trehalulose were distinguished from other sugars, such as sucrose, by their relative mobility and by the distinct colors produced when they reacted with aniline dye. Greenish yellow indicates the presence of isomaltulose, red indicates the presence of trehalulose, and brown/black indicates the presence of sucrose. The monosaccharides, glucose and fructose, produced by hydrolysis of sucrose were blue or red-orange respectively.

Identification of the sugars present in each lane of the developed TLC plate was possible by comparing both the relative mobility of the sugars present in the samples and the staining color with aniline dye to the relative mobility and staining color of sugar standards. The reaction product of sucrose isomerase incubated with sucrose as described above was three colored bands. The highest mobility band had a purple color and migrated with the same mobility as both glucose and fructose standards blue and red colored respectively and is therefore interpreted to be a mixture of co migrating glucose and fructose released by hydrolysis of one of the disaccharides: sucrose, isomaltulose, or trehalulose. The middle band corresponded with the isomaltulose standard in both coloration and relative mobility and is therefore identified as isomaltulose. The slowest migrating band had a red coloration and migrated slower than either the isomaltulose, or sucrose standards. The relative mobility of this sugar band corresponds well with published reports on the migration of trehalulose in similar TLC assays (Cho et al. Biotechnology Letters (2007) 29:453-458; an isomaltulose-producing microorganism isolated from traditional Korean food.) Therefore this sugar band was concluded to be trehalulose. No trehalulose standard was available at the time of the TLC assay, however, subsequent HPLC (Dionex) analysis of sucrose isomerase reaction products and standards obtained later indicate that this band was definitely trehalulose. Also, it is important to note that the reaction product6 did not contain any sucrose which has a higher relative mobility than isomaltulose and trehalulose and slower mobility than the monosaccharides glucose and fructose. The absence of sucrose was expected due to the complete conversion of sucrose into isomaltulose and trehalulose due to the activity of the sucrose isomerase enzyme. Alternatively, supernatants were screened by HPCL using 16 mM NaOH to separate sucrose isomerase reaction products followed by a linear gradient from 10 to 40 min using 200 mM NaOH at 1 ml/min on a Dionex DX-600 system with ED50 electrochemical detector (Dionex Co.).

Table 12 outlines data that demonstrates sucrose isomerase is actively expressed in maize leaves transiently expressing sucrose isomerase and leads to the accumulation of the sugars, isomaltulose and trehalulose within the maize leaf. The data indicates that the in planta transient assay method may be used to make metabolic profiles such as for example sugar profiles.

TABLE 12

Carbohydrate analysis (HPAEC) of maize leaves transiently expressing sucrose isomerase (SEQ ID NO: 24).

| Sample | Glucose + fructose (% of total sugar) | Sucrose (% of total sugar) | Trehalulose (% of total sugar) | Isomaltulose (% of total sugar) |
|---|---|---|---|---|
| 47-6 (pEB47) | 78.9 | 17.2 | 2.4 | 1.5 |
| 47-7 (pEB47) | 63.7 | 33.3 | 2.1 | 0.9 |
| 47-8 (pEB47) | 73.1 | 16.0 | 7.3 | 3.6 |
| Negative control (GUS containing construct) | 69.4 | 30.6 | 0.0 | 0.0 |
| Negative control leaf tissue | 58.2 | 41.8 | 0.0 | 0.0 |

Example 9

Use of the In-Planta Transient Method in Various Plants

The transient in-planta method can be used in various plants as shown in the previous examples (maize) and in Table 13 (sorghum) and Table 14 (rice). AmCyan is a fluorescent reporter gene that can be analyzed by methods well known in the art. Rice transient lines were analyzed using GUS staining methods.

TABLE 13

Transient expression of AmCyan gene in *sorghum*

| *Sorghum* Genotype | Constructs ID | Transient AmCyan Average (ng/mg TSP) |
|---|---|---|
| Brandes | 13601 | 14.59 |
| Della | 13601 | 20.75 |
| Dale | 13601 | 21.37 |
| Brandes (negative control) | LBA4404 | 0 |
| Della (negative control) | LBA4404 | 0 |
| Dale (negative control) | LBA4404 | 0 |
| Uninfiltrated | Uninfiltrated | 0 |

TABLE 14

Transient expression of GUS gene in rice (c.v. Nipponbare)

| Constructs ID | Transient GUS Average (ng/mg TSP) |
|---|---|
| 17282 | 20.6 |
| 18545 | 9.01 |
| 18216 (negative control) | 7.24 |

Although the foregoing invention has been described in some detail by way of illustration and example for purposes of clarity and understanding, it will be clear to those of skill in the art that certain changes and modifications may be practiced within the scope of the appended claims.

What is claimed is:

1. A method of transiently expressing a nucleotide sequence of interest in young plant leaf tissue of an intact monocot comprising the steps of:
 a) producing at least one expression cassette wherein said expression cassette comprises at least one nucleotide sequence operably linked to a promoter;
 b) using a syringe to agro-infiltrate at least about 0.05 milliliters of a liquid comprising genetically modified Agrobacteria suspended to an $OD_{600}$ of 0.5 into at least one visible leaf of a monocot plant wherein the monocot plant is at the two leaf stage or the three leaf stage of development;
 c) transiently expressing said nucleotide sequence in the said leaf tissue of an intact monocot plant;
 wherein the monocot plant is selected from the group consisting of maize, wheat, sorghum, barley, millet, oat, sugar cane, and rice.

2. The method of claim 1, wherein the young plant leaf tissue is no greater than 5, 6, 7, 8, 9 or 10 days old.

3. The method of claim 1, wherein the promoter is a constitutive or leaf preferred promoter.

4. The method of claim 1, wherein the nucleotide sequence is transiently expressed for at least about 5, 6, 7, 8, 9 or 10 days.

5. The method of claim 1, wherein the method comprises agro-infiltration of a binary vector.

6. The method of claim 1, wherein agro-infiltration is carried out on the underside of said young plant leaf tissue.

7. A method of transiently expressing a nucleotide sequence of interest in young plant leaf tissue of an intact maize plant comprising the steps of:
 a) producing at least one expression cassette, wherein said expression cassette comprises at least one nucleotide sequence operably linked to a promoter;
 b) using a syringe to agro-infiltrate at least about 0.05 milliliters of a liquid comprising genetically modified Agrobacteria suspended to an $OD_{600}$ of 0.5 into visible leaf tissue of a maize plant at the V2 or V3 stage;
 c) transiently expressing said nucleotide sequence in the said leaf tissue of an intact monocot plant.

8. A method of predicting the performance of at least one heterologous gene or genetic element in stable transgenic monocot plant lines based on its performance in transient assays, said method comprising the steps of:
 a) producing at least one expression cassette wherein said expression cassette comprises at least one heterologous gene operably linked to a constitutive or leaf-preferred promoter;
 b) using a syringe to agro-infiltrate at least about 0.05 milliliters of a liquid comprising genetically modified Agrobacteria suspended to an $OD_{600}$ of 0.5 into at least one visible leaf of a monocot plant wherein the monocot plant is at the two leaf stage or the three leaf stage of development;
 c) transiently expressing said heterologous gene in said plant leaf or leaves of an intact monocot plant;
 d) collecting infiltrated leaf tissue;
 e) measuring quantitative, qualitative or quantitative and qualitative data related to the transient transfection of the tissue, the transient expression or transcript accumulation of the said heterologous gene, the accumulation or activity of the heterologous protein encoded by the said heterologous gene, or to the presence or non-presence of a particular phenotype on the collected tissue of step (c);
 f) predicting the performance of at least one heterologous gene or genetic element in stable transgenic monocot plant lines, based on analyses of the data generated in step (e);
 wherein said monocot plant is selected monocot plant is selected from the group consisting of maize, wheat, sorghum, barley, millet, oat, sugar cane, and rice.

9. The method of claim 8, wherein the quantitative data consists of measuring protein expression levels.

10. The method of claim 8, wherein the quantitative data consists of measuring activity of the said heterologous protein on a substrate.

11. The method of claim 8, wherein the quantitative data consists of insect bioassays.

12. The method of claim 8, wherein the quantitative data consists of ELISA analysis.

13. The method of claim 8, wherein the quantitative data consists of PCR analysis for transcript copy number.

14. The method of claim 8, wherein quantitative data consists of a data derived from any one of the following: a Northern Blot, a Southern Blot or a Western Blot.

15. The method of claim 8, wherein the quantitative data consists of data derived from an enzyme assay.

16. The method of claim 8, wherein the qualitative data consists of data derived from a Western Blot.

17. A method of predicting the performance of at least one expression cassette for use in stable transgenic monocot plant lines, said method comprising the steps of:

a) producing at least one expression cassette wherein said expression cassette comprises at least one heterologous gene operably linked to a constitutive or leaf-preferred promoter;

b) using a syringe to agro-infiltrate at least about 0.05 milliliters of a liquid comprising genetically modified Agrobacteria suspended to an $OD_{600}$ of 0.5 into at least one visible leaf of a monocot plant wherein the monocot plant is at the two leaf stage or the three leaf stage of development;

c) transiently expressing said expression cassette in said plant leaf or leaves of an intact monocot plant;

d) collecting infiltrated leaf tissue;

e) measuring quantitative, qualitative or quantitative and qualitative data related to the transient transfection of the tissue, the transient expression or transcript accumulation of the said heterologous gene, the accumulation or activity of the heterologous protein encoded by the said heterologous gene, or to the presence or non-presence of a particular phenotype on the collected tissue of step (c);

f) predicting the performance of at least one expression cassette in stable transgenic plant lines based on analyses of data gathered in step (e);

wherein said monocot plant is selected from the group consisting of maize, wheat, sorghum, barley, millet, oat, sugar cane, and rice.

18. The method of claim 17, wherein the quantitative data predicts the performance of an enhancer sequence in a stable transgenic plant line.

19. The method of claim 17, wherein the quantitative data predicts the performance of a promoter sequence in a stable transgenic plant line.

20. The method of claim 17, wherein the quantitative data predicts the performance of an expression cassette comprising at least one promoter operably linked to at least one enhancer in a stable transgenic plant line.

* * * * *

SEQUENCE LISTING

<160> NUMBER OF SEQ ID NOS: 26

<210> SEQ ID NO 1
<211> LENGTH: 2778
<212> TYPE: DNA
<213> ORGANISM: Zea mays
<220> FEATURE:
<221> NAME/KEY: promoter
<222> LOCATION: (1)..(2778)

<400> SEQUENCE: 1
tagaggcaac ccaagatagg tgaaagataa gcttcctttg tcacaattga atattcgtgc 60
aaggtggtcc aactattatt ttgagatgtt tattgagacc attgaggacc tttgagtaat 120
taactctcaa cctagtagaa attcgttacc aactgggttg cataggattt catgattaac 180
agtgtgtttg gtttagctgt gagttttctc ctatgaaaag actgttgtga gaacaaaaag 240
ttgaaaatcg tttagttcaa actgttgtga gttatccact gtaaacaaat tgtatattgt 300
ttatatacac tatgtttaac tatatctctt aatcaatata tacaattaaa aaactaaatt 360
cacatttgtg ttcctaatat tttttacaaa taaatcattg ttcgattcca tttgtaatat 420
tttttattaa aattgttttt atttcattta ttataaacac ttaattgttt taatcctatt 480
ttagtttcaa tttattgtat ctatttatta atataacgaa cttcgataag aaacaaaagc 540
aaggtcaagg tgttttttca gggctagttt gggagtccaa aaattggagg gggttagagg 600
ggctaaaatc tcattcttat tcaaaattga ataaggaggg gattttagcc cctctaatca 660
tcttcagttt tgtggctccc aaactagccc tcaaagtaga tgtggaaaag ttgaacccct 720
tttattcagc ttctagaagc aggtttgaaa aatagaacca aacaaaccct aaaagtgtgt 780
gaatttttaa caggtaatgg caggttaatt attcacatct ctttggtcat gtttaagagg 840
ctgaaaatag atcaattgca agaacaaata gcagagtgga taggggtggg gaggggtcgt 900
ctccctatct gacctctctc ctgcattgga ttgcctttct ccgtactcta tttaaaagta 960
caaatgaggt gccggattga tggagtgata tataagtttg atgtgttttt cacatacgtg 1020
acaagtatta ttgaaagaga acagttgcat tgctactgtt tggatatggg aaaactgaga 1080
attgtatcat gcgatggccg atcagttctt tacttagctc gatgtaatta atgcacaatg 1140
ttgatagtat gtcgaggatc tagagatgta atggtgttag gacacgtggt tagctactaa 1200
tataaatgta aggtcaaaat tcgatggttt attttctatt ttcaattacc tagcattatc 1260
tcatttctaa ttgtgtgata acaaatgcat tagaccataa ttctgtaaat acgtacattt 1320
aagcacacag tctatatttt aaaattcttc tttttgtgtg gatatcccaa cccaaatcca 1380
cctctctcct caatccgtgt atcttcaccg ctgccaagtg ccaacaacac atcgcatcgt 1440
gcaaatcttt gttggtttgt gcacggtcgg cgccaatgga ggagacacct gtacggtgcc 1500
cttggtagaa caacatcctt atccctatat gtatggtgcc tttcgtagaa tggcacccct 1560
tatccctaca atagccatgt atgcatacca agaattaaat atactttttc ttgaaccaca 1620
ataatttatt atagcggcac ttcttgttct ggttgaacac ttatttggaa caataaaatc 1680
ccgagttcct aaccacaggt tcactttttt tccttatcct cctaggaaac taaattttaa 1740
attcataaat ttaattgaaa tgttaatgaa aacaaaaaaa ttatctacaa agacgactct 1800
tagccacagc cgcctcactg caccctcaac cacatcctgc aaacagacac cctcgccaca 1860
tccctccaga ttcttccctc cgatgcagcc tacttgctaa cagacgccct ctccacatcc 1920
tgcaaagcat tcctccaaat tcttgcgatc ccccgaatcc agcattaact gctaagggac 1980
gccctctcca catcctgcta cccaattagc caacggaata acacaagaag gcaggtgagc 2040
agtgacaaag cacgtcaaca gcaccgagcc aagccaaaaa ggagcaagga ggagcaagcc 2100
caagccgcag ccgcagctct ccaggtcccc ttgcgattgc cgccagcagt agcagacacc 2160
cctctccaca tcccctccgg ccgctaacag cagcaagcca agccaaaaag aagcctcagc 2220
cacagccggt tccgttgcgg ttaccgccga tcacatgccc aaggccgcgc ctttccaaac 2280
gccgagggcc gcccgttccc gtgcacagcc acacacacac ccgcccgcca acgactcccc 2340
atccctattt gaacccaccc gcgcactgca ttgatcacca atcgcatcgc agcagcacga 2400
gcagcacgcc gtgccgctcc aaccgtctcg cttccctgct tagcttcccg ccgcgccttg 2460
gcgtcgacca aggcacccgg ccccggcgag aagcaccact ccatcgacgc gcagctccgt 2520
cagctggtcc caggcaaggt ctccgaggac gacaagctca tcgagtacga agcgctgctc 2580
gtcgaccgct tcctcaacat cctccaggac ctccacgggc ccagccttcg cgaatttgta 2640
actaaccacc gccgcggccc atttcttctt cgaccggttg ccgcctgcgc gcggcactgg 2700
tcgtgtcgtg tgctcgctcg tctccctccg gtgcttacta ctgtaatcct tgcaggtcca 2760
ggagtgctac gaggtaaa 2778

<210> SEQ ID NO 2
<211> LENGTH: 3089
<212> TYPE: DNA
<213> ORGANISM: Zea mays
<220> FEATURE:
<221> NAME/KEY: promoter
<222> LOCATION: (1)..(3089)

<400> SEQUENCE: 2
gacaaacctc tatatgtaga gtacaggagc ttttacagga ccctgctgga gccagcctta 60
gggggaaaac ttccaggcgg taggtcacat acatcagtga ggtaggagaa atgtgccaac 120

```
cacgtggtgt cgaccaatct acattctaat ctatatcatt atataattta tcagtttaaa    180
ctttacaaaa tctatctaaa caaatcacat ctacacccat aacattcgtt aaatctaaca    240
cagtatcaaa actagcggtt caaatcgatg gataacatgt tctcccatat ccattcaaat    300
ctgatagata atattattta gatcatgtat tctctctccc ctctccctcg acgcctcctc    360
ctgccccgtg tccctgacct gtctccctca cttatgatgt tgtctctatc atcaatcgct    420
ccttttatat tgtgatcact gtccacccct attcctactc gggattaggg atggcaatgg    480
aaaatttctc atcgaggaat agctcttcat acccatccca cgacgcagaa atttcctcgc    540
gggaataccc acgaacgttt acagaagaca tttcttcccc atccatattc cccacgggca    600
taaatttccg acggagatca acgtccctat ttacattata attaggaaat gcatcctttg    660
ttattaataa aaacactttc acttatatat attgttagat gtaagaaatc attatgggta    720
tattaaaata aacatatttg tacaatgatt gatctcttac ccaaataatt atttgttttt    780
attattagct agtatacgaa aacatcacca cgtacaggtt tgacggattc ccacagaaac    840
agggatgaaa aatacttcta catccctgtc ccgtttaccc atctgagaaa gcgggaaatc    900
gggcatagga tccattgcca aagatcgtag ggctataacc taagcgttgc aacgaagcga    960
agcagacggt ggagacgttg acgcaaagca atgaacttga acggcatctc tctcgctggc   1020
cctggccttc tcgaaggctc tgcgtgggtc cttgcgcagt tgcgccgcag cgggctggca   1080
gcatccggaa attgcgtctt gcgtggcgga gcagacacta aggtactatt ttacgttcta   1140
tttagttgga ctgtggcggt aaactatgaa aaaaactatt gcagactatg agctattaaa   1200
aagctaaaaa ttatttagtg taaaccacta aaaaccatta aaaattcttt gatatatatt   1260
ttcacagttt tataaaaaat ccactaaaaa caggtcaaat aagctttcaa ttttacacta   1320
cgaaaaagtc agcttttaaa aaaaactgct taaatccagt cctttagttt aatttttatc   1380
ttttaggaaa caaaagccaa aactaaaacc aaaccaaacc tacctttaaa accgatctaa   1440
taggaacgcg gtgtttggaa caactagata ttaattttag aggttagacc gccacgaaag   1500
cgtcactgca cacggcattc ccctccccta gcgttatcgt cgcaccataa ataaccatcc   1560
tctcctcgcc tttccccaca tctcatcttc gtctgtgttc ttgggcgtac gcggacacag   1620
ccccgatccg aatcgtcgtc cttgcgagcc tcgccgatcc cccactcccc tcccctcgct   1680
tcaaggtaac tgcgatcatc catcctcccg cttccactct cccttcacct cctctgcttg   1740
ctaggtatac gaacatacga tttattacgg gttatatggg ggcttcgatt cccagatctg   1800
gcgatctatt atcgtagctc cgagtcctcg atctagtaat tgtgggatat gcttgtaaga   1860
ggctctgaga tgggttgggt tgggttgggt cgctgtgacg attccaacag cctcgtttct   1920
tagggttgga tcttctcgtg gtttcctttt taattaaata agtacctgat gcagaatggt   1980
gcgtcctatt agatggaacc ttgatcttga tgcatctaac cttgatcttg ttcgctgtga   2040
tgattccaac aggctcgttt cttaggcctg ttcgtctggt tcgtcagatc agtttcgttg   2100
cttttggcct cgttgtaagg tccatccaga tcggagtaga atcgaatgat ttattatacg   2160
gtagctgctg gtctcattag atttggatct gcatgggttg aacatatgta ttcataatta   2220
atatggtgta tacgtactag tttgctggtc ttattttttt agcctgattg cttctgcctt   2280
tctggcaacg cctgatccac gcgttagcta gagtggattt tagttccttg tttacgcggc   2340
cacacctgcc gcctagaaaa gctgcagcga gaactctaat taaatttgga tctacatgtg   2400
ctagcatata tgtttgtaat taatatgatg gatgaatatg tgcttcagag ttgagttcct   2460
gttgatgctg tagttctgcc tgaattgttg aggctgtagc ttctgcctga ttaaaatgca   2520
```

```
ccgtgcctat ctgttaaact ctagggtgtg tgatttagcc ggtgacggtg gtttaatatg   2580

tgtaatttca ctgcttatag taatgcaatt cacctttgct tgaacatgca ttgtcttgtt   2640

gctttgttct atacacatgc ttagctatta tctgatgagc atgcactgtt ttgttctgtt   2700

tgatatgcat gctcagaaat atgtagatgt gtggctcctg ctcggttgtt ctttatcatc   2760

cacctgttga acatgcatgt tcttgtcgct tatctttatt atatattacc ttcgttctcg   2820

aatatttgtc gcccgctagt tcatttttga actaaaccgt gacaaataaa atagaacgta   2880

gggagtggca tcatgctgct actgtacctt acggtggcaa ctacatcttg agcacgcata   2940

tatcttatag tgttcctttt cttttcctcc ttggtctact gttatatgct tacctttttt   3000

tggtttcctt gcagatccag agtattttta caacaattac caacaacaac aaacaacaaa   3060

caacattaca attactattt acataaacc                                     3089
```

```
<210> SEQ ID NO 3
<211> LENGTH: 397
<212> TYPE: DNA
<213> ORGANISM: Cestum veneris
<220> FEATURE:
<221> NAME/KEY: promoter
<222> LOCATION: (1)..(397)

<400> SEQUENCE: 3

tggcagacaa agtggcagac atactgtccc acaaatgaag atggaatctg taaaagaaaa     60

cgcgtgaaat aatgcgtctg acaaaggtta ggtcggctgc ctttaatcaa taccaaagtg    120

gtccctacca cgatggaaaa actgtgcagt cggtttggct ttttctgacg aacaaataag    180

attcgtggcc gacaggtggg ggtccaccat gtgaaggcat cttcagactc caataatgga    240

gcaatgacgt aagggcttac gaaataagta agggtagttt gggaaatgtc cactcacccg    300

tcagtctata aatacttagc ccctccctca ttgttaaggg agcaaaatct cagagagata    360

gtcctagaga gagaaagaga gcaagtagcc tagaagt                             397
```

```
<210> SEQ ID NO 4
<211> LENGTH: 2195
<212> TYPE: DNA
<213> ORGANISM: Zea mays
<220> FEATURE:
<221> NAME/KEY: promoter
<222> LOCATION: (1)..(2195)

<400> SEQUENCE: 4

ccaaaagtct tgaaaaaatt cagcggggag gccattaggg caggggtact gttatgtttt     60

aaagagaaca ccactttctt gatctcttct aaagagaaat gttttgtaag aaagatcctg    120

tcctcctcat ccaacctttt catcggcaaa tttttcatag agatattaga ggcaagagag    180

gggccaaaaa gatccatgta aatggaagtg gccacctggt tgatacctcc ctcatcttca    240

acagaaaatc cattatgaaa aagtgaatgg attttaaact cttctttttc ttcccttttg    300

caatgagctg aaaatatctg gtattattct catcaccctc attaatgaat ctgtccctag    360

caatttgctt tctcttgatc ccttctgcag ccaccatgtt tcttaaattc cactccatat    420

caagcttttc caatctatca gaatctgaga tggctgcaat ctctctcatt ttctcaagga    480

tatcgatgtt atccataagg tatttcttga acttcttata tttcccttcg acatttatat    540

tccatccttt caacattttt ttgttcaatc ttttttgttt ttttcctttc caaacatcga    600

tacatttcct gctcctcaca ggtaaggacg agctttcaaa aaaccttctg ctttaaagtc    660

aggtctgagc ctccagcaaa gctcacatat ctaaagtccc tcttcttagt tgggacagag    720
```

```
tcagtgctaa gacacatggg aacatgacca gaaaaaaaaa atcatattta gcccagagac    780

aacaatattc ttgtactgca agtctcgtta tgggctagca aaggaatcta cccaacttct    840

caaatgtgtt gggatgtcaa gtatatagac tattcatcag ttccaactct atcaaactgt    900

gcagctcaat tatagagttg aataaagtgc tccatctatt tgttcttatc ctcatatttg    960

gttaagatat taaaatcacc tcccaccaac atttaaagtg caccatttaa agtggctcgc   1020

gagcaccaaa ccgctgaaaa ccggaaatgt ttagcacgtt ggcagcgggc cccttttcta   1080

tctcatcgtg ttcttcgttg tccaccacgg cccacgggcc aacgctcctc catcctgtag   1140

tgtagagtat attccatttg cgaccgagcc gagcatcgat ccagccacac tggccactgc   1200

cagccagcca tgtggcactc ctacgtatac tacgtgaggt gagattcact cacatgggat   1260

gggaccgaga tattttactg ctgtggttgt gtgagagata ataaagcatt tatgacgatt   1320

gctgaacagc acacaccatg cgtccagata gagaaagctt tctctcttta ttcgcatgca   1380

tgtttcatta tcttttatca tatatatata acacatatta aatgattctt cgttccaatt   1440

tataattcat ttgacttttt tatccaccga tgctcgtttt attaaaaaaa atattataat   1500

tattgttact ttttgttgta atattgttta gcatataata aactttgata ctagtatgtt   1560

tccgagcaaa aaaaaatatt aatatttaga ttacgagccc attaattaat tatattcgag   1620

acaagcgaag caaagcaaag caagctaatg ttgcccctgc tgtgcatgca gaggcccgct   1680

cttgctataa acgaggcagc tagacgcgac tcgactcatc agcctcatca acctcgacga   1740

aggaggaacg aacggacagg ttgttgcaca gaagcgacag atctgctttc gcgcccaaaa   1800

cgtcctcctc ctcctcgctg tcctcggcgt tgcaggcagc tcagtcgccg ccgctgctcc   1860

tgaggcggat ctcgtcgacc gcaacaccga gacggaggta cgacgcggcc gtcgtcgtca   1920

ctaccaccac cactgctaga gctgcggcgg ctgctgtcac ggttcccgcc gccccgccgc   1980

aggcgggccg ccgccgccgg tgccaccaaa gcaagcggcg gcacccgcag aggaggagcc   2040

gtccggtgtc ggacaccatg gcggcgctca tggccaaggg caaggttcgt atagtacgcg   2100

cgcgtgtcgt cgtcgttatt ttgcgcatag gcgcggacat acacgtgctt tagctagcta   2160

acagctagat catcggtgca gacggcgttc atccc                              2195
```

```
<210> SEQ ID NO 5
<211> LENGTH: 1993
<212> TYPE: DNA
<213> ORGANISM: Zea mays
<220> FEATURE:
<221> NAME/KEY: promoter
<222> LOCATION: (1)..(1993)

<400> SEQUENCE: 5
```

```
ctgcagtgca gcgtgacccg gtcgtgcccc tctctagaga taatgagcat tgcatgtcta     60

agttataaaa aattaccaca tattttttttt gtcacacttg tttgaagtgc agtttatcta    120

tctttataca tatatttaaa ctttactcta cgaataatat aatctatagt actacaataa    180

tatcagtgtt ttagagaatc atataaatga acagttagac atggtctaaa ggacaattga    240

gtattttgac aacaggactc tacagtttta tctttttagt gtgcatgtgt tctccttttt    300

ttttgcaaat agcttcacct atataatact tcatccattt tattagtaca tccatttagg    360

gtttagggtt aatggttttt atagactaat ttttttagta catctatttt attctatttt    420

agcctctaaa ttaagaaaac taaaactcta ttttagtttt tttatttaat aatttagata    480

taaaatagaa taaaataaag tgactaaaaa ttaaacaaat accctttaag aaattaaaaa    540
```

```
aactaaggaa acatttttct tgtttcgagt agataatgcc agcctgttaa acgccgtcga    600

cgagtctaac ggacaccaac cagcgaacca gcagcgtcgc gtcgggccaa gcgaagcaga    660

cggcacggca tctctgtcgc tgcctctgga cccctctcga gagttccgct ccaccgttgg    720

acttgctccg ctgtcggcat ccagaaattg cgtggcggag cggcagacgt gagccggcac    780

ggcaggcggc ctcctcctcc tctcacggca ccggcagcta cgggggattc ctttcccacc    840

gctccttcgc tttcccttcc tcgcccgccg taataaatag acacccctc cacaccctct    900

ttccccaacc tcgtgttgtt cggagcgcac acacacacaa ccagatctcc cccaaatcca    960

cccgtcggca cctccgcttc aaggtacgcc gctcgtcctc cccccccccc cctctctacc   1020

ttctctagat cggcgttccg gtccatggtt agggcccggt agttctactt ctgttcatgt   1080

ttgtgttaga tccgtgtttg tgttagatcc gtgctgctag cgttcgtaca cggatgcgac   1140

ctgtacgtca gacacgttct gattgctaac ttgccagtgt ttctctttgg ggaatcctgg   1200

gatggctcta gccgttccgc agacgggatc gatttcatga ttttttttgt ttcgttgcat   1260

agggtttggt ttgccctttt cctttatttc aatatatgcc gtgcacttgt ttgtcgggtc   1320

atcttttcat gctttttttt gtcttggttg tgatgatgtg gtctggttgg gcggtcgttc   1380

tagatcggag tagaattctg tttcaaacta cctggtggat ttattaattt tggatctgta   1440

tgtgtgtgcc atacatattc atagttacga attgaagatg atggatggaa atatcgatct   1500

aggataggta tacatgttga tgcgggtttt actgatgcat atacagagat gctttttgtt   1560

cgcttggttg tgatgatgtg gtgtggttgg gcggtcgttc attcgttcta gatcggagta   1620

gaatactgtt tcaaactacc tggtgtattt attaattttg gaactgtatg tgtgtgtcat   1680

acatcttcat agttacgagt ttaagatgga tggaaatatc gatctaggat aggtatacat   1740

gttgatgtgg gttttactga tgcatataca tgatggcata tgcagcatct attcatatgc   1800

tctaaccttg agtacctatc tattataata aacaagtatg ttttataatt attttgatct   1860

tgatatactt ggatgatggc atatgcagca gctatatgtg gattttttta gccctgcctt   1920

catacgctat ttatttgctt ggtactgttt cttttgtcga tgctcaccct gttgtttggt   1980

gttacttctg cag                                                      1993
```

```
<210> SEQ ID NO 6
<211> LENGTH: 1992
<212> TYPE: DNA
<213> ORGANISM: Zea mays
<220> FEATURE:
<221> NAME/KEY: promoter
<222> LOCATION: (1)..(1992)

<400> SEQUENCE: 6

ctgcagtgca gcgtgacccg gtcgtgcccc tctctagaga taatgagcat tgcatgtcta     60

agttataaaa aattaccaca tatttttttt gtcacacttg tttgaagtgc agtttatcta    120

tctttataca tatatttaaa ctttactcta cgaataatat aatctatagt actacaataa    180

tatcagtgtt ttagagaatc atataaatga acagttagac atggtctaaa ggacaattga    240

gtattttgac aacaggactc tacagtttta tctttttagt gtgcatgtgt tctccttttt    300

ttttgcaaat agcttcacct atataatact tcatccattt tattagtaca tccatttagg    360

gtttagggtt aatggttttt atagactaat ttttttagta catctatttt attctatttt    420

agcctctaaa ttaagaaaac taaaactcta ttttagtttt tttatttaat aatttagata    480

taaaatagaa taaaataaag tgactaaaaa ttaaacaaat accctttaag aaattaaaaa    540

aactaaggaa acatttttct tgtttcgagt agataatgcc agcctgttaa acgccgtcga    600
```

```
cgagtctaac ggacaccaac cagcgaacca gcagcgtcgc gtcgggccaa gcgaagcaga    660
cggcacggca tctctgtcgc tgcctctgga cccctctcga gagttccgct ccaccgttgg    720
acttgctccg ctgtcggcat ccagaaattg cgtggcggag cggcagacgt gagccggcac    780
ggcaggcggc ctcctcctcc tctcacggca ccggcagcta cgggggattc ctttcccacc    840
gctccttcgc tttcccttcc tcgcccgccg taataaatag acaccccctc cacaccctct    900
ttccccaacc tcgtgttgtt cggagcgcac acacacacaa ccagatctcc cccaaatcca    960
cccgtcggca cctccgcttc aaggtacgcc gctcgtcctc cccccccccc ctctctacct   1020
tctctagatc ggcgttccgg tccatggtta gggcccggta gttctacttc tgttcatgtt   1080
tgtgttagat ccgtgtttgt gttagatccg tgctgctagc gttcgtacac ggatgcgacc   1140
tgtacgtcag acacgttctg attgctaact tgccagtgtt tctctttggg gaatcctggg   1200
atggctctag ccgttccgca gacgggatcg atttcatgat ttttttgtt tcgttgcata    1260
gggtttggtt tgcccttttc ctttatttca atatatgccg tgcacttgtt tgtcgggtca   1320
tcttttcatg cttttttttg tcttggttgt gatgatgtgg tctggttggg cggtcgttct   1380
agatcggagt agaattctgt ttcaaactac ctggtggatt tattaatttt ggatctgtat   1440
gtgtgtgcca tacatattca tagttacgaa ttgaagatga tggatggaaa tatcgatcta   1500
ggataggtat acatgttgat gcgggtttta ctgatgcata tacagagatg ctttttgttc   1560
gcttggttgt gatgatgtgg tgtggttggg cggtcgttca ttcgttctag atcggagtag   1620
aatactgttt caaactacct ggtgtattta ttaattttgg aactgtatgt gtgtgtcata   1680
catcttcata gttacgagtt taagatggat ggaaatatcg atctaggata ggtatacatg   1740
ttgatgtggg ttttactgat gcatatacat gatggcatat gcagcatcta ttcatatgct   1800
ctaaccttga gtacctatct attataataa acaagtatgt tttataatta ttttgatctt   1860
gatatacttg gatgatggca tatgcagcag ctatatgtgg atttttttag ccctgccttc   1920
atacgctatt tatttgcttg gtactgtttc ttttgtcgat gctcaccctg ttgtttggtg   1980
ttacttctgc ag                                                        1992
```

<210> SEQ ID NO 7
<211> LENGTH: 1894
<212> TYPE: DNA
<213> ORGANISM: Oryza sativa
<220> FEATURE:
<221> NAME/KEY: promoter
<222> LOCATION: (1)..(1894)

<400> SEQUENCE: 7

```
ttccaaaatt aagcacacac atttgcaaga actagctagg catgcatata tgataattaa     60
ccggcaagtt gacttcagtt attctgcaga tgtactaaac acataacaag ggatgatcag    120
ttgcttattt ttttcataac ttgctaggtt gcttataact ccagccttct ggacatcgac    180
caatctctaa acatacttta gcagtgccta caaagtacaa acaactaaat acctctctgc    240
agatcagtgt ttctaggcac aaattacaca agatagaaaa aaggagaggt tataaattct    300
tgcttaaaga atatacatgt aaagatgtct aaatagctat aaatgggtaa gcaagatagc    360
aaagaaggcc agtggccttt gcagctaagc tagctagcta gcccttcttc ctctctttcc    420
tgctttccct ttgccttctc ctattaatcc tctgcacctc acacagcagc agaaaaccca    480
ccaactggag ctctcctttc ctactccaag aaacgaaggt agagaaagaa agatcagatc    540
agcttcagga ccaattttag ctaggttata tatctctttg cgtgctaatg tgttttagtt    600
```

```
atctgggtgt gtgtagagtt ctttgttaag gcactgattc agctgcagtt tagattcaag     660

tttgtatgtt ctctctttga ggaaaagaaa cccttttcct gtgcttcgag ttcttgcaaa     720

gagaaactgt gatgcttggc ttccagtttg atgcttcttt gttcagattg gaaattcttc     780

ctagcttctt tctctattta tgtagcaagg attctttccg gcccagtgat cctggtttct     840

tttggaaggt ttcagttttt tcgttctttc ttgaaatttc tcttcttgcc ttaggcagat     900

ctttgatctt gtgaggagac aggagaaaag gaagaagcta gtttcctgcg gccgacctct     960

tgcttctcac tttgtgatga gttttctttg gtcaattctt agctagatat gctaagatag    1020

ttagttaagc aaatcgaaat tgctagcttt tccatgcttt cttaaacatg attcttcaga    1080

tttggttggt tctttttttt ccttttttgtg gagacgtgct gttcttgcat cttatccttc    1140

ttgattcatc tacccatctg gttctttgag ctttcttttt cgcttcttcc cttcattatt    1200

tcgagcaatc tctgcacatc tgaaagtttt gtttcttgag actacttttg ctagatcttg    1260

tttactcgat cactctatac ttgcatctag gctcctttct aaataggcga tgattgagct    1320

ttgcttatgt caaatgatgg gatagatatt gtcccagtct ccaaatttga tccatatccg    1380

ccaagtcttt catcatcttt ttctttcttt tttatgagca aaaatcatct ttttctttca    1440

aagttcagct tttttctctt gttttacccc tctttagcta tagctggttt cttattcctt    1500

ttggatttac atgtataaaa catgcttgaa tttgttagat cgatcacttt atacacatac    1560

tatgtgaatc acgatctcag atctctcagt atagttgaat tcattaattt cttagatcga    1620

tcagcgtgtg atgtagtact gtaaatcact actagatctt tcatcagtct cttttctgca    1680

tctatcaatt tctcatgcaa gttttagttg tttctttaat ccggtctctc tctctttttt    1740

aatcagctga gagtttgtgc tgttctttaa tcattaccag atctttcatc agtactctct    1800

cttctgcatc tatcaaactt ctcatgcaat gtttttgctg ttctttgatc tgatctctgg    1860

tctccttttt tgttgatcag ttgagagcaa gaag                                1894
```

<210> SEQ ID NO 8
<211> LENGTH: 2557
<212> TYPE: DNA
<213> ORGANISM: Zea mays
<220> FEATURE:
<221> NAME/KEY: promoter
<222> LOCATION: (1)..(2557)

<400> SEQUENCE: 8

```
ttgcacatga caacaattgt aagaggatgg agaccacaac gatccaacaa tacttctgcg      60

acgggctgtg aagtatagag aagttaaacg cccaaaagcc attgtgtttg gaatttttag     120

ttattctatt tttcatgatg tatcttcctc taacatgcct taatttgcaa atttggtata     180

actactgatt gaaaatatat gtatgtaaaa aaatactaag catatttgtg aagctaaaca     240

tgatgttatt taagaaaata tgttgttaac agaataagat taatatcgaa atggaaacat     300

ctgtaaatta gaatcatctt acaagctaag agatgttcac gctttgagaa acttcttcag     360

atcatgaccg tagaagtagc tctccaagac tcaacgaagg ctgctgcaat tccacaaatg     420

catgacatgc atccttgtaa ccgtcgtcgc cgctataaac acggataact caattccctg     480

ctccatcaat ttagaaatga gcaagcaagc acccgatcgc tcaccccata tgcaccaatc     540

tgactcccaa gctctgtttc gcattagtac cgccagcact ccacctatag ctaccaattg     600

agacctttcc agcctaagca gatcgattga tcgttagagt caaagagttg gtggtacggg     660

tactttaact accatggaat gatggggcgt gatgtagagc ggaaagcgcc tccctacgcg     720

gaacaacacc ctcgccatgc cgctcgacta cagcctcctc ctcgtcggcg ccacaacgag     780
```

```
ggagcccgtg gtcgcagcca ccgaccagca tgtctctgtg tcctcgtccg acctcgacat    840

gtcatggcaa acagtcggac gccagcacca gactgacgac atgagtctct gaagagcccg    900

ccacctagaa agatccgagc cctgctgctg gtagtggtaa ccattttcgt cgcgctgacg    960

cggagagcga gaggccagaa atttatagcg actgacgctg tggcaggcac gctatcggag   1020

gttacgacgt ggcgggtcac tcgacgcgga gttcacaggt cctatccttg catcgctcgg   1080

cgcggagttt acggggactt atccttacga cgtgctctaa ggttgcgata acgggcggag   1140

gaaggcgtgt ggcgtgcgga gacggtttat acacgtagtg tgcgggagtg tgtttcgtag   1200

acgcgggaaa gcacgacgac ttacgaaggt tagtggagga ggaggacaca ctaaaatcag   1260

gacgcaagaa actcttctat tatagtagta gagaagagat tataggagtg tgggttgatt   1320

ctaaagaaaa tcgacgcagg acaaccgtca aaacgggtgc tttaatatag tagatatata   1380

tatatagaga gagagagaaa gtacaaagga tgcatttgtg tctgcatatg atcggagtat   1440

tactaacggc cgtcgtaaga aggtccatca tgcgtggagc gagcccattt ggttggttgt   1500

caggccgcag ttaaggcctc catatatgat tgtcgtcggg cccataacag catctcctcc   1560

accagtttat tgtaagaata aattaagtag agatatttgt cgtcgggcag aagaaacttg   1620

gacaagaaga agaagcaagc taggccaatt tcttgccggc aagaggaaga tagtggcctc   1680

tagtttatat atcggcgtga tgatgatgct cctagctaga aatgagagaa gaaaaacgga   1740

cgcgtgtttg gtgtgtgtca atggcgtcca tccttccatc agatcagaac gatgaaaaag   1800

tcaagcacgg catgcatagt atatgtatag cttgttttag tgtggctttg ctgagacgaa   1860

tgaaagcaac ggcgggcata tttttcagtg gctgtagctt tcaggctgaa agagacgtgg   1920

catgcaataa ttcagggaat tcgtcagcca attgaggtag ctagtcaact tgtacattgg   1980

tgcgagcaat tttccgcact caggagggct agtttgagag tccaaaaact ataggagatt   2040

aaagaggcta aaatcctctc cttatttaat tttaaataag tagtgtattt gtattttaac   2100

tcctccaacc cttccgattt tatggctctc aaactagcat tcagtctaat gcatgcatgc   2160

ttggctagag gtcgtatggg gttgttaata gcatagctag ctacaagtta accgggtctt   2220

ttatatttaa taaggacagg caaagtatta cttacaaata aagaataaag ctaggacgaa   2280

ctgctggatt attactaaat cgaaatggac gtaatattcc aggcaagaat aattgttcga   2340

tcaggagaca agtggggcat tggaccggtt cttgcaagca agagcctatg gcgtggtgac   2400

acggcgcgtt gcccatacat catgcctcca tcgatgatcc atcctcactt gctataaaaa   2460

gaggtgtcca tggtgctcaa gctcagccaa gcaaataaga cgacttgttt cattgattct   2520

tcaagagatc gagcttcttt tgcaccacaa ggtcgag                            2557

<210> SEQ ID NO 9
<211> LENGTH: 2315
<212> TYPE: DNA
<213> ORGANISM: Zea mays
<220> FEATURE:
<221> NAME/KEY: promoter
<222> LOCATION: (1)..(2315)

<400> SEQUENCE: 9

cttagaggca acccaagata ggtgaaagat aagctacctt tgtcacaatt gaagattcgt     60

gcaaggtggt tcaactatta ttctgagatg tttattggga ccattgagga cctttgagta    120

attaactctc aaccttgtgg aaattcgtta ccaactgggt tgcataggat ttcatgatta    180

agagtgtgtt tggtttagct gtgagttttc tcctatgaaa aaactgttgt gagaaaaaat    240
```

-continued

```
agttggaagt cgtttagttc aaactgttgt gagttatcca ctgtaaacaa attgtatatt    300
gtttatatac actctgttta aatatatctc ttaatcagta tatataatta aaaaactaat    360
ttcacatttg tgttcctaat attttttaca aataaatcat tgtttaattc catttgtaat    420
aagtttttat taaaattgct tttatttcat ttattataaa catttaattg ttttaatcct    480
attttagttt taatttattg tatctattta ttaatataac gaacttcgat aagaaacaaa    540
agcaaggtca aggtgttttt tcaaagtagt tgtggaaaag ctgaacccct tttattcaac    600
ttttagaagc aggaaaacag aaccaaacag accctaaaaa tgtgtgaatt tttagcaggt    660
taattattcg catctctttg gtcatgttta agaggctgga atagatcaac tgcaagaaca    720
catagcagag tggatagggg gggggggggg ggggggaggg tcgtcgtctc cctatctgac    780
ctctcttctg cattggattg ccttttttcgg tactctattt aaaacttaaa agtacaaatg    840
aggtgccgga ttgatggagt gatatataag tttgatgtgt ttttcacata agtgacaagt    900
attattgaaa gagaacattt gcattgctac tgtttgcata tgggaaaatt gagaattgta    960
tcatgccatg gccgatcagt tctttactta gctcgatgta atgcacaatg ttgatagtat   1020
gtcgaggatc tagcgatgta atggtgttag gacacgtggt tagctactaa tataaatgta   1080
aggtcattcg atggtttttc tattttcaat tacctagcat tatctcattt ctaattgtga   1140
taacaaatgc attagaccat aattctgtaa atatgtacat ttaagcacac agtctatatt   1200
ttaaaattct tctttttgtg tggatatccc aacccaaatc cacctctctc ttcaatccgt   1260
gcatgttcac cgctgccaag tgccaacaac acatcgcatc gtgcatatct ttgttggctt   1320
gtgcacggtc ggcgccaatg gaggagacac ctgtacggtg cccttggtag aacaacatcc   1380
ttatccctat atgtatggtg cccttcgtag aatgacaccc cttatcccta caatagccat   1440
gtatgcatac caagaattaa atatactttt tcttgaacca caataattta ttatagcggc   1500
acttcttgtt caggttgaac acttatttgg aacaataaaa tgccgagttc ctaaccacag   1560
gttcactttt ttttttcctt atcctcctag gaaactaaat tttaaaatca taaatttaat   1620
ttaaatgtta atggaaacaa aaaattatct acaaagacga ctcttagcca cagccgcctc   1680
actgcaccct caaccacatc ctgcaaacag acaccctcgc cacatccctc cagattcttc   1740
actccgatgc agcctacttg ctaacagacg ccctctccac atcctgcaaa gcattcctcc   1800
aaattcttgc gatcccccga atccagcatt aactgctaag ggacgccctc tccacatcct   1860
gctacccaat tagccaacgg aataacacaa gaaggcaggt gagcagtgac aaagcacgtc   1920
aacagcaccg agccaagcca aaaaggagca aggaggagca agcccaagcc gcagccgcag   1980
ctctccaggt ccccttgcga ttgccgccag cagtagcaga cacccctctc cacatcccct   2040
ccggccgcta acagcagcaa gccaagccaa aaaggagcct cagccgcagc cggttccgtt   2100
gcggttaccg ccgatcacat gcccaaggcc gcgcctttcc gaacgccgag ggccgcccgt   2160
tcccgtgcac agccacacac acacccgccc gccaacgact ccccatccct atttgaaccc   2220
acccgcgcac tgcattgatc accaatcgca tcgcagcagc acgagcagca cgccgtgccg   2280
ctccaaccat ctcgcttccg tgcttagctt cccgc                              2315
```

<210> SEQ ID NO 10
<211> LENGTH: 2071
<212> TYPE: DNA
<213> ORGANISM: Oryza sativa
<220> FEATURE:
<221> NAME/KEY: promoter
<222> LOCATION: (1)..(2071)

<400> SEQUENCE: 10

```
tccatgctgt cctactactt gcttcatccc cttctacatt ttgttctggt ttttggcctg      60
catttcggat catgatgtat gtgatttcca atctgctgca atatgaatgg agactctgtg     120
ctaaccatca acaacatgaa atgcttatga ggcctttgct gagcagccaa tcttgcctgt     180
gtttatgtct tcacaggccg aattcctctg ttttgttttt caccctcaat atttggaaac     240
atttatctag gttgtttgtg tccaggccta taaatcatac atgatgttgt cgtattggat     300
gtgaatgtgg tggcgtgttc agtgccttgg atttgagttt gatgagagtt gcttctgggt     360
caccactcac cattatcgat gctcctcttc agcataaggt aaaagtcttc cctgtttacg     420
ttattttacc cactatggtt gcttgggttg gtttttttcct gattgcttat gccatggaaa     480
gtcatttgat atgttgaact tgaattaact gtagaattgt atacatgttc catttgtgtt     540
gtacttcctt cttttctatt agtagcctca gatgagtgtg aaaaaaacag attatataac     600
ttgccctata aatcatttga aaaaaatatt gtacagtgag aaattgatat atagtgaatt     660
tttaagagca tgttttccta aagaagtata tattttctat gtacaaaggc cattgaagta     720
attgtagata caggataatg tagacttttt ggacttacac tgctaccttt aagtaacaat     780
catgagcaat agtgttgcaa tgatatttag gctgcattcg tttactctct tgatttccat     840
gagcacgctt cccaaactgt taaactctgt gtttttttgcc aaaaaaaaat gcataggaaa     900
gttgctttta aaaaatcata tcaatccatt ttttaagtta tagctaatac ttaattaatc     960
atgcgctaat aagtcactct gtttttcgta ctagagagat tgttttgaac cagcactcaa    1020
gaacacagcc ttaacccagc caaataatgc tacaacctac cagtccacac ctcttgtaaa    1080
gcatttgttg catggaaaag ctaagatgac agcaacctgt tcaggaaaac aactgacaag    1140
gtcataggga gagggagctt ttggaaaggt gccgtgcagt tcaaacaatt agttagcagt    1200
agggtgttgg tttttgctca cagcaataag aagttaatca tggtgtaggc aacccaaata    1260
aaacaccaaa atatgcacaa ggcagtttgt tgtattctgt agtacagaca aaactaaaag    1320
taatgaaaga agatgtggtg ttagaaaagg aaacaatatc atgagtaatg tgtgggcatt    1380
atgggaccac gaaataaaaa gaacattttg atgagtcgtg tatcctcgat gagcctcaaa    1440
agttctctca ccccggataa gaaaccctta agcaatgtgc aaagtttgca ttctccactg    1500
acataatgca aaataagata tcatcgatga catagcaact catgcatcat atcatgcctc    1560
tctcaaccta ttcattccta ctcatctaca taagtatctt cagctaaatg ttagaacata    1620
aacccataag tcacgtttga tgagtattag gcgtgacaca tgacaaatca cagactcaag    1680
caagataaag caaaatgatg tgtacataaa actccagagc tatatgtcat attgcaaaaa    1740
gaggagagct tataagacaa ggcatgactc acaaaaattc atttgccttt cgtgtcaaaa    1800
agaggagggc tttacattat ccatgtcata ttgcaaaaga aagagagaaa gaacaacaca    1860
atgctgcgtc aattatacat atctgtatgt ccatcattat tcatccacct ttcgtgtacc    1920
acacttcata tatcatgagt cacttcatgt ctggacatta acaaactcta tcttaacatt    1980
tagatgcaag agcctttatc tcactataaa tgcacgatga tttctcattg tttctcacaa    2040
aaagcattca gttcattagt cctacaacaa c                                   2071
```

```
<210> SEQ ID NO 11
<211> LENGTH: 194
<212> TYPE: DNA
<213> ORGANISM: Figwort mosaic virus
<220> FEATURE:
<221> NAME/KEY: enhancer
<222> LOCATION: (1)..(194)
```

<400> SEQUENCE: 11
agctgcttgt ggggaccaga caaaaaagga atggtgcaga attgttaggc gcacctacca 60
aaagcatctt tgcctttatt gcaaagataa agcagattcc tctagtacaa gtggggaaca 120
aaataacgtg gaaaagagct gtcctgacag cccactcact aatgcgtatg acgaacgcag 180
tgacgaccac aaaa 194

<210> SEQ ID NO 12
<211> LENGTH: 293
<212> TYPE: DNA
<213> ORGANISM: Cauliflower mosaic virus
<220> FEATURE:
<221> NAME/KEY: enhancer
<222> LOCATION: (1)..(293)

<400> SEQUENCE: 12
acttttcaac aaagggtaat atccggaaac ctcctcggat tccattgccc agctatctgt 60
cactttattg tgaagatagt ggaaaaggaa ggtggctcct acaaatgcca tcattgcgat 120
aaaggaaagg ctatcgttga agatgcctct gccgacagtg gtcccaaaga tggaccccca 180
cccacgagga gcatcgtgga aaaagaagac gttccaacca cgtcttcaaa gcaagtggat 240
tgatgtgata tctccactga cgtaagggat gacgaacaat cccactatcc ttc 293

<210> SEQ ID NO 13
<211> LENGTH: 68
<212> TYPE: DNA
<213> ORGANISM: Tobacco mosaic virus
<220> FEATURE:
<221> NAME/KEY: enhancer
<222> LOCATION: (1)..(68)

<400> SEQUENCE: 13
gtatttttac aacaattacc aacaacaaca aacaacaaac aacattacaa ttactattta 60
cataaacc 68

<210> SEQ ID NO 14
<211> LENGTH: 2221
<212> TYPE: DNA
<213> ORGANISM: Artificial Sequence
<220> FEATURE:
<223> OTHER INFORMATION: maize optimized GUS gene
<220> FEATURE:
<221> NAME/KEY: gene
<222> LOCATION: (1)..(2221)

<400> SEQUENCE: 14
atggtacgtc ctgtagaaac cccaacccgt gaaatcaaaa aactcgacgg cctgtgggca 60
ttcagtctgg atcgcgaaaa ctgtggaatt gatcagcgtt ggtgggaaag cgcgttacaa 120
gaaagccggg caattgctgt gccaggcagt tttaacgatc agttcgccga tgcagatatt 180
cgtaattatg cgggcaacgt ctggtatcag cgcgaagtct ttataccgaa aggttgggca 240
ggccagcgta tcgtgctgcg tttcgatgcg gtcactcatt acggcaaagt gtgggtcaat 300
aatcaggaag tgatggagca tcagggcggc tatacgccat ttgaagccga tgtcacgccg 360
tatgttattg ccgggaaaag tgtacgtatc accgtttgtg tgaacaacga actgaactgg 420
cagactatcc cgccgggaat ggtgattacc gacgaaaacg gcaagaaaaa gcagtcttac 480
ttccatgatt tctttaacta tgccggaatc catcgcagcg taatgctcta caccacgccg 540
aacacctggg tggacgatat caccgtggtg acgcatgtcg cgcaagactg taaccacgcg 600
tctgttgact ggcaggtacc aagctgcgaa tcttcgtttt tttaaggaat tctcgatctt 660

-continued

```
tatggtgtat aggctctggg ttttctgttt tttgtatctc ttaggatttt gtaaattcca    720
gatctttcta tggccactta gtagtatatt tcaaaaattc tccaatcgag ttcttcattc    780
gcattttcag tcattttctc ttcgacgttg tttttaagcc tgggtattac tcctatttag    840
ttgaactctg cagcaatctt agaaaattag ggttttgagg tttcgatttc tctaggtaac    900
cgatctattg cattcatctg aatttctgca tatatgtctt agatttctga taagcttacg    960
atacgttagg tgtaattgaa gtttattttt caagagtgtt atttttgtt tctgaatttt   1020
tcaggtggtg gccaatggtg atgtcagcgt tgaactgcgt gatgcggatc aacaggtggt   1080
tgcaactgga caaggcacta gcgggacttt gcaagtggtg aatccgcacc tctggcaacc   1140
gggtgaaggt tatctctatg aactgtgcgt cacagccaaa agccagacag agtgtgatat   1200
ctacccgctt cgcgtcggca tccggtcagt ggcagtgaag ggcgaacagt tcctgattaa   1260
ccacaaaccg ttctacttta ctggctttgg tcgtcatgaa gatgcggact tgcgtggcaa   1320
aggattcgat aacgtgctga tggtgcacga ccacgcatta atggactgga ttggggccaa   1380
ctcctaccgt acctcgcatt acccttacgc tgaagagatg ctcgactggg cagatgaaca   1440
tggcatcgtg gtgattgatg aaactgctgc tgtcggcttt aacctctctt taggcattgg   1500
tttcgaagcg ggcaacaagc cgaaagaact gtacagcgaa gaggcagtca acggggaaac   1560
tcagcaagcg cacttacagg cgattaaaga gctgatagcg cgtgacaaaa accacccaag   1620
cgtggtgatg tggagtattg ccaacgaacc ggatacccgt ccgcaaggtg cacgggaata   1680
tttcgcgcca ctggcggaag caacgcgtaa actcgacccg acgcgtccga tcacctgcgt   1740
caatgtaatg ttctgcgacg ctcacaccga taccatcagc gatctctttg atgtgctgtg   1800
cctgaaccgt tattacggat ggtatgtcca aagcggcgat ttggaaacgg cagagaaggt   1860
actggaaaaa gaacttctgg cctggcagga gaaactgcat cagccgatta tcatcaccga   1920
atacggcgtg gatacgttag ccgggctgca ctcaatgtac accgacatgt ggagtgaaga   1980
gtatcagtgt gcatggctgg atatgtatca ccgcgtcttt gatcgcgtca gcgccgtcgt   2040
cggtgaacag gtatggaatt tcgccgattt tgcgacctcg caaggcatat tgcgcgttgg   2100
cggtaacaag aaagggatct tcactcgcga ccgcaaaccg aagtcggcgg cttttctgct   2160
gcaaaaacgc tggactggca tgaacttcgg tgaaaaaccg cagcagggag gcaaacaatg   2220
a                                                                   2221
```

<210> SEQ ID NO 15
<211> LENGTH: 2226
<212> TYPE: DNA
<213> ORGANISM: Artificial Sequence
<220> FEATURE:
<223> OTHER INFORMATION: maize optimized endoglucanase
<220> FEATURE:
<221> NAME/KEY: gene
<222> LOCATION: (1)..(2226)

<400> SEQUENCE: 15

```
atgcgcgtgc tgctcgttgc gctggccctg ctggctctgg ccgcttctgc gacctctgcc     60
acccagggcg ctctggacag cgccgtgact gcgctccaat ccgctatcac caccttcagc    120
ggtgctcgcc aggatggcgc caagaccagc ggcttcacca gcgcccaggt gaccgccctg    180
atcaacagcg ccaaggccga caaggagggc gtccgcactt ctgctaacgg cgacgacgtg    240
tccccggtgg agtactgggt gaacagcagc gtgctgggcg cgttcaatgc tgccatcacc    300
gccctcgaga acgccagcgg ccagagcgct atcgacgccg cctacctggc tctcatccag    360
```

```
gccggcaaga cgttcaatga cgcgaagcgc cacggcacca ccccagacag gaccgccctc    420

aacaacgcga tcaccgccgc tgtgaacgcc aagaacggcg tccagaccgc cgctgacaag    480

gaccaggcca gcctgggcag cagctgggct accggcgctc agttcaacgc cctgaacacc    540

gccatcgaca gcgccaccgc cgtgaagaac aacgccaacg ccaccaaggc cagcgtggac    600

accgccgctg ccagcctgaa cgccgcgatc gccaccttca ccaccgccgt caccaacaac    660

ggcccaggca cccagacctt ccgcgacatc accgctgccc agctcgtggc cgagatcaag    720

atcggctgga acctgggcaa cagcctggac gcccacaacg gcttcccggc caacccaacc    780

gtggaccaga tggaacgcgg ctggggcaac ccagccacca ccaaggcgaa catcaccgcg    840

ctgaagaacg ccggcttcaa cgccatccgc atcccggtgt cctggaccaa ggccgccagc    900

ggcgctccga actacaccat ccgcaccgac tggatgaccc gcgtgaagga gatcgtcaac    960

tacgccgtgg acaacgacat gtacatcatc ctgaacaccc accacgacga ggacgtgctg   1020

accttcatga acagcaacgc cgctgccggc aaggccgcct tccagaagct gtgggagcag   1080

atcgccgctg ccttcaagga ctacaacgag aagctgatct tcgagggcct gaacgagcca   1140

aggaccccgg gcagcagcaa cgagtggaac ggcggcaccg acgaggagcg caacaacctg   1200

aacagctact acccgatctt cgtgaacact gtgcgcagca gcggcggcaa caacggcaag   1260

cgcatcctga tgatcaaccc ctacgccgcc agcatggaag ccgtggccat gaacgccctg   1320

accctgccag ccgactccgc cgccaacaag ctgatcgtgt ccttccacag ctaccagccg   1380

tacaacttcg ccctgaacaa ggacagcagc atcaacacct ggtccagcag cagctccggc   1440

gacaccagcc caatcaccgg cccgatcgac cgctactaca acaagttcgt gtcccagggc   1500

atcccggtga tcatcggcga gttcggcgcc atgaacaaga acaacgaggc tgtgcgcgcc   1560

cagtgggccg agtactacgt gtcctacgcc cagagcaagg gcatcaagtg cttctggtgg   1620

gacaacggcg tgaccagcgg ctctggcgag ctgttcggcc tgctgaaccg caccaacaac   1680

accttcacct acaacgccct gctgaacggc atgatgagcg gcaccggcgg cactgtgccc   1740

acgccaccca cccctccggc caccccaacc ccgccaacca ccatcaccgg caacctgggc   1800

acctaccagt tcggcaccca ggaggacggc gtttccccca actacaccca ggctgtgtgg   1860

gagctgtccg gcacgaatct gacgaccgcc aagaccacgg gcgccaagct ggtgctggtg   1920

ttcaccaccg cgccgaacgc cagcatgcac tttgtgtggc agggtccagc taatagcctg   1980

tggtggaacg agaaggagat cctgggcaac accggcaacc catctgctac gggcgttacc   2040

tggaacagcg gcaccaagac cctgaccatc ccgctgaccg ccaacagcgt gaaggactac   2100

tccgtgttca ccgcccagcc gagcctgcgc atcatcatcg cctactacaa cggcggcaac   2160

gtgaacgacc tgggcatcgt gtccgccaac ctgacccagg acgagctgaa ggccgaggcc   2220

aagtga                                                              2226
```

```
<210> SEQ ID NO 16
<211> LENGTH: 1590
<212> TYPE: DNA
<213> ORGANISM: Artificial Sequence
<220> FEATURE:
<223> OTHER INFORMATION: Maize optimized CBHI gene
<220> FEATURE:
<221> NAME/KEY: gene
<222> LOCATION: (1)..(1590)

<400> SEQUENCE: 16

atgcgcgtgc tgctcgtggc cctggccctg ctggctcttg ctgccagcgc cacctctcag     60

cagatcggca cctacaccgc cgagacccac ccaagcctga gctggtccac ctgcaagagc    120
```

```
ggcggttcct gcacgaccaa cagcggcgcc atcacccttg atgcgaactg gcgctgggtg    180
cacggcgtga acaccagcac caactgctac acgggtaaca cgtggaacac cgccatctgc    240
gacacggacg cttcctgcgc ccaggactgc gcgcttgatg gcgccgacta ctccggcacc    300
tacggcatca ccacctccgg caacagcctg cgcctgaact tcgtgaccgg cagcaatgtg    360
ggcagccgca cctacctgat ggccgacaac acccactacc agatcttcga cctgctgaac    420
caggagttca ccttcaccgt cgacgtgtcc cacctgccct gcggcctgaa cggcgccctc    480
tacttcgtga cgatggacgc cgacggcggc gtgtccaagt acccgaacaa caaggctggc    540
gcccagtacg gtgtgggcta ctgcgacagc cagtgcccga gggacctgaa gttcatcgcc    600
ggccaggcca acgtggaggg ctggaccccg agcagcaaca acgccaacac cggcctgggc    660
aaccacggcg cctgctgcgc cgagctggac atctgggagg ccaacagcat cagcgaggcc    720
ctgaccccac acccatgcga caccccaggc ctgtctgtgt gcaccaccga cgcctgcggc    780
ggcacctact ccagcgaccg ctacgccggc acctgcgacc cagacggctg cgacttcaac    840
ccgtaccgcc tgggcgtgac cgacttctac ggcagcggca agaccgtgga caccaccaag    900
ccgatcaccg tggtgaccca gttcgtgacc gacgacggca ccagcaccgg caccctgagc    960
gagatccgcc gctactacgt ccagaacggc gtggtgatcc cgcagccgag cagcaagatc   1020
agcggcgtgt ccggcaacgt gatcaacagc gacttctgcg acgccgagat cagcaccttc   1080
ggcgagaccg ccagcttcag caagcacggc ggcctggcca agatgggcgc tggcatggaa   1140
gccggcatgg tgctggtgat gagcctgtgg gacgactact ccgtgaacat gctgtggctg   1200
gacagcacct acccgaccaa cgccaccggg acgccaggcg ctgccagggg cagctgccca   1260
accacctcgg gcgaccccaa gaccgtcgag agccagagcg gcagcagcta cgtgaccttc   1320
agcgacatcc gcgtgggccc gttcaactcc acgttcagcg gtggctctag cacgggcggc   1380
tcctccacca ccaccgccag cggcaccacc accaccaagg cctccagcac gtctactagc   1440
tccacctcta ccggcaccgg cgttgctgcc cattggggcc agtgcggtgg ccagggctgg   1500
acgggtccaa cgacttgcgc ctccggcacc acctgcaccg tggtcaatcc gtactactcc   1560
cagtgcctga gcgagaagga cgagctgtga                                     1590
```

<210> SEQ ID NO 17
<211> LENGTH: 1596
<212> TYPE: DNA
<213> ORGANISM: Artificial Sequence
<220> FEATURE:
<223> OTHER INFORMATION: maize optimized CBHI
<220> FEATURE:
<221> NAME/KEY: gene
<222> LOCATION: (1)..(1596)

<400> SEQUENCE: 17

```
atgcgcgtgc tgctcgtggc cctggccctg ctggctcttg ctgccagcgc cacctctcag     60
cagatcggca cctacaccgc cgagacccac ccaagcctga gctggtccac ctgcaagagc    120
ggcggttcct gcacgaccaa cagcggcgcc atcacccttg atgcgaactg gcgctgggtg    180
cacggcgtga acaccagcac caactgctac acgggtaaca cgtggaacac cgccatctgc    240
gacacggacg cttcctgcgc ccaggactgc gcgcttgatg gcgccgacta ctccggcacc    300
tacggcatca ccacctccgg caacagcctg cgcctgaact tcgtgaccgg cagcaatgtg    360
ggcagccgca cctacctgat ggccgacaac acccactacc agatcttcga cctgctgaac    420
caggagttca ccttcaccgt cgacgtgtcc cacctgccct gcggcctgaa cggcgccctc    480
```

```
tacttcgtga cgatggacgc cgacggcggc gtgtccaagt acccgaacaa caaggctggc    540

gcccagtacg gtgtgggcta ctgcgacagc cagtgcccga gggacctgaa gttcatcgcc    600

ggccaggcca acgtggaggg ctggaccccg agcagcaaca acgccaacac cggcctgggc    660

aaccacggcg cctgctgcgc cgagctggac atctgggagg ccaacagcat cagcgaggcc    720

ctgaccccac acccatgcga caccccaggc ctgtctgtgt gcaccaccga cgcctgcggc    780

ggcacctact ccagcgaccg ctacgccggc acctgcgacc cagacggctg cgacttcaac    840

ccgtaccgcc tgggcgtgac cgacttctac ggcagcggca agaccgtgga caccaccaag    900

ccgatcaccg tggtgaccca gttcgtgacc gacgacggca ccagcaccgg caccctgagc    960

gagatccgcc gctactacgt ccagaacggc gtggtgatcc cgcagccgag cagcaagatc   1020

agcggcgtgt ccggcaacgt gatcaacagc gacttctgcg acgccgagat cagcaccttc   1080

ggcgagaccg ccagcttcag caagcacggc ggcctggcca agatgggcgc tggcatggaa   1140

gccggcatgg tgctggtgat gagcctgtgg gacgactact ccgtgaacat gctgtggctg   1200

gacagcacct acccgaccaa cgccaccggg acgccaggcg ctgccagggg cagctgccca   1260

accacctcgg gcgaccccaa gaccgtcgag agccagagcg gcagcagcta cgtgaccttc   1320

agcgacatcc gcgtgggccc gttcaactcc acgttcagcg gtggctctag cacgggcggc   1380

tcctccacca ccaccgccag cggcaccacc accaccaagg cctccagcac gtctactagc   1440

tccacctcta ccggcaccgg cgttgctgcc cattggggcc agtgcggtgg ccagggctgg   1500

acgggtccaa cgacttgcgc ctccggcacc acctgcaccg tggtcaatcc gtactactcc   1560

cagtgcctgg acgagctgaa ggccgaggcc aagtga                             1596
```

<210> SEQ ID NO 18
<211> LENGTH: 1943
<212> TYPE: DNA
<213> ORGANISM: Artificial Sequence
<220> FEATURE:
<223> OTHER INFORMATION: Maize R1 RNAi
<220> FEATURE:
<221> NAME/KEY: gene
<222> LOCATION: (1)..(1943)

<400> SEQUENCE: 18

```
gatgaccttg actctcccaa gttacttggt tacccaagca agccaattgg tctcttcata     60

aggcaatcaa tcatcttccg ttccgactcc aacggtgagg acctggaagg ttatgctgga    120

gcaggattat atgatagcgt accgatggat gaggaggatg aggttgtact tgattacaca    180

actgaccctc ttatagtaga ccgtggattc cgaagctcaa tcctctcaag catagcacgg    240

gctggccatg ccatcgagga gctatacggt tctcctcagg acgtcgaggg agtagtgaag    300

gatggaaaaa tctatgtagt ccagacaaga ctcgagaccc agctttcttg tacaaagtgg    360

ttggcgccaa agggcgaatt cactagtaag cttgggcccg cggccgcagg tatgttgctt    420

ccattgccaa actgttccct tttacccata ggctgattga tcttggctgt gtgatttttt    480

gcttgggttt ttgagctgat tcagcggcgc ttgcagcctc ttgatcgtgg tcttggctcg    540

cccatttctt gcgattcttt ggtgggtcgt cagctgaatc ttgcaggagt tttttgctgac    600

atgttcttgg gtttactgct ttcggtaaat ctgaaccaag aggggggttt ctgctgcagt    660

ttagtgggtt tactatgagc ggattcgggg tttcgaggaa aaccggcaaa aaacctcaaa    720

tcctcgacct ttagttttgc tgccacgttg ctccgcccca ttgcagagtt ctttttgccc    780

ccaaattttt ttttacttgg tgcagtaaga atcgcgcctc agtgattttc tcgactcgta    840

gtccgttgat actgtgtctt gcttatcact tgttctgctt aatctttttt gcttcctgag    900
```

```
gaatgtcttg gtgcctgtcg gtggatggcg aaccaaaaat gaagggtttt tgtttttga     960

actgagaaaa atctttgggt tttggttgg attctttcat ggagtcgcga ccttccgtat    1020

tcttctcttt gatctccccg cttgcggatt cataatattc ggaacttcat gttggctctg   1080

cttaatctgt agccaaatct tcatatctcc agggatcttt cgctctgtcc tatcggattt   1140

aggaattagg atctaactgg tgctaatact aaagggtaat ttggaaccat gccattataa   1200

ttttgcaaag tttgaggtat gccatcggta tctcaatgat acttactaaa acccaacaaa   1260

tccatttgat aaagctggtt cttttatccc tttgaaaaca ttgtcagagt atattggttc   1320

aggttgattt attttgaatc agtactcgca ctctgcttcg taaaccatag atgctttcag   1380

ttgtgtagat gaaacagctg tttttagtta tgttttgatc ttccaatgct tttgtgtgat   1440

gttattagtg ttgatttagc atggctttcc tgttcagaga tagtcttgca atgcttagtg   1500

atggctgttg actaattatt cttgtgcaag tgagtggttt tggtacgtgt tgctaagtgt   1560

aacctttctt tgcagggcgc caaccacttt gtacaagaaa gctgggtctc gagtcttgtc   1620

tggactacat agatttttcc atccttcact actccctcga cgtcctgagg agaaccgtat   1680

agctcctcga tggcatggcc agcccgtgct atgcttgaga ggattgagct tcggaatcca   1740

cggtctacta taagagggtc agttgtgtaa tcaagtacaa cctcatcctc ctcatccatc   1800

ggtacgctat catataatcc tgctccagca taaccttcca ggtcctcacc gttggagtcg   1860

gaacggaaga tgattgattg ccttatgaag agaccaattg gcttgcttgg gtaaccaagt   1920

aacttgggag agtcaaggtc atc                                           1943
```

<210> SEQ ID NO 19
<211> LENGTH: 561
<212> TYPE: DNA
<213> ORGANISM: Artificial Sequence
<220> FEATURE:
<223> OTHER INFORMATION: Maize optimized xylanase
<220> FEATURE:
<221> NAME/KEY: gene
<222> LOCATION: (1)..(561)

<400> SEQUENCE: 19

```
atggctagca ccgactactg gcaaaactgg accgacggcg gcggcaccgt gaacgctacc     60

aacggcagcg acggcaacta cagcgtgagc tggagcaact gcggcaactt cgtggtgggc    120

aagggctgga ccaccggcag cgctaccagg gtgatcaact acaacgctgg cgctttcagc    180

ccaagcggca acggctactt ggctttgtac ggctggacca ggaacagctt gatcgagtac    240

tacgtggtgg acagctgggg cacctacagg ccaaccggca cctacaaggg caccgtgacc    300

agcgacggcg gcacctacga catctacacc accaccagga ccaacgctcc aagcatcgac    360

ggcaacaaca ccaccttcac ccaattctgg agcgtgaggc aaagcaagag gccaatcggc    420

accaacaaca ccatcacctt cagcaaccat gtgaacgctt ggaagagcaa gggcatgaac    480

ttgggcagca gctggagcta ccaagtgttg gctaccgagg gctaccaaag cagcggctac    540

agcaacgtga ccgtgtggta g                                              561
```

<210> SEQ ID NO 20
<211> LENGTH: 1848
<212> TYPE: DNA
<213> ORGANISM: Artificial Sequence
<220> FEATURE:
<223> OTHER INFORMATION: maize optimized cry1Ab gene
<220> FEATURE:
<221> NAME/KEY: gene
<222> LOCATION: (1)..(1848)

<400> SEQUENCE: 20

```
atggacaaca accccaacat caacgagtgc atcccctaca actgcctgag caaccccgag      60
gtggaggtgc tgggcggcga gcgcatcgag accggctaca cccccatcga catcagcctg     120
agcctgaccc agttcctgct gagcgagttc gtgcccggcg ccggcttcgt gctgggcctg     180
gtggacatca tctggggcat cttcggcccc agccagtggg acgccttcct ggtgcagatc     240
gagcagttga taaaccaacg catagaggaa ttcgcccgca accaggccat cagccgcctg     300
gagggcctga gcaacctgta ccaaatctac gccgagagct tccgcgagtg ggaggccgac     360
cccaccaacc ccgccctgcg cgaggagatg cgcatccagt tcaacgacat gaacagcgcc     420
ctgaccaccg ccatccccct gttcgccgtg cagaactacc aggtgcccct gctgagcgtg     480
tacgtgcagg ccgccaacct gcacctgagc gtgctgcgcg acgtcagcgt gttcggccag     540
cgctggggct tcgacgccgc caccatcaac agccgctaca acgacctgac ccgcctgatc     600
ggcaactaca ccgaccacgc cgtgcgctgg tacaacaccg gcctggagcg cgtgtggggt     660
cccgacagcc gcgactggat caggtacaac cagttccgcc gcgagctgac cctgaccgtg     720
ctggacatcg tgagcctgtt ccccaactac gacagccgca cctaccccat ccgcaccgtg     780
agccagctga cccgcgagat ttacaccaac cccgtgctgg agaacttcga cggcagcttc     840
cgcggcagcg cccagggcat cgagggcagc atccgcagcc cccacctgat ggacatcctg     900
aacagcatca ccatctacac cgacgcccac cgcggcgagt actactggag cggccaccag     960
atcatggcca gccccgtcgg cttcagcggc cccgagttca ccttccccct gtacggcacg    1020
atgggcaacg ctgcacctca gcagcgcatc gtggcacagc tgggccaggg agtgtaccgc    1080
accctgagca gcaccctgta ccgtcgacct ttcaacatcg gcatcaacaa ccagcagctg    1140
agcgtgctgg acggcaccga gttcgcctac ggcaccagca gcaacctgcc cagcgccgtg    1200
taccgcaaga gcggcaccgt ggacagcctg gacgagatcc cccctcagaa caacaacgtg    1260
ccacctcgac agggcttcag ccaccgtctg agccacgtga gcatgttccg cagtggcttc    1320
agcaacagca gcgtgagcat catccgtgca cctatgttca gctggattca ccgcagtgcc    1380
gagttcaaca acatcatccc cagcagccag atcacccaga tcccccctgac caagagcacc    1440
aacctgggca gcggcaccag cgtggtgaag ggccccggct tcaccggcgg cgacatcctg    1500
cgccgcacca gccccggcca gatcagcacc ctgcgcgtga acatcaccgc ccccctgagc    1560
cagcgctacc gcgtccgcat ccgctacgcc agcaccacca acctgcagtt ccacaccagc    1620
atcgacggcc gccccatcaa ccagggcaac ttcagcgcca ccatgagcag cggcagcaac    1680
ctgcagagcg gcagcttccg caccgtgggc ttcaccaccc ccttcaactt cagcaacggc    1740
agcagcgtgt tcaccctgag cgcccacgtg ttcaacagcg gcaacgaggt gtacatcgac    1800
cgcatcgagt tcgtgcccgc cgaggtgacc ttcgaggccg agtactag                 1848
```

<210> SEQ ID NO 21
<211> LENGTH: 1002
<212> TYPE: DNA
<213> ORGANISM: Zea mays
<220> FEATURE:
<221> NAME/KEY: terminator
<222> LOCATION: (1)..(1002)

<400> SEQUENCE: 21

```
gcggcttctc ttcactcacc tgcagagtgc accgcaataa tcagcttccg gatggtggcg      60
ttttgtcagt tttggatgga aatgccgaac tggcagcgtc tgttttccct atgcatatgt     120
```

```
aatttcctgc ctctttatat tcactcttgt tgtcaagtcc aagtggaaaa tcttggcata    180

ttatacatat tgtaataata aacatcgtac aatctgcatg ctgttttgta ataattaatt    240

aatatcccag cccattggat ggacttgttt accaaggtgt tacttcagtc accctctttt    300

agttgtgcta aacagtttct gattgatatt tttttattag agtaacctag tgcatttact    360

taagagaaat gatatctagt ggcactagtg attagtttgc aaggttgaga acttgttact    420

cgctcctaga ggttaacact agcaagtgat tggagcttag ggtttttctt gaatttcact    480

agaaaaaata taaactagta tatcatgata tgcacttaag tctttttagt gttatctacc    540

gacactcaaa aaggctttct tgctactcat ttctcttact cctaaagcaa aaaaaaaata    600

gccaaatgac cctccctcta acaataatca taatgaaatc tcacctctct tttaggtgca    660

atatttttgt gggagtgggt ctttttgggt gactgagggg ctctaggaag gggatcagta    720

gagatatcta gcaaggtgtc aagtgtattc ctgagatggt taggttttga acaccacaca    780

tgtttctgag gaggggctct cataagctcc ttaggcactc catctctcac aataggggtg    840

gcagatttgg gaggagtgag cttgacatgt ttggggtgga tgaaggtttc tctgaaggtt    900

ttaggccact acactcacca accttaccaa cacaagtgac actcccatcc ttagcagcaa    960

agcctaaccc cgttccccca gttcccctct tgaactaact ga                       1002
```

<210> SEQ ID NO 22
<211> LENGTH: 1001
<212> TYPE: DNA
<213> ORGANISM: Zea mays
<220> FEATURE:
<221> NAME/KEY: terminator
<222> LOCATION: (1)..(1001)

<400> SEQUENCE: 22

```
gccatcagtc gttgaagctg ctgctgtatc tgggttatct agtgtctctg ccattgccca     60

aggatggtgc tgtctttcaa agtatttgta tggtttgtgt cgtgagtcgt gactgagctg    120

gtttcatgga ccagttgtgt tctcgttacc caaaactatc gtgcgaccgc atatggctta    180

atcatgaata aatgttgttt gaatttaaac tattcgctga atattgttgt tttttgtcat    240

gtcagttaat gttactaaat tggttgcctt ctaatttttg tttactggtg tttgtcgcac    300

cttatctttt tactgtatgt ttacttcagg ttctggcagt ctcatttttt gtgactagtt    360

aaaacttaca gctaaaaaaa tgcagttttt cattttcatt tgaagtttga ttagagctat    420

tgatacccgg accatcaggt taggttagtt gtgcatagaa tcataaatat taatcatgtt    480

ttctatgaat taagtcaaac ttgaaagtct ggctgaatat agtttctatg aatcatattg    540

atatacatgt ttgattattt gttttgctat tagctattta ctttggtgaa tctatatagg    600

cttatgcaga accttttttt ttgttctata tatccatatc ctagtactca gtagctctat    660

gttttctgga gactagtggc ttgctttttc gtatgtctaa ttttttgctt gaccattgca    720

aaacaaaaat tacctagtgt aatctctttt tataataatc ttgtaatgcg tctacctata    780

ggtcaaagta ggttttgttt ggaaccctta gagctaactg ttagctagtt gataaattat    840

tagctgagtt aagctagcta atgaactagt tttgatatta gctgaggatg tttgaaacct    900

aataattatt ttttattagc taactatact aaattttagt agagagattc caaacaggag    960

ttaacatggg atcagattgg ctatgcgttt gcaatcccat a                       1001
```

<210> SEQ ID NO 23
<211> LENGTH: 253
<212> TYPE: DNA
<213> ORGANISM: Agrobacterium tumefaciens
<220> FEATURE:
<221> NAME/KEY: terminator
<222> LOCATION: (1)..(253)

<400> SEQUENCE: 23

```
gatcgttcaa acatttggca ataaagtttc ttaagattga atcctgttgc cggtcttgcg     60

atgattatca tataatttct gttgaattac gttaagcatg taataattaa catgtaatgc    120

atgacgttat ttatgagatg ggtttttatg attagagtcc cgcaattata catttaatac    180

gcgatagaaa acaaaatata gcgcgcaaac taggataaat tatcgcgcgc ggtgtcatct    240

atgttactag atc                                                       253
```

<210> SEQ ID NO 24
<211> LENGTH: 1047
<212> TYPE: DNA
<213> ORGANISM: Zea mays
<220> FEATURE:
<221> NAME/KEY: terminator
<222> LOCATION: (1)..(1047)

<400> SEQUENCE: 24

```
gtccatgaca aagtaaaacg tacagagaca cttgataata tctatctatc atctcggaga     60

agacgaccga ccaataaaaa taagccaagt ggaagtgaag cttagctgta tatacaccgt    120

acgtcgtcgt cgtcgttccg gatcgatctc ggccggctag ctagcagaac gtgtacgtag    180

tagtatgtaa tgcatggagt gtggagctac tagctagctg gccgttcatt cgattataat    240

tcttcgctct gctgtggtag cagatgtacc tagtcgatct tgtacgacga agaagctggc    300

tagctagccg tctcgatcgt atatgtactg attaatctgc agattgaata aaaactacag    360

tacgcatatg atgcgtacgt acgtgtgtat agtttgtgct catatatgct cctcatcacc    420

tgcctgatct gcccatcgat ctctctcgta ctccttcctg ttaaatgcct tctttgacag    480

acacaccacc accagcagca gtgacgctct gcacgccgcc gctttaagac atgtaagata    540

ttttaagagg tataagatac caaggagcac aaatctggag cactgggata ttgcaaagac    600

aaaaaaaaaa caaaattaaa gtcccaccaa agtagagata gtaaagaggt ggatggatta    660

aaattatctc atgatttttg gatctgctca aatagatcga tatggtattc aggtctatgt    720

tgtatagcct tttcattagc tttctgaaaa aaaaatggta tgatgagtgc ggagtagcta    780

gggctgtgaa ggagtcggat gggcttccac gtacttgttt gtggccctag tccggttcta    840

tttaggtccg atccgagtcc ggcatggtcc ggttccatac gggctaggac caagctcggc    900

acgtgagttt taggcccgtc ggctagcccg agcacgaccc gtttttaaac tggctaggac    960

tcgcccattt aataagacaa acattgcaaa aaatagctct atttttttatt taaaatatat   1020

tgtttatttg tgaaatgtgt attattt                                       1047
```

<210> SEQ ID NO 25
<211> LENGTH: 1136
<212> TYPE: DNA
<213> ORGANISM: Oryza sativa
<220> FEATURE:
<221> NAME/KEY: terminator
<222> LOCATION: (1)..(1136)

<400> SEQUENCE: 25

```
tgacatggat atgatgatca gctcatcttc tatatcttat gctgttatgc agacagacac     60

tactgatgtg gctatatata tagtatttgt gtgctgctgc attttgttaa tcccttataa    120

attgctactt aattatctca tggagaattg gagagaccaa atgggcagag ctagctagtt    180
```

```
agctgtgccc aattaagaag ctaaatctat cagaagtgtg tactgatgag tgatgagtat    240

ttttcttcat ttgggatcaa attaaactaa gtaaaacata tatatttgac ttatgtttta    300

cgtgcatgca tgcatgctta attgtgtcac ctttggggat tcattttgta catatgtgca    360

ccattttgtg tgtacaatgc aggtttatat gactttttc gcaattacac gatggcccat    420

gcacataacc accatgcaca ctgcacgtac atccacaagt gtgccccttt aacacaaggc    480

aatacaccaa ataaattgta atgtgccact aaactttttt gaaagtgtaa ccgcgcgtat    540

gcttccgtgg cttatatatg actctggtgg ctgacttcta gggcatgtcg acctgagcat    600

cttcgtgtgg gtttcgactc tctaattctc ctggtctctg gcagttgtgg aaggggcgaa    660

actccagggt tttgattac tctctttcct cactctcaag ggttctgaaa gtcatcctac    720

aggaagaccg tttgtggtct tctgctggcg tcgctgtttt taggggttta ttaggagtgt    780

agtggagctt cgccaccacc ctccatctat ttaggagcaa cattttttg gtagtttttt    840

actttagcag tctttttgtt tctttctttg ttcccttatc cacatgcaat ggtcgtctga    900

ctggttacgt tgtgtaacaa aaactctgct tttttctaat atactgacgt gcaatccttt    960

ggtgcgttcg cgaaaagaaa gggggatcaa ttgcaagtat tttgtgggaa ttaaactttt   1020

cttgtgaaat tattgtaaaa ttccagcatt ctaaatgagc tctaatgtgt gataatttgc   1080

attctctata tatattgaat aattcttttg ttgactagtt gggtgcccgt gcgttg       1136
```

```
<210> SEQ ID NO 26
<211> LENGTH: 1803
<212> TYPE: DNA
<213> ORGANISM: Artificial Sequence
<220> FEATURE:
<223> OTHER INFORMATION: Maize optimized sucrose isomerase gene
<220> FEATURE:
<221> NAME/KEY: gene
<222> LOCATION: (1)..(1803)

<400> SEQUENCE: 26
```

```
atgcgcgtgc tgctcgtggc cctggccctg ctggctctcg ccgctagcgc cacctcccac     60

agccgcttca acccgatccg cctgccgacc acccacgagc cagccgtggc cgtgaacgac    120

ggcgtgtccg cccacccagt gtggtggaag gaggccgttt tctaccaggt gtacccgcgc    180

agcttcaagg acagcgacgg cgacggcatc ggcgacctga agggcctgac cgagaagctg    240

gactacctga aggccctggg catcaacgcc atctggatca acccgcacta cgacagcccg    300

aacaccgaca acggctacga tatccgcgac taccgcaaga tcatgaagga atacggcacg    360

atggacgact tcgaccgcct gatcgccgag atgaagaagc gcgacatgcg cctgatgatc    420

gacgtggtgg tgaaccacac cagcgacgag cacgagtggt tcgtggagag caagaagtcc    480

aaggacaacc cgtaccgcga ctactacatc tggcgcgacg gcaaggacgg cacccagccg    540

aacaactacc cgagcttctt cggcggcagc gcctggcaga aggacaacgc cacccagcag    600

tactacctgc actacttcgg cgtccagcag ccggacctga actgggacaa cccgaaagtg    660

agggaggagg tgtacgacat gctgaggttc tggatcgaca agggcgtgtc cggcctgagg    720

atggacaccg tggccacctt cagcaagaac ccggccttcc cggacctgac cccgaagcag    780

ctccagaact tcgcctacac ctacacccag ggcccgaacc tgcaccgcta catccaggag    840

atgcaccaga aggtcctggc caagtacgac gtggtgtctg ccggcgagat cttcggcgtg    900

ccgctcgagg aggccgctcc gttcatcgac cagcgccgga aggaactgga catggccttc    960

agcttcgacc tgatccgcct cgacagggcc gtggaggaga ggtggcgccg caacgactgg   1020

accctgagcc agttccgcca gatcaacaac cgcctggtgg acatggccgg ccagcacggc   1080
```

-continued

```
tggaacacgt tcttcctcag caaccacgac aacccgaggg ccgtgtccca cttcggcgac   1140

gacaggccag agtggaggac ccgcagcgcc aaggccctgg ccaccctggc cctgacccag   1200

agggctaccc cattcatcta ccagggcgac gagctgggca tgaccaacta cccgttcacc   1260

agcctgagcg agttcgacga tatcgaggtg aagggcttct ggcaggactt cgtggagact   1320

ggcaaggtga agccagacgt gttcctcgag aacgtgaagc agaccagccg cgacaacagc   1380

cgcaccccgt tccagtggag caacaccgcc caggccggct tcaccaccgg caccccgtgg   1440

ttccgcatca acccgaacta caagaacatc aacgccgagg agcagaccca gaacccggac   1500

agcatcttcc acttctaccg ccagctgatc gagctgaggc acgccacccc ggccttcacc   1560

tacggcacct accaggacct ggacccgaac aacaacgagg tgctggccta cacccgcgag   1620

ctgaaccagc agcgctacct ggtggtggtc aacttcaagg agaagccggt ccactacgtg   1680

ctgcccaaga ccctgagcat caagcagagc ctgctcgaga gcggccagaa ggacaaggtc   1740

gagccgaacg ccaccaccct cgagcttcag ccctggcaga gcggcatcta tcagctgaac   1800

tga                                                                 1803
```